(12) United States Patent
Rusconi

(10) Patent No.: US 8,389,489 B2
(45) Date of Patent: Mar. 5, 2013

(54) MODULATORS OF COAGULATION FACTORS

(75) Inventor: Christopher Rusconi, Durham, NC (US)

(73) Assignee: Regado Biosciences, Inc., Basking Ridge, NJ (US)

( * ) Notice: Subject to any disclaimer, the term of this patent is extended or adjusted under 35 U.S.C. 154(b) by 241 days.

(21) Appl. No.: 12/758,565

(22) Filed: Apr. 12, 2010

(65) Prior Publication Data

US 2010/0197900 A1 Aug. 5, 2010

Related U.S. Application Data

(60) Continuation of application No. 11/821,183, filed on Jun. 22, 2007, now Pat. No. 7,723,315, which is a division of application No. 11/113,378, filed on Apr. 22, 2005, now Pat. No. 7,304,041.

(60) Provisional application No. 60/564,873, filed on Apr. 22, 2004.

(51) Int. Cl.
*A01N 43/04* (2006.01)
*C07H 21/02* (2006.01)
*C07H 21/04* (2006.01)
*C12P 19/34* (2006.01)
*C12Q 1/68* (2006.01)

(52) U.S. Cl. ............ 514/44; 435/6; 435/91.1; 435/375; 435/455; 536/23.1; 536/24.3; 536/24.5

(58) Field of Classification Search ............ 435/6, 91.1, 435/91.31, 455, 375, 458; 514/44, 1, 2; 536/23.1, 536/24.5, 24.3
See application file for complete search history.

(56) References Cited

U.S. PATENT DOCUMENTS

| | | | |
|---|---|---|---|
| 5,245,022 A | 9/1993 | Weis et al. | |
| 5,270,163 A | 12/1993 | Gold et al. | |
| 5,475,096 A | 12/1995 | Gold et al. | |
| 5,476,766 A | 12/1995 | Gold et al. | |
| 5,532,130 A | 7/1996 | Alul | |
| 5,534,408 A | 7/1996 | Green et al. | |
| 5,543,293 A | 8/1996 | Gold et al. | |
| 5,552,391 A | 9/1996 | Coutts et al. | |
| 5,582,981 A | 12/1996 | Toole et al. | |
| 5,594,121 A | 1/1997 | Froehler et al. | |
| 5,595,877 A | 1/1997 | Gold et al. | |
| 5,606,047 A | 2/1997 | Coutts et al. | |
| 5,645,985 A | 7/1997 | Froehler et al. | |
| 5,648,214 A | 7/1997 | Nieuwlandt et al. | |
| 5,660,985 A | 8/1997 | Pieken et al. | |
| 5,670,633 A | 9/1997 | Cook et al. | |
| 5,670,637 A | 9/1997 | Gold et al. | |
| 5,681,702 A | 10/1997 | Collins et al. | |
| 5,686,242 A | 11/1997 | Bruice et al. | |
| 5,696,249 A | 12/1997 | Gold et al. | |
| 5,723,323 A | 3/1998 | Kauffman et al. | |
| 5,750,729 A | 5/1998 | Alexander et al. | |
| 5,756,291 A | 5/1998 | Griffin et al. |
| 5,760,202 A | 6/1998 | Cook et al. |
| 5,780,221 A | 7/1998 | Schumacher et al. |
| 5,780,449 A | 7/1998 | Bracht et al. |
| 5,780,610 A | 7/1998 | Collins et al. |
| 5,792,608 A | 8/1998 | Swaminathan et al. |
| 5,792,613 A | 8/1998 | Schmidt et al. |
| 5,807,718 A | 9/1998 | Joyce et al. |
| 5,814,476 A | 9/1998 | Kauffman et al. |
| 5,817,781 A | 10/1998 | Swaminathan et al. |
| 5,817,785 A | 10/1998 | Gold et al. |
| 5,830,653 A | 11/1998 | Froehler et al. |
| 5,839,443 A | 11/1998 | Rose |
| 5,840,867 A | 11/1998 | Toole et al. |
| 5,843,653 A | 12/1998 | Gold et al. |
| 5,859,221 A | 1/1999 | Cook et al. |
| 5,861,254 A | 1/1999 | Schneider et al. |
| 5,861,501 A | 1/1999 | Benseler et al. |
| 5,872,232 A | 2/1999 | Cook et al. |
| 5,879,917 A | 3/1999 | Essigman et al. |
| 5,882,870 A | 3/1999 | Nadeau et al. |
| 5,882,941 A | 3/1999 | Essigman et al. |
| 5,891,689 A | 4/1999 | Takle et al. |
| 5,935,776 A | 8/1999 | Green et al. |
| 5,958,691 A | 9/1999 | Pieken et al. |
| 5,989,823 A | 11/1999 | Jayasena et al. |
| 6,001,820 A | 12/1999 | Hirsh et al. |
| 6,004,746 A | 12/1999 | Brent et al. |
| 6,005,087 A | 12/1999 | Cook et al. |
| 6,011,020 A | 1/2000 | Gold et al. |
| 6,051,388 A | 4/2000 | Bodenhamer |
| 6,054,274 A | 4/2000 | Sampson et al. |
| 6,060,056 A | 5/2000 | Coutts et al. |
| 6,083,696 A | 7/2000 | Biesecker et al. |
| 6,093,555 A | 7/2000 | Dudycz |
| 6,110,462 A | 8/2000 | Barbas et al. |
| 6,110,721 A | 8/2000 | Gibbs et al. |

(Continued)

FOREIGN PATENT DOCUMENTS

| EP | 0593901 | 4/1994 |
|---|---|---|
| EP | 1026243 | 8/2000 |

(Continued)

OTHER PUBLICATIONS

Dunn et al., Mouse Whoe Genome Scaffolding, Alignment of Accession No. AZ771181 (2000).*
Agrawal et al., "Antisense therapeutics: is it as simple as complementary base recognition?" Molecular Medicine Today, vol. 6, pp. 72-81 (2000).
Aldaz-Carroll et al., "Apical loop-internal loop interactions: a new RNA-RNA recognition motif identified through in vitro selection against RNA hairpins of hepatitis C virus mRNA", Biochemistry, vol. 41, No. 18, pp. 5883-5893 (2002) Abstract only.

(Continued)

*Primary Examiner* — Jane Zara
(74) *Attorney, Agent, or Firm* — King & Spalding

(57) ABSTRACT

The invention provides improved nucleic acid ligands that inhibit coagulation and improved modulators of the nucleic acid ligands to provide ideal modulators of coagulation. These improved nucleic acid ligands and modulators are particularly useful for inhibiting coagulation in a host undergoing a therapeutic regime such as surgery or coronary artery bypass.

17 Claims, 21 Drawing Sheets

U.S. PATENT DOCUMENTS

| | | | |
|---|---|---|---|
| 6,110,900 | A | 8/2000 | Gold et al. |
| 6,111,095 | A | 8/2000 | Benseler et al. |
| 6,114,038 | A | 9/2000 | Castro et al. |
| 6,117,557 | A | 9/2000 | Massie, II et al. |
| 6,120,997 | A | 9/2000 | Wong et al. |
| 6,127,119 | A | 10/2000 | Stephens et al. |
| 6,127,173 | A | 10/2000 | Eckstein et al. |
| 6,136,545 | A | 10/2000 | Hosel et al. |
| 6,147,204 | A | 11/2000 | Gold et al. |
| 6,150,461 | A | 11/2000 | Takei et al. |
| 6,153,410 | A | 11/2000 | Arnold et al. |
| 6,163,714 | A | 12/2000 | Stanley et al. |
| 6,171,795 | B1 | 1/2001 | Korman et al. |
| 6,177,263 | B1 | 1/2001 | Arnold et al. |
| 6,177,555 | B1 | 1/2001 | Jayasena et al. |
| 6,180,348 | B1 | 1/2001 | Li |
| 6,183,967 | B1 | 2/2001 | Jayasena et al. |
| 6,222,025 | B1 | 4/2001 | Cook et al. |
| 6,258,601 | B1 | 7/2001 | Monia et al. |
| 6,315,995 | B1 | 11/2001 | Pinsky |
| 6,316,198 | B1 | 11/2001 | Skouv et al. |
| 6,316,403 | B1 | 11/2001 | Pinsky |
| 6,331,398 | B1 | 12/2001 | Gold et al. |
| 6,391,300 | B1 | 5/2002 | Rose |
| 6,531,584 | B1 | 3/2003 | Cook et al. |
| 7,304,041 | B2 | 12/2007 | Rusconi |
| 2003/0083294 | A1 | 5/2003 | Sullenger et al. |
| 2003/0175703 | A1 | 9/2003 | Sullenger et al. |

FOREIGN PATENT DOCUMENTS

| | | |
|---|---|---|
| JP | 11127864 | 5/1999 |
| WO | WO 92/14842 | 9/1992 |
| WO | WO 94/06811 | 3/1994 |
| WO | WO 94/08050 | 4/1994 |
| WO | WO 97/42317 | 11/1997 |
| WO | WO 99/33971 | 7/1999 |
| WO | WO 99/50462 | 10/1999 |
| WO | WO 00/20040 | 4/2000 |
| WO | WO 00/22114 | 4/2000 |
| WO | WO 00/24912 | 5/2000 |
| WO | WO 00/42063 | 7/2000 |
| WO | WO 00/42064 | 7/2000 |
| WO | WO 00/47774 | 8/2000 |
| WO | WO 02/26932 | 4/2002 |
| WO | WO 02/096926 | 12/2002 |
| WO | WO 03/093422 | 11/2003 |
| WO | WO 2004/011680 | 2/2004 |
| WO | WO 2004/014844 | 2/2004 |
| WO | WO 2004/047742 | 6/2004 |
| WO | WO 2004/050899 | 6/2004 |
| WO | WO 2005/010150 | 2/2005 |
| WO | WO 2005/014533 | 2/2005 |
| WO | WO 2005/052121 | 6/2005 |
| WO | WO 2005/084412 | 9/2005 |
| WO | WO 2005/111238 | 11/2005 |
| WO | WO 2006/029258 | 3/2006 |
| WO | WO 2006/033854 | 3/2006 |

OTHER PUBLICATIONS

Becker, "Protein-Binding Oligonucleotides: the Next Frontier in Antithrombotic Therapy", J. Thrombosis and Thrombolysis, vol. 17, No. 2, pp. 157-159 (2004).

Beigelman et al., "Chemical modification of hammerhead ribozymes. Catalytic activity and nuclease resistance", J Biol. Chem., vol. 270, No. 43, pp. 25702-25708 (1995).

Biedenkapp et al., "Viral myb oncogene encodes a sequence-specific DNA-binding activity", Nature, vol. 335, pp. 835-837 (1988).

Biesecker et al., "Derivation of RNA aptamer inhibitors of human complement C5", Immunopharmacology, vol. 42, No. 1-3, pp. 219-230 (1999) Abstract only.

Black and Azizkhan-Clifford, "Regulation of E2F: a family of transcription factors involved in proliferation control," Gene, vol. 237, No. 2, pp. 281-302 (1999).

Boiziau et al., "DNA Aptamers Selected Against the HIV-1 trans-Activation-responsive RNA element form RNA-DNA Kissing Complexes", J Biol. Chem., vol. 274, No. 18, pp. 12730-12737 (1999).

Burke et al., "A novel axidophilic RNA motif that recognizes Coenzyme A", Biochemistry, pp. 4653-4663 (Nov. 25, 1997) Abstract only.

Callas et al., "Comparative pharmaceology of site directed antithrombin agents. Implication in drug development", Thrombosis and Haemostasis, vol. 74, No. 1, pp. 473-481 (1995) Abstract only.

Charlton et al., "In vivo imaging of inflammation using an aptamer inhibitor of human neutrophil elastase", Chemistry & Biology, vol. 4, No. 11, pp. 809-816 (1997) Abstract only.

Chase and Williams, "Single-stranded DNA binding proteins required for DNA replication," Annu. Rev. Biochem., vol. 55, pp. 103-136 (1986).

Collin et al., "NMR characterization of a kissing complex formed between the TAR RNA element of HIV-1 and a DNA aptamer," Nucl. Ac. Rsch., vol. 28, pp. 3386-3391 (2000).

Dale et al., "Direct covalent mercuration of nucletides and polynucleotides," Biochemistry, vol. 14, No. 11, pp. 2447-2457 (1975).

Darfeuille et al., "RNA and N3'→P5' kissing aptamers targeted to the trans-activation responsive (TAR) RNA of the human immunodeficiency virus-1", Nucleosides Nucleic Acids, vol. 20, No. 4-7, pp. 441-449 (2001) Abstract only.

Davies et al., Chap. 8, p. 185, in RNA World (Cold Spring Harbor Laboratory Press; eds. Gestlaad and Atkins; 1993).

DeAnda Jr. et al., "Pilot study of the efficacy of a thrombin inhibitor for use during cardiopulmonary bypass," Ann. Thorac. Surg., vol. 58, No. 2, pp. 344-350 (1994).

Duconge et al., "Is a Closing "GA PAIR"a Rule for Stable Loop-Loop RNA Complexes?", J Biol. Chem., vol. 275, No. 28, pp. 21287-21294 (2000).

Eichorn et al., "Interaction of metal ions with polynucleotides and related compounds. XII. The relative effect of various metal ions on DNA helicity", J. Am. Chem. Soc., vol. 90, No. 26, pp. 7323-7328 (1968).

Ellington and Szostak, "Selection of RNAs with ligand-specific binding activity 134 from pools of random sequence molecules", Cold Spring Harbor "RNA Processing", Conference (1990) Abstract only.

Feuerstein et al., "Antithrombotic efficacy of a novel murine antihuman factor IX antibody in rats", Arterioscler. Thromb. Vasco Biol., vol. 19, No. 10, pp. 2554-2562 (1999).

Gal et al., "Selection of a RNA aptamer that binds to human activated protein C and inhibits its protease function", European Journal of Biochemistry, vol. 252, No. 3, pp. 553-562 (1998) Abstract only.

Good et al., "Expression of small, therapeutic RNAs in human cell nuclei", Gene Ther., vol. 4, No. 1, pp. 45-54 (1997).

Griffin et al., "In vivo anticoagulant properties of a novel nucleotide-based thrombin inhibitor 138 and demonstration of regional anticoagulation in a extracorporeal circuits", Blood, vol. 81, No. 12, pp. 3271-3276 (1993).

Harbour and Dean, "The Rb/E2F pathway: expanding roles and emerging paradigms", Genes Dev., vol. 14, No. 19, pp. 2393-2409 (2000).

Helin and Ed, "The retinoblastoma protein as a transcriptional repressor", Trends Cell Biol., vol. 3, No. 2, pp. 43-46 (1993).

Hunter, "Braking the cycle", Cell, vol. 75, No. 5, pp. 839-841 (1993).

Hwang et al., "Inhibition of gene expression in human cells through small molecule-RNA interactions", PNAS, vol. 96, No. 23, 12997-13002 (1999).

Ishizaki et al., "Inhibition of cell proliferation by an RNA ligand that selectively blocks E2F function", Nature Med., vol. 2, No. 12, pp. 1386-1389 (1996).

Jen et al., "Suppression of gene expression by targeted disruption of messenger RNA: available options and current strategies", Stem Cells, vol. 18, No. 5, pp. 307-319 (2000).

Kinzler and Vogelstein, "Whole genome PCR: application to the identification of sequences bound by gene regulatory proteins", Nuc. Acids Rsch., vol. 17, pp. 3645 (1989).

La Thangue, "DRTF1/E2F: an expanding family of heterodimeric transcription factors implicated in cell-cycle control", Trends Biochem. Sci., vol. 19, No. 3, pp. 108-114 (1994).

LeClerc et al., "A three dimensional model of the Rev-binding element of HIV-a derived from analyses of apramers", Nat. Struct. Biol., vol. 1, pp. 293-300 (1994) Abstract only.

Lee et al., "Isolation of a nuclease-resistant decoy RNA that can protect human acetylcholine receptors from myasthenic antibodies", Nature Biotechnol., vol. 15, No. 1, pp. 41-45 (1997).

Leva et al., "GnRH Binding RNA and DNA Spiegelmers: A Novel Approach toward GnRH Antagonism", Chemistry & Biology. vol. 8, pp. 351-359 (2002).

Li et al., "A novel nucleotide-based thrombin inhibitor inhibits clot-bound thrombin and reduces arterial platelet thrombus formation", Blood, vol. 83, No. 3, pp. 677-682 (1994) Abstract only.

Lippard et al., "Platinum complexes: probes of polynucleotide structure and antitumor drugs", Acc. Chem. Res., vol. 11, pp. 211-217 (1978).

Liu et al., "Screening of Functional Antidotes of RNA Aptamers Against Bovine Thrombin." FEBS Letters, vol. 562,. pp. 125-128 (2004).

Mann et al., "Surface-dependent reactions of the vitamin K-dependent enzyme complexes", Blood, vol. 76, No. 1, pp. 1-16 (1990).

Nevins, "E2F: a link between the Rb tumor suppressor protein and viral oncoproteins", Science, vol. 258, No. 5081, pp. 424-429 (1992).

Oliphant et al., "Defining the sequence specificity of DNA-binding proteins by selecting binding sites from random-sequence oligonucleotides: analysis of yeast GCN4 protein", Mol. Cell. Biol., vol. 9, pp. 2944-2949 (1989).

Opalinska et al., "Nucleic-acid therapeutics: basic principles and recent applications", Nature Reviews Drug Discovery, vol. 1, pp. 503-512 (2002).

Padmanabhan et al., "The structure of alpha-thrombin inhibited by a 15-mer single-stranded DNA aptamer", Journal of Biological Chemistry, vol. 268, No. 24, pp. 17651-17654 (1993) Abstract only.

Pieken et al., "Kinetic characterization of ribonuclease-resistant 2'-modified hammerhead ribozymes", Science, vol. 253, No. 5017, pp. 314-317 (1991).

Robertson and Joyce, "Selection in vitro of an RNA enzyme that specifically cleaves single-stranded DNA", Nature, vol. 344, pp. 467-468 (1990).

Rusconi et al., "RNA aptamers as reversible antagonists of coagulation factor Ixa", Nature, vol. 419. pp. 90-94 (2002).

Rusconi et al., "Blocking the initiation of coagulation by RNA aptamers to factor VIIA", Thrombosis and Haemostasis, vol. 85, No. 5, pp. 841-848 (2000).

Shaw et al., "A novel oligodeoxynucleotide inhibitor of thrombin I. In vitro metabolic stability in plasma and serum", Pharmaceutical Research, vol. 12, No. 12, pp. 1937-1942 (1995) Abstract only.

Sheehan and Lan, "Phosphothioate Oligonucleotides Inhibit the Intrinsic Tenase Complex", Blood, vol. 92, No. 5, pp. 1617-1625 (1998).

Sherr, "Mammalian G1 cyclins", Cell, vol. 73, No. 6, pp. 1059-1065 (1993).

Sherr and Roberts, "Inhibitors of mammalian GI cyclin-dependent kinases", Genes Dev., vol. 9, No. 10, pp. 1149-1163 (1995).

Smirnov et al., "Effect of Loop Sequence and Size on DNA Aptamer Stability", Biochemistry, vol. 39, pp. 1462-1468 (2000).

Sullenger et al., "Therapeutic Aptamers and Antidotes: A Novel Approach to Safer Drug Design", Ernst Schering Res Found Workshop, vol. 43, pp. 217-223 (2003).

Sullenger et al., "Overexpression of TAR sequences renders cells resistant to human immunodeficiency virus replication", Cell, vol. 63, No. 3, pp. 601-608 (1990).

Szostak, "Structure and activity of ribozymes; redesigning the molecules of life", Conference of the International Symposium on Bioorganic Chemistry, Interlaken (May 4-6, 1988).

Tasset et al., "Oligonucleotide inhibitors of human thrombin that bind distinct epitopes", Journal of Molecular Biology, vol. 272, No. 5, pp. 688-698 (1997) Abstract only.

Tinevez et al., "Selective inhibition of cell-free translation by oligonucleotides targeted to a mRNA hairpin structure", Nucleic Acids Research, vol. 26, No. 10, pp. 2273-2278 (1998).

Tucker et al., "Detection and plasma pharmacokinetics of an anti-vascular endothelial growth factor oligonucleotide-aptamer in (NX1838) rhesus monkeys", Journal of Chromatography, vol. 732, No. 1, pp. 203-212 (1999) Abstract only.

Wahlestedt et al., "Potent and nontoxic antisense oligonucleotides containing locked nucleic acids", Proc. Natl. Acad. Sci., vol. 97, No. 10, pp. 5633-5638 (2000).

Weinberg, "The retinoblastoma protein and cell cycle control", Cell, vol. 81, No. 3, pp. 323-330 (1995).

Werstuck et al., "Controlling Gene Expression in Living Cells Through Small Molecule-RNA Interactions", Science, vol. 282, No. 5387, pp. 296-298 (1998).

White et al., "Developing aptamers into therapeutics", J. Clin Inv., vol. 106, No. 8, pp. 929-934 (2000).

Williams et al., "Bioactive and nuclease-resistant L-DNA ligand of vasopressin", Proc. Natl. Acad. Sci., vol. 94, pp. 11285-11290 (1997).

Willis et al., "Liposome-anchored vascular endothelial growth factor aptamers", Bioconjug. Chem., vol. 9, No. 5, pp. 573-582 (1998).

Willis et al., "Liposome-anchored vascular endothelial growth factor aptamers", Bioconjug. Chem., vol. 9, No. 5, pp. 633 (1998) [Erratum Collins B., corrected to Collins B.D.].

* cited by examiner

D. Apt 18-20.

E. Apt 21

F. Apt 22-29

G. Apt 30-34

H. Apt 35-39

SEQUENCE LISTING

<160> NUMBER OF SEQ ID NOS: 59

<210> SEQ ID NO 1
<211> LENGTH: 17
<212> TYPE: RNA
<213> ORGANISM: Artificial Sequence
<220> FEATURE:
<223> OTHER INFORMATION: Synthetic aptamer

<400> SEQUENCE: 1
cgcgguauag uccccau                                                  17

<210> SEQ ID NO 2
<211> LENGTH: 14
<212> TYPE: RNA
<213> ORGANISM: Artificial Sequence
<220> FEATURE:
<223> OTHER INFORMATION: Synthetic aptamer

<400> SEQUENCE: 2
cgcgguauag uccc                                                     14

<210> SEQ ID NO 3
<211> LENGTH: 15
<212> TYPE: RNA
<213> ORGANISM: Artificial Sequence
<220> FEATURE:

<223> OTHER INFORMATION: Synthetic aptamer

<400> SEQUENCE: 3
cgcgguauag uccac                                                    15

<210> SEQ ID NO 4
<211> LENGTH: 16
<212> TYPE: RNA
<213> ORGANISM: Artificial Sequence
<220> FEATURE:
<223> OTHER INFORMATION: Synthetic aptamer

<400> SEQUENCE: 4
cgcgguauag uccauc                                                   16

<210> SEQ ID NO 5
<211> LENGTH: 14
<212> TYPE: RNA
<213> ORGANISM: Artificial Sequence
<220> FEATURE:
<223> OTHER INFORMATION: Synthetic aptamer

<400> SEQUENCE: 5
cgcgguauag ucag                                                     14

<210> SEQ ID NO 6
<211> LENGTH: 15
<212> TYPE: RNA
<213> ORGANISM: Artificial Sequence
<220> FEATURE:
<223> OTHER INFORMATION: Synthetic aptamer

<400> SEQUENCE: 6
cgcgguauag ucagg                                                    15

<210> SEQ ID NO 7
<211> LENGTH: 16
<212> TYPE: RNA
<213> ORGANISM: Artificial Sequence
<220> FEATURE:
<223> OTHER INFORMATION: Synthetic aptamer

<400> SEQUENCE: 7
cgcgguauag ucagag                                                   16

<210> SEQ ID NO 8
<211> LENGTH: 17
<212> TYPE: RNA
<213> ORGANISM: Artificial Sequence
<220> FEATURE:
<223> OTHER INFORMATION: Synthetic aptamer

<400> SEQUENCE: 8
cgcgguauag uccucac                                                  17

<210> SEQ ID NO 9
<211> LENGTH: 35
<212> TYPE: DNA
<213> ORGANISM: Artificial Sequence
<220> FEATURE:
<223> OTHER INFORMATION: Synthetic aptamer

<400> SEQUENCE: 9
auggggacua uaccgcguaa ugcugccucc ccaut                              35

<210> SEQ ID NO 10

```
<211> LENGTH: 35
<212> TYPE: DNA
<213> ORGANISM: Artificial Sequence
<220> FEATURE:
<223> OTHER INFORMATION: Synthetic aptamer

<400> SEQUENCE: 10
auggggacua uaccgcguaa ugcugccucc ccaut                                   35

<210> SEQ ID NO 11
<211> LENGTH: 29
<212> TYPE: DNA
<213> ORGANISM: Artificial Sequence
<220> FEATURE:
<223> OTHER INFORMATION: Synthetic aptamer

<400> SEQUENCE: 11
gggacuauac cgcguaaugc ugccuccct                                         29

<210> SEQ ID NO 12
<211> LENGTH: 31
<212> TYPE: DNA
<213> ORGANISM: Artificial Sequence
<220> FEATURE:
<223> OTHER INFORMATION: Synthetic aptamer

<400> SEQUENCE: 12
guggacuaua ccgcguaaug cugccuccac t                                      31

<210> SEQ ID NO 13
<211> LENGTH: 33
<212> TYPE: DNA
<213> ORGANISM: Artificial Sequence
<220> FEATURE:
<223> OTHER INFORMATION: Synthetic aptamer

<400> SEQUENCE: 13
gauggacuau accgcguaau gcugccucca uct                                    33

<210> SEQ ID NO 14
<211> LENGTH: 29
<212> TYPE: DNA
<213> ORGANISM: Artificial Sequence
<220> FEATURE:
<223> OTHER INFORMATION: Synthetic aptamer

<400> SEQUENCE: 14
cugacuauac cgcguaaugc ugccucagt                                         29

<210> SEQ ID NO 15
<211> LENGTH: 31
<212> TYPE: DNA
<213> ORGANISM: Artificial Sequence
<220> FEATURE:
<223> OTHER INFORMATION: Synthetic aptamer

<400> SEQUENCE: 15
ccugacuaua ccgcguaaug cugccucagg t                                      31

<210> SEQ ID NO 16
<211> LENGTH: 33
<212> TYPE: DNA
<213> ORGANISM: Artificial Sequence
<220> FEATURE:
<223> OTHER INFORMATION: Synthetic aptamer

<400> SEQUENCE: 16
```

```
cucugacuau accgcguaau gcugccucag agt                                      33
```

<210> SEQ ID NO 17
<211> LENGTH: 35
<212> TYPE: DNA
<213> ORGANISM: Artificial Sequence
<220> FEATURE:
<223> OTHER INFORMATION: Synthetic aptamer

<400> SEQUENCE: 17

```
gugaggacua uaccgcguaa ugcugccucc ucact                                    35
```

<210> SEQ ID NO 18
<211> LENGTH: 35
<212> TYPE: DNA
<213> ORGANISM: Artificial Sequence
<220> FEATURE:
<223> OTHER INFORMATION: Synthetic aptamer

<400> SEQUENCE: 18

```
gugaggacua uaccgcguaa ugcugccucc ucact                                    35
```

<210> SEQ ID NO 19
<211> LENGTH: 31
<212> TYPE: DNA
<213> ORGANISM: Artificial Sequence
<220> FEATURE:
<223> OTHER INFORMATION: Synthetic aptamer

<400> SEQUENCE: 19

```
guggacuaua ccgcguaaug cugccuccac t                                        31
```

<210> SEQ ID NO 20
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (1)..(1)
<223> OTHER INFORMATION: RNA 2'OH
<220> FEATURE:
<221> NAME/KEY: modified_base
<222> LOCATION: (2)..(2)
<223> OTHER INFORMATION: 2'-Fluoro uridine
<220> FEATURE:
<221> NAME/KEY: misc_feature
<222> LOCATION: (3)..(6)
<223> OTHER INFORMATION: RNA 2'OH
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro cytidine
<220> FEATURE:
<221> NAME/KEY: modified_base
<222> LOCATION: (9)..(9)
<223> OTHER INFORMATION: 2'-Fluoro uridine
<220> FEATURE:
<221> NAME/KEY: misc_feature
<222> LOCATION: (10)..(10)
<223> OTHER INFORMATION: RNA 2'OH
<220> FEATURE:
<221> NAME/KEY: modified_base
<222> LOCATION: (11)..(11)
<223> OTHER INFORMATION: 2'-Fluoro uridine
<220> FEATURE:
<221> NAME/KEY: misc_feature
<222> LOCATION: (12)..(12)

```
<223> OTHER INFORMATION: RNA 2'OH
<220> FEATURE:
<221> NAME/KEY: modified_base
<222> LOCATION: (13)..(14)
<223> OTHER INFORMATION: 2'-Fluoro cytidine
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro cytidine
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro uridine
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro uridine
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro cytidine
<220> FEATURE:
<221> NAME/KEY: modified_base
<222> LOCATION: (24)..(24)
<223> OTHER INFORMATION: 2'-Fluoro uridine
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro cytidine
<220> FEATURE:
<221> NAME/KEY: modified_base
<222> LOCATION: (28)..(28)
<223> OTHER INFORMATION: 2'-Fluoro uridine
<220> FEATURE:
<221> NAME/KEY: modified_base
<222> LOCATION: (29)..(32)
<223> OTHER INFORMATION: 2'-Fluoro cytidine
<220> FEATURE:
<221> NAME/KEY: misc_feature
<222> LOCATION: (30)..(33)
<223> OTHER INFORMATION: RNA 2'OH
<220> FEATURE:
<221> NAME/KEY: modified_base
<222> LOCATION: (34)..(34)
<223> OTHER INFORMATION: 2'-Fluoro uridine
<220> FEATURE:
<221> NAME/KEY: modified_base
<222> LOCATION: (35)..(35)
<223> OTHER INFORMATION: inverted 2'H Thymidine

<400> SEQUENCE: 20
auggggacua uaccgcguaa ugcugccucc ccaut                                35

<210> SEQ ID NO 21
<211> LENGTH: 35
<212> TYPE: DNA
<213> ORGANISM: Artificial Sequence
<220> FEATURE:
```

```
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl Adenine
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: modified_base
<222> LOCATION: (3)..(6)
<223> OTHER INFORMATION: 2'-O-methyl Guanine
<220> FEATURE:
<221> NAME/KEY: modified_base
<222> LOCATION: (7)..(7)
<223> OTHER INFORMATION: 2'-O-methyl Adenine
<220> FEATURE:
<221> NAME/KEY: modified_base
<222> LOCATION: (8)..(8)
<223> OTHER INFORMATION: 2'-Fluoro Cytidine
<220> FEATURE:
<221> NAME/KEY: modified_base
<222> LOCATION: (9)..(9)
<223> OTHER INFORMATION: 2'-Fluoro Uridine
<220> FEATURE:
<221> NAME/KEY: misc_feature
<222> LOCATION: (10)..(10)
<223> OTHER INFORMATION: RNA 2'OH
<220> FEATURE:
<221> NAME/KEY: modified_base
<222> LOCATION: (11)..(11)
<223> OTHER INFORMATION: 2'-Fluoro Uridine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(14)
<223> OTHER INFORMATION: 2'-Fluoro cytidine
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro cytidine
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'Fluoro Uridine
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'Fluoro Cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: misc_feature
<222> LOCATION: (25)..(25)
```

```
<223> OTHER INFORMATION: RNA 2'OH
<220> FEATURE:
<221> NAME/KEY: modified_base
<222> LOCATION: (26)..(27)
<223> OTHER INFORMATION: 2'Fluoro Cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(32)
<223> OTHER INFORMATION: 2'Fluoro Cytidine
<220> FEATURE:
<221> NAME/KEY: modified_base
<222> LOCATION: (33)..(33)
<223> OTHER INFORMATION: 2'-O-methyl Adenine
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymine

<400> SEQUENCE: 21
auggggacua uaccgcguaa ugcugccucc ccaut                          35

<210> SEQ ID NO 22
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (1)..(1)
<223> OTHER INFORMATION: RNA 2'OH
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: misc_feature
<222> LOCATION: (3)..(6)
<223> OTHER INFORMATION: RNA 2'OH
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'Fluoro Cytidine
<220> FEATURE:
<221> NAME/KEY: modified_base
<222> LOCATION: (9)..(9)
<223> OTHER INFORMATION: 2'Fluoro Uridine
<220> FEATURE:
<221> NAME/KEY: modified_base
<222> LOCATION: (10)..(10)
<223> OTHER INFORMATION: 2'-O-methyl Adenine
<220> FEATURE:
<221> NAME/KEY: modified_base
<222> LOCATION: (11)..(11)
<223> OTHER INFORMATION: 2'Fluoro Uridine
<220> FEATURE:
<221> NAME/KEY: modified_base
<222> LOCATION: (12)..(12)
<223> OTHER INFORMATION: 2'-O-methyl Adenine
<220> FEATURE:
<221> NAME/KEY: modified_base
<222> LOCATION: (13)..(14)
<223> OTHER INFORMATION: 2'Fluoro Cytidine
<220> FEATURE:
<221> NAME/KEY: misc_feature
<222> LOCATION: (15)..(15)
```

```
<223> OTHER INFORMATION: RNA 2'OH
<220> FEATURE:
<221> NAME/KEY: modified_base
<222> LOCATION: (16)..(16)
<223> OTHER INFORMATION: 2'Fluoro Cytidine
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'Fluoro Uridine
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'Fluoro Cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'Fluoro Cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(30)
<223> OTHER INFORMATION: 2'Fluoro Cytidine
<220> FEATURE:
<221> NAME/KEY: modified_base
<222> LOCATION: (31)..(32)
<223> OTHER INFORMATION: 2'Fluoro Cytidine
<220> FEATURE:
<221> NAME/KEY: misc_feature
<222> LOCATION: (33)..(33)
<223> OTHER INFORMATION: RNA 2'OH
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymidine

<400> SEQUENCE: 22
auggggacua uaccgcguaa ugcugccucc ccaut                           35

<210> SEQ ID NO 23
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (1)..(1)
```

```
<223> OTHER INFORMATION: RNA 2'OH
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: misc_feature
<222> LOCATION: (3)..(7)
<223> OTHER INFORMATION: RNA 2'OH
<220> FEATURE:
<221> NAME/KEY: modified_base
<222> LOCATION: (8)..(8)
<223> OTHER INFORMATION: 2'Fluoro cytidine
<220> FEATURE:
<221> NAME/KEY: modified_base
<222> LOCATION: (9)..(9)
<223> OTHER INFORMATION: 2'Fluoro Uridine
<220> FEATURE:
<221> NAME/KEY: misc_feature
<222> LOCATION: (10)..(10)
<223> OTHER INFORMATION: RNA 2'OH
<220> FEATURE:
<221> NAME/KEY: modified_base
<222> LOCATION: (11)..(11)
<223> OTHER INFORMATION: 2'Fluoro Uridine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(14)
<223> OTHER INFORMATION: 2'Fluoro cytidine
<220> FEATURE:
<221> NAME/KEY: modified_base
<222> LOCATION: (15)..(15)
<223> OTHER INFORMATION: 2'-O-methyl Guanine
<220> FEATURE:
<221> NAME/KEY: modified_base
<222> LOCATION: (16)..(16)
<223> OTHER INFORMATION: 2'Fluoro cytidine
<220> FEATURE:
<221> NAME/KEY: modified_base
<222> LOCATION: (17)..(17)
<223> OTHER INFORMATION: 2'-O-methyl Guanine
<220> FEATURE:
<221> NAME/KEY: modified_base
<222> LOCATION: (18)..(18)
<223> OTHER INFORMATION: 2'Fluoro Uridine
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'Fluoro cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: modified_base
<222> LOCATION: (25)..(25)
<223> OTHER INFORMATION: 2'-O-methyl Guanine
<220> FEATURE:
<221> NAME/KEY: modified_base
<222> LOCATION: (26)..(27)
<223> OTHER INFORMATION: 2'Fluoro cytidine
<220> FEATURE:
<221> NAME/KEY: modified_base
<222> LOCATION: (28)..(28)
```

```
<223> OTHER INFORMATION: 2'Fluoro Uridine
<220> FEATURE:
<221> NAME/KEY: modified_base
<222> LOCATION: (29)..(30)
<223> OTHER INFORMATION: 2'Fluoro cytidine
<220> FEATURE:
<221> NAME/KEY: modified_base
<222> LOCATION: (31)..(32)
<223> OTHER INFORMATION: 2'Fluoro cytidine
<220> FEATURE:
<221> NAME/KEY: misc_feature
<222> LOCATION: (33)..(33)
<223> OTHER INFORMATION: RNA 2'OH
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymidine

<400> SEQUENCE: 23
augggGacua uaccgcguaa ugcugccucc ccaut                               35

<210> SEQ ID NO 24
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: misc_feature
<222> LOCATION: (1)..(1)
<223> OTHER INFORMATION: RNA 2'OH
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: misc_feature
<222> LOCATION: (3)..(7)
<223> OTHER INFORMATION: RNA 2'OH
<220> FEATURE:
<221> NAME/KEY: modified_base
<222> LOCATION: (8)..(8)
<223> OTHER INFORMATION: 2'Fluoro Cytidine
<220> FEATURE:
<221> NAME/KEY: modified_base
<222> LOCATION: (9)..(9)
<223> OTHER INFORMATION: 2'Fluoro Uridine
<220> FEATURE:
<221> NAME/KEY: misc_feature
<222> LOCATION: (10)..(10)
<223> OTHER INFORMATION: RNA 2'OH
<220> FEATURE:
<221> NAME/KEY: modified_base
<222> LOCATION: (11)..(11)
<223> OTHER INFORMATION: 2'Fluoro Uridine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(14)
<223> OTHER INFORMATION: 2'Fluoro Cytidine
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro Cytidine
<220> FEATURE:
<221> NAME/KEY: misc_feature
<222> LOCATION: (17)..(17)
```

<223> OTHER INFORMATION: RNA 2'OH
<220> FEATURE:
<221> NAME/KEY: modified_base
<222> LOCATION: (18)..(18)
<223> OTHER INFORMATION: 2'Fluoro Uridine
<220> FEATURE:
<221> NAME/KEY: modified_base
<222> LOCATION: (19)..(20)
<223> OTHER INFORMATION: 2'-O-methyl Adenine
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: modified_base
<222> LOCATION: (22)..(22)
<223> OTHER INFORMATION: 2'-O-methyl Guanine
<220> FEATURE:
<221> NAME/KEY: modified_base
<222> LOCATION: (23)..(23)
<223> OTHER INFORMATION: 2'Fluoro Cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'Fluoro Cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(30)
<223> OTHER INFORMATION: 2'Fluoro Cytidine
<220> FEATURE:
<221> NAME/KEY: modified_base
<222> LOCATION: (31)..(32)
<223> OTHER INFORMATION: 2'Fluoro Cytidine
<220> FEATURE:
<221> NAME/KEY: misc_feature
<222> LOCATION: (33)..(33)
<223> OTHER INFORMATION: RNA 2'OH
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymidine

<400> SEQUENCE: 24
auggggacua uaccgcguaa ugcugccucc ccaut                              35

<210> SEQ ID NO 25
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl Adenine
<220> FEATURE:
<221> NAME/KEY: modified_base
<222> LOCATION: (2)..(2)
<223> OTHER INFORMATION: 2'Fluoro Uridine
<220> FEATURE:
<221> NAME/KEY: modified_base
<222> LOCATION: (3)..(6)

-continued

```
<223> OTHER INFORMATION: 2'-O-methyl Guanine
<220> FEATURE:
<221> NAME/KEY: modified_base
<222> LOCATION: (7)..(7)
<223> OTHER INFORMATION: 2'-O-methyl Adenine
<220> FEATURE:
<221> NAME/KEY: modified_base
<222> LOCATION: (8)..(8)
<223> OTHER INFORMATION: 2'Fluoro Cytidine
<220> FEATURE:
<221> NAME/KEY: modified_base
<222> LOCATION: (9)..(9)
<223> OTHER INFORMATION: 2'Fluoro Uridine
<220> FEATURE:
<221> NAME/KEY: modified_base
<222> LOCATION: (10)..(10)
<223> OTHER INFORMATION: 2'-O-methyl Adenine
<220> FEATURE:
<221> NAME/KEY: modified_base
<222> LOCATION: (11)..(11)
<223> OTHER INFORMATION: 2'Fluoro Uridine
<220> FEATURE:
<221> NAME/KEY: modified_base
<222> LOCATION: (12)..(12)
<223> OTHER INFORMATION: 2'-O-methyl Adenine
<220> FEATURE:
<221> NAME/KEY: modified_base
<222> LOCATION: (13)..(14)
<223> OTHER INFORMATION: 2'Fluoro Cytidine
<220> FEATURE:
<221> NAME/KEY: modified_base
<222> LOCATION: (15)..(15)
<223> OTHER INFORMATION: 2'-O-methyl Guanine
<220> FEATURE:
<221> NAME/KEY: modified_base
<222> LOCATION: (16)..(16)
<223> OTHER INFORMATION: 2'Fluoro Cytidine
<220> FEATURE:
<221> NAME/KEY: modified_base
<222> LOCATION: (17)..(17)
<223> OTHER INFORMATION: 2'-O-methyl Guanine
<220> FEATURE:
<221> NAME/KEY: modified_base
<222> LOCATION: (18)..(18)
<223> OTHER INFORMATION: 2'Fluoro Uridine
<220> FEATURE:
<221> NAME/KEY: modified_base
<222> LOCATION: (19)..(20)
<223> OTHER INFORMATION: 2'-O-methyl Adenine
<220> FEATURE:
<221> NAME/KEY: modified_base
<222> LOCATION: (21)..(21)
<223> OTHER INFORMATION: 2'Fluoro Uridine
<220> FEATURE:
<221> NAME/KEY: modified_base
<222> LOCATION: (22)..(22)
<223> OTHER INFORMATION: 2'-O-methyl Guanine
<220> FEATURE:
<221> NAME/KEY: modified_base
<222> LOCATION: (23)..(23)
<223> OTHER INFORMATION: 2'Fluoro Cytidine
<220> FEATURE:
<221> NAME/KEY: modified_base
<222> LOCATION: (24)..(24)
<223> OTHER INFORMATION: 2'Fluoro Uridine
<220> FEATURE:
<221> NAME/KEY: modified_base
<222> LOCATION: (25)..(25)
<223> OTHER INFORMATION: 2'-O-methyl Guanine
<220> FEATURE:
<221> NAME/KEY: modified_base
<222> LOCATION: (26)..(27)
<223> OTHER INFORMATION: 2'Fluoro Cytidine
<220> FEATURE:
<221> NAME/KEY: modified_base
<222> LOCATION: (28)..(28)
<223> OTHER INFORMATION: 2'Fluoro Uridine
<220> FEATURE:
<221> NAME/KEY: modified_base
<222> LOCATION: (29)..(30)
```

<223> OTHER INFORMATION: 2'Fluoro Cytidine
<220> FEATURE:
<221> NAME/KEY: modified_base
<222> LOCATION: (31)..(32)
<223> OTHER INFORMATION: 2'Fluoro Cytidine
<220> FEATURE:
<221> NAME/KEY: modified_base
<222> LOCATION: (33)..(33)
<223> OTHER INFORMATION: 2'-O-methyl Adenine
<220> FEATURE:
<221> NAME/KEY: modified_base
<222> LOCATION: (34)..(34)
<223> OTHER INFORMATION: 2'Fluoro Uridine
<220> FEATURE:
<221> NAME/KEY: modified_base
<222> LOCATION: (35)..(35)
<223> OTHER INFORMATION: inverted 2'H Thymidine

<400> SEQUENCE: 25
auggggacua uaccgcguaa ugcugccucc ccaut        35

<210> SEQ ID NO 26
<211> LENGTH: 29
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(3)
<223> OTHER INFORMATION: 2'-O-methyl Guanine
<220> FEATURE:
<221> NAME/KEY: modified_base
<222> LOCATION: (4)..(4)
<223> OTHER INFORMATION: 2'-O-methyl Adenine
<220> FEATURE:
<221> NAME/KEY: modified_base
<222> LOCATION: (5)..(5)
<223> OTHER INFORMATION: 2'-Fluoro Cytidine
<220> FEATURE:
<221> NAME/KEY: modified_base
<222> LOCATION: (6)..(6)
<223> OTHER INFORMATION: 2'-Fluoro Uracil
<220> FEATURE:
<221> NAME/KEY: modified_base
<222> LOCATION: (7)..(7)
<223> OTHER INFORMATION: 2'-O-methyl Adenine
<220> FEATURE:
<221> NAME/KEY: modified_base
<222> LOCATION: (8)..(8)
<223> OTHER INFORMATION: 2'-Fluoro Uracil
<220> FEATURE:
<221> NAME/KEY: modified_base
<222> LOCATION: (9)..(9)
<223> OTHER INFORMATION: 2'-O-methyl Adenine
<220> FEATURE:
<221> NAME/KEY: modified_base
<222> LOCATION: (10)..(10)
<223> OTHER INFORMATION: 2'-Fluoro Cytidine
<220> FEATURE:
<221> NAME/KEY: modified_base
<222> LOCATION: (11)..(11)
<223> OTHER INFORMATION: 2'-Fluoro Cytidine
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(13)
<223> OTHER INFORMATION: 2'-Fluoro Cytidine
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)

```
<223> OTHER INFORMATION: 2'-Fluoro Uracil
<220> FEATURE:
<221> NAME/KEY: misc_feature
<222> LOCATION: (16)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro Uracil
<220> FEATURE:
<221> NAME/KEY: misc_feature
<222> LOCATION: (19)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro Cytidine
<220> FEATURE:
<221> NAME/KEY: modified_base
<222> LOCATION: (21)..(21)
<223> OTHER INFORMATION: 2'-Fluoro Uracil
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(24)
<223> OTHER INFORMATION: 2'-Fluoro Cytidine
<220> FEATURE:
<221> NAME/KEY: modified_base
<222> LOCATION: (25)..(25)
<223> OTHER INFORMATION: 2'-O-methyl Uracil
<220> FEATURE:
<221> NAME/KEY: modified_base
<222> LOCATION: (26)..(28)
<223> OTHER INFORMATION: 2'-O-methyl Cytosine
<220> FEATURE:
<221> NAME/KEY: modified_base
<222> LOCATION: (29)..(29)
<223> OTHER INFORMATION: inverted 2'H T

<400> SEQUENCE: 26
gggacuauac cgcguaaugc ugccuccct                                              29

<210> SEQ ID NO 27
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'-Fluoro C
<220> FEATURE:
<221> NAME/KEY: modified_base
<222> LOCATION: (7)..(7)
<223> OTHER INFORMATION: 2'-Fluoro U
<220> FEATURE:
<221> NAME/KEY: modified_base
<222> LOCATION: (8)..(8)
```

```
<223> OTHER INFORMATION: 2'-O-methyl A
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'-Fluoro C
<220> FEATURE:
<221> NAME/KEY: misc_feature
<222> LOCATION: (13)..(13)
<223> OTHER INFORMATION: RNA 2'OH
<220> FEATURE:
<221> NAME/KEY: modified_base
<222> LOCATION: (14)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro U
<220> FEATURE:
<221> NAME/KEY: misc_feature
<222> LOCATION: (17)..(18)
<223> OTHER INFORMATION: RNA 2'OH
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: misc_feature
<222> LOCATION: (20)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro C
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-O-methyl U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 27
```
guggacuaua ccgcguaaug cugccuccac t                                31

<210> SEQ ID NO 28
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl A
<220> FEATURE:
<221> NAME/KEY: modified_base
<222> LOCATION: (3)..(3)
<223> OTHER INFORMATION: 2'-O-methyl U
<220> FEATURE:
<221> NAME/KEY: modified_base
<222> LOCATION: (4)..(5)
<223> OTHER INFORMATION: 2'-O-methyl G
<220> FEATURE:
<221> NAME/KEY: modified_base
<222> LOCATION: (6)..(6)
<223> OTHER INFORMATION: 2'-O-methyl A
<220> FEATURE:
<221> NAME/KEY: modified_base
<222> LOCATION: (7)..(7)
<223> OTHER INFORMATION: 2'-Fluoro C
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(10)
<223> OTHER INFORMATION: 2'-Fluoro U
<220> FEATURE:
<221> NAME/KEY: modified_base
<222> LOCATION: (11)..(11)
<223> OTHER INFORMATION: 2'-O-methyl A
<220> FEATURE:
<221> NAME/KEY: modified_base
<222> LOCATION: (12)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro C
<220> FEATURE:
<221> NAME/KEY: misc_feature
<222> LOCATION: (16)..(16)
<223> OTHER INFORMATION: RNA 2'OH
<220> FEATURE:
<221> NAME/KEY: modified_base
<222> LOCATION: (17)..(17)
<223> OTHER INFORMATION: 2'-Fluoro U
<220> FEATURE:
<221> NAME/KEY: misc_feature
<222> LOCATION: (18)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro U
<220> FEATURE:
<221> NAME/KEY: misc_feature
<222> LOCATION: (21)..(21)

```
<223> OTHER INFORMATION: RNA 2'OH
<220> FEATURE:
<221> NAME/KEY: modified_base
<222> LOCATION: (22)..(22)
<223> OTHER INFORMATION: 2'-Fluoro C
<220> FEATURE:
<221> NAME/KEY: modified_base
<222> LOCATION: (23)..(23)
<223> OTHER INFORMATION: 2'-Fluoro U
<220> FEATURE:
<221> NAME/KEY: misc_feature
<222> LOCATION: (24)..(24)
<223> OTHER INFORMATION: RNA 2'OH
<220> FEATURE:
<221> NAME/KEY: modified_base
<222> LOCATION: (25)..(26)
<223> OTHER INFORMATION: 2'-Fluoro C
<220> FEATURE:
<221> NAME/KEY: modified_base
<222> LOCATION: (27)..(27)
<223> OTHER INFORMATION: 2'-O-methyl U
<220> FEATURE:
<221> NAME/KEY: modified_base
<222> LOCATION: (28)..(29)
<223> OTHER INFORMATION: 2'-O-methyl C
<220> FEATURE:
<221> NAME/KEY: modified_base
<222> LOCATION: (30)..(30)
<223> OTHER INFORMATION: 2'-O-methyl A
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 28
gauggacuau accgcguaau gcugccucca uct                                33

<210> SEQ ID NO 29
<211> LENGTH: 29
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl C
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(5)
<223> OTHER INFORMATION: 2'-Fluoro C
<220> FEATURE:
<221> NAME/KEY: modified_base
<222> LOCATION: (6)..(6)
<223> OTHER INFORMATION: 2'-Fluoro U
<220> FEATURE:
<221> NAME/KEY: modified_base
<222> LOCATION: (7)..(7)
```

```
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(10)
<223> OTHER INFORMATION: 2'-Fluoro C
<220> FEATURE:
<221> NAME/KEY: modified_base
<222> LOCATION: (11)..(11)
<223> OTHER INFORMATION: 2'-Fluoro C
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro U
<220> FEATURE:
<221> NAME/KEY: misc_feature
<222> LOCATION: (16)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(24)
<223> OTHER INFORMATION: 2'-Fluoro C
<220> FEATURE:
<221> NAME/KEY: modified_base
<222> LOCATION: (25)..(25)
<223> OTHER INFORMATION: 2'-O-methyl U
<220> FEATURE:
<221> NAME/KEY: modified_base
<222> LOCATION: (26)..(26)
<223> OTHER INFORMATION: 2'-O-methyl C
<220> FEATURE:
<221> NAME/KEY: modified_base
<222> LOCATION: (27)..(27)
<223> OTHER INFORMATION: 2'-O-methyl A
<220> FEATURE:
<221> NAME/KEY: modified_base
<222> LOCATION: (28)..(28)
<223> OTHER INFORMATION: 2'-O-methyl G
<220> FEATURE:
<221> NAME/KEY: modified_base
<222> LOCATION: (29)..(29)
```

-continued

<223> OTHER INFORMATION: inverted 2'H T

<400> SEQUENCE: 29
cugacuauac cgcguaaugc ugccucagt                      29

<210> SEQ ID NO 30
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(2)
<223> OTHER INFORMATION: 2'-O-methyl C
<220> FEATURE:
<221> NAME/KEY: modified_base
<222> LOCATION: (3)..(3)
<223> OTHER INFORMATION: 2'-O-methyl U
<220> FEATURE:
<221> NAME/KEY: modified_base
<222> LOCATION: (4)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'-Fluoro C
<220> FEATURE:
<221> NAME/KEY: modified_base
<222> LOCATION: (7)..(7)
<223> OTHER INFORMATION: 2'-Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'-Fluoro C
<220> FEATURE:
<221> NAME/KEY: misc_feature
<222> LOCATION: (13)..(13)
<223> OTHER INFORMATION: RNA 2'OH
<220> FEATURE:
<221> NAME/KEY: modified_base
<222> LOCATION: (14)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro U
<220> FEATURE:
<221> NAME/KEY: misc_feature
<222> LOCATION: (17)..(18)
<223> OTHER INFORMATION: RNA 2'OH
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: misc_feature
<222> LOCATION: (20)..(20)

```
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro C
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-O-methyl U
<220> FEATURE:
<221> NAME/KEY: modified_base
<222> LOCATION: (27)..(27)
<223> OTHER INFORMATION: 2'-O-methyl C
<220> FEATURE:
<221> NAME/KEY: modified_base
<222> LOCATION: (28)..(28)
<223> OTHER INFORMATION: 2'-O-methyl A
<220> FEATURE:
<221> NAME/KEY: modified_base
<222> LOCATION: (29)..(30)
<223> OTHER INFORMATION: 2'-O-methyl G
<220> FEATURE:
<221> NAME/KEY: modified_base
<222> LOCATION: (31)..(31)
<223> OTHER INFORMATION: inverted 2'H T

<400> SEQUENCE: 30
ccugacuaua ccgcguaaug cugccucagg t                           31

<210> SEQ ID NO 31
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl C
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl C
<220> FEATURE:
<221> NAME/KEY: modified_base
<222> LOCATION: (4)..(4)
<223> OTHER INFORMATION: 2'-O-methyl U
<220> FEATURE:
<221> NAME/KEY: modified_base
<222> LOCATION: (5)..(5)
<223> OTHER INFORMATION: 2'-O-methyl G
<220> FEATURE:
<221> NAME/KEY: modified_base
<222> LOCATION: (6)..(6)
<223> OTHER INFORMATION: 2'-O-methyl A
<220> FEATURE:
<221> NAME/KEY: modified_base
<222> LOCATION: (7)..(7)
<223> OTHER INFORMATION: 2'-Fluoro C
<220> FEATURE:
<221> NAME/KEY: modified_base
<222> LOCATION: (8)..(8)
```

-continued

```
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(10)
<223> OTHER INFORMATION: 2'-Fluoro U
<220> FEATURE:
<221> NAME/KEY: modified_base
<222> LOCATION: (11)..(11)
<223> OTHER INFORMATION: 2'-O-methyl A
<220> FEATURE:
<221> NAME/KEY: modified_base
<222> LOCATION: (12)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro C
<220> FEATURE:
<221> NAME/KEY: misc_feature
<222> LOCATION: (16)..(16)
<223> OTHER INFORMATION: RNA 2'OH
<220> FEATURE:
<221> NAME/KEY: modified_base
<222> LOCATION: (17)..(17)
<223> OTHER INFORMATION: 2'-Fluoro U
<220> FEATURE:
<221> NAME/KEY: misc_feature
<222> LOCATION: (18)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro U
<220> FEATURE:
<221> NAME/KEY: misc_feature
<222> LOCATION: (21)..(21)
<223> OTHER INFORMATION: RNA 2'OH
<220> FEATURE:
<221> NAME/KEY: modified_base
<222> LOCATION: (22)..(22)
<223> OTHER INFORMATION: 2'-Fluoro C
<220> FEATURE:
<221> NAME/KEY: modified_base
<222> LOCATION: (23)..(23)
<223> OTHER INFORMATION: 2'-Fluoro U
<220> FEATURE:
<221> NAME/KEY: misc_feature
<222> LOCATION: (24)..(24)
<223> OTHER INFORMATION: RNA 2'OH
<220> FEATURE:
<221> NAME/KEY: modified_base
<222> LOCATION: (25)..(26)
<223> OTHER INFORMATION: 2'-Fluoro C
<220> FEATURE:
<221> NAME/KEY: modified_base
<222> LOCATION: (27)..(27)
<223> OTHER INFORMATION: 2'-O-methyl U
<220> FEATURE:
<221> NAME/KEY: modified_base
<222> LOCATION: (28)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl G
<220> FEATURE:
<221> NAME/KEY: modified_base
<222> LOCATION: (31)..(31)
```

-continued

<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl G
<220> FEATURE:
<221> NAME/KEY: modified_base
<222> LOCATION: (33)..(33)
<223> OTHER INFORMATION: inverted 2'H T

<400> SEQUENCE: 31
cucugacuau accgcguaau gcugccucag agt           33

<210> SEQ ID NO 32
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl A
<220> FEATURE:
<221> NAME/KEY: modified_base
<222> LOCATION: (2)..(2)
<223> OTHER INFORMATION: 2'-Fluoro U
<220> FEATURE:
<221> NAME/KEY: modified_base
<222> LOCATION: (3)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)

```
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(32)
<223> OTHER INFORMATION: 2'-Fluoro C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-Fluoro U
<220> FEATURE:
<221> NAME/KEY: modified_base
<222> LOCATION: (35)..(35)
<223> OTHER INFORMATION: inverted 2'H T

<400> SEQUENCE: 32
auggggacua uaccgcguaa ugcugccucc ccaut                              35

<210> SEQ ID NO 33
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl A
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
```

```
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-O-methyl U
<220> FEATURE:
<221> NAME/KEY: modified_base
<222> LOCATION: (29)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl U
<220> FEATURE:
<221> NAME/KEY: modified_base
<222> LOCATION: (35)..(35)
```

-continued

```
<223> OTHER INFORMATION: inverted 2'H T

<400> SEQUENCE: 33
auggggacua uaccgcguaa ugcugccucc ccaut                         35

<210> SEQ ID NO 34
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-Fluoro U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
```

<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-Fluoro C
<220> FEATURE:
<221> NAME/KEY: modified_base
<222> LOCATION: (31)..(31)
<223> OTHER INFORMATION: 2'-Fluoro U
<220> FEATURE:
<221> NAME/KEY: modified_base
<222> LOCATION: (32)..(32)
<223> OTHER INFORMATION: 2'-Fluoro C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-Fluoro C
<220> FEATURE:
<221> NAME/KEY: modified_base
<222> LOCATION: (35)..(35)
<223> OTHER INFORMATION: inverted 2'H T

<400> SEQUENCE: 34
gugaggacua uaccgcguaa ugcugccucc ucact                35

<210> SEQ ID NO 35
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-Fluoro U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)

-continued

```
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
```

```
<223> OTHER INFORMATION: 2'-Fluoro U
<220> FEATURE:
<221> NAME/KEY: modified_base
<222> LOCATION: (29)..(30)
<223> OTHER INFORMATION: 2'-Fluoro C
<220> FEATURE:
<221> NAME/KEY: modified_base
<222> LOCATION: (31)..(31)
<223> OTHER INFORMATION: 2'-Fluoro U
<220> FEATURE:
<221> NAME/KEY: modified_base
<222> LOCATION: (32)..(32)
<223> OTHER INFORMATION: 2'-Fluoro C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-Fluoro C
<220> FEATURE:
<221> NAME/KEY: modified_base
<222> LOCATION: (35)..(35)
<223> OTHER INFORMATION: inverted 2'H T

<400> SEQUENCE: 35
gugaggacua uaccgcguaa ugcugccucc ucact                                35

<210> SEQ ID NO 36
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
```

```
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 36
```
gugaggacua uaccgcguaa ugcugccucc ucact        35

<210> SEQ ID NO 37
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)

```
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-O-methyl U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 37
gugaggacua uaccgcguaa ugcugccucc ucact                                35

<210> SEQ ID NO 38
<211> LENGTH: 29
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(3)
<223> OTHER INFORMATION: 2'-O-methyl G
<220> FEATURE:
<221> NAME/KEY: misc_feature
<222> LOCATION: (4)..(4)
<223> OTHER INFORMATION: RNA 2'OH
<220> FEATURE:
<221> NAME/KEY: modified_base
<222> LOCATION: (5)..(5)
<223> OTHER INFORMATION: 2'-Fluoro C
<220> FEATURE:
<221> NAME/KEY: modified_base
<222> LOCATION: (6)..(6)
<223> OTHER INFORMATION: 2'-Fluoro U
<220> FEATURE:
<221> NAME/KEY: modified_base
<222> LOCATION: (7)..(7)
```

```
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(11)
<223> OTHER INFORMATION: 2'-Fluoro C
<220> FEATURE:
<221> NAME/KEY: misc_feature
<222> LOCATION: (12)..(12)
<223> OTHER INFORMATION: RNA 2'OH
<220> FEATURE:
<221> NAME/KEY: modified_base
<222> LOCATION: (13)..(13)
<223> OTHER INFORMATION: 2'-Fluoro C
<220> FEATURE:
<221> NAME/KEY: misc_feature
<222> LOCATION: (14)..(14)
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro U
<220> FEATURE:
<221> NAME/KEY: misc_feature
<222> LOCATION: (16)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(24)
<223> OTHER INFORMATION: 2'-Fluoro C
<220> FEATURE:
<221> NAME/KEY: modified_base
<222> LOCATION: (25)..(25)
<223> OTHER INFORMATION: 2'-Fluoro U
<220> FEATURE:
<221> NAME/KEY: modified_base
<222> LOCATION: (26)..(28)
<223> OTHER INFORMATION: 2'-O-methyl C
<220> FEATURE:
<221> NAME/KEY: modified_base
<222> LOCATION: (29)..(29)
<223> OTHER INFORMATION: inverted 2'H

<400> SEQUENCE: 38
gggacuauac cgcguaaugc ugccuccct                                           29

<210> SEQ ID NO 39
<211> LENGTH: 31
<212> TYPE: DNA
<213> ORGANISM: Artificial Sequence
<220> FEATURE:
```

-continued

```
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl g
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl g
<220> FEATURE:
<221> NAME/KEY: misc_feature
<222> LOCATION: (5)..(5)
<223> OTHER INFORMATION: RNA 2'OH
<220> FEATURE:
<221> NAME/KEY: modified_base
<222> LOCATION: (6)..(6)
<223> OTHER INFORMATION: 2'-Fluoro C
<220> FEATURE:
<221> NAME/KEY: modified_base
<222> LOCATION: (7)..(7)
<223> OTHER INFORMATION: 2'-Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'-Fluoro C
<220> FEATURE:
<221> NAME/KEY: misc_feature
<222> LOCATION: (13)..(13)
<223> OTHER INFORMATION: RNA 2'OH
<220> FEATURE:
<221> NAME/KEY: modified_base
<222> LOCATION: (14)..(14)
<223> OTHER INFORMATION: 2'-Fluoro C
<220> FEATURE:
<221> NAME/KEY: modified_base
<222> LOCATION: (16)..(16)
<223> OTHER INFORMATION: 2'-Fluoro U
<220> FEATURE:
<221> NAME/KEY: misc_feature
<222> LOCATION: (17)..(18)
<223> OTHER INFORMATION: RNA 2'OH
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: misc_feature
<222> LOCATION: (20)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro C
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
```

```
<223> OTHER INFORMATION: 2'-Fluoro C
<220> FEATURE:
<221> NAME/KEY: modified_base
<222> LOCATION: (26)..(26)
<223> OTHER INFORMATION: 2'-Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H

<400> SEQUENCE: 39
guggacuaua ccgcguaaug cugccuccac t                              31

<210> SEQ ID NO 40
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl A
<220> FEATURE:
<221> NAME/KEY: modified_base
<222> LOCATION: (3)..(3)
<223> OTHER INFORMATION: 2'-O-methyl U
<220> FEATURE:
<221> NAME/KEY: modified_base
<222> LOCATION: (4)..(5)
<223> OTHER INFORMATION: 2'-O-methyl G
<220> FEATURE:
<221> NAME/KEY: misc_feature
<222> LOCATION: (6)..(6)
<223> OTHER INFORMATION: RNA 2'OH
<220> FEATURE:
<221> NAME/KEY: modified_base
<222> LOCATION: (7)..(7)
<223> OTHER INFORMATION: 2'-Fluoro C
<220> FEATURE:
<221> NAME/KEY: modified_base
<222> LOCATION: (8)..(8)
<223> OTHER INFORMATION: 2'-Fluoro U
<220> FEATURE:
<221> NAME/KEY: modified_base
<222> LOCATION: (9)..(9)
<223> OTHER INFORMATION: 2'-O-methyl A
<220> FEATURE:
<221> NAME/KEY: modified_base
<222> LOCATION: (10)..(10)
<223> OTHER INFORMATION: 2'-Fluoro U
<220> FEATURE:
<221> NAME/KEY: modified_base
<222> LOCATION: (11)..(11)
<223> OTHER INFORMATION: 2'-O-methyl A
<220> FEATURE:
<221> NAME/KEY: modified_base
<222> LOCATION: (12)..(13)
<223> OTHER INFORMATION: 2'-Fluoro C
<220> FEATURE:
<221> NAME/KEY: misc_feature
<222> LOCATION: (14)..(14)
```

```
<223> OTHER INFORMATION: RNA 2'OH
<220> FEATURE:
<221> NAME/KEY: modified_base
<222> LOCATION: (15)..(15)
<223> OTHER INFORMATION: 2'-Fluoro C
<220> FEATURE:
<221> NAME/KEY: misc_feature
<222> LOCATION: (16)..(16)
<223> OTHER INFORMATION: RNA 2'OH
<220> FEATURE:
<221> NAME/KEY: modified_base
<222> LOCATION: (17)..(17)
<223> OTHER INFORMATION: 2'-Fluoro U
<220> FEATURE:
<221> NAME/KEY: misc_feature
<222> LOCATION: (18)..(19)
<223> OTHER INFORMATION: RNA 2'OH
<220> FEATURE:
<221> NAME/KEY: modified_base
<222> LOCATION: (20)..(20)
<223> OTHER INFORMATION: 2'-Fluoro U
<220> FEATURE:
<221> NAME/KEY: misc_feature
<222> LOCATION: (21)..(21)
<223> OTHER INFORMATION: RNA 2'OH
<220> FEATURE:
<221> NAME/KEY: modified_base
<222> LOCATION: (22)..(22)
<223> OTHER INFORMATION: 2'-Fluoro C
<220> FEATURE:
<221> NAME/KEY: modified_base
<222> LOCATION: (23)..(23)
<223> OTHER INFORMATION: 2'-Fluoro U
<220> FEATURE:
<221> NAME/KEY: misc_feature
<222> LOCATION: (24)..(24)
<223> OTHER INFORMATION: RNA 2'OH
<220> FEATURE:
<221> NAME/KEY: modified_base
<222> LOCATION: (25)..(26)
<223> OTHER INFORMATION: 2'-Fluoro C
<220> FEATURE:
<221> NAME/KEY: modified_base
<222> LOCATION: (27)..(27)
<223> OTHER INFORMATION: 2'-Fluoro U
<220> FEATURE:
<221> NAME/KEY: modified_base
<222> LOCATION: (28)..(29)
<223> OTHER INFORMATION: 2'-O-methyl C
<220> FEATURE:
<221> NAME/KEY: modified_base
<222> LOCATION: (30)..(30)
<223> OTHER INFORMATION: 2'-O-methyl A
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 40
gauggacuau accgcguaau gcugccucca uct                                  33

<210> SEQ ID NO 41
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
```

-continued

```
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
```

-continued

```
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 41
gugaggacua uaccgcguaa ugcugccucc ucact                              35

<210> SEQ ID NO 42
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
```

```
-continued

<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: misc_feature
<222> LOCATION: (19)..(20)
<223> OTHER INFORMATION: RNA 2'OH
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: misc_feature
<222> LOCATION: (22)..(22)
<223> OTHER INFORMATION: RNA 2'OH
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
```

```
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 42
gugaggacua uaccgcguaa ugcugccucc ucact                                35

<210> SEQ ID NO 43
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
```

```
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 43
gugaggacua uaccgcguaa ugcugccucc ucact                          35

<210> SEQ ID NO 44
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
```

```
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: modified_base
<222> LOCATION: (25)..(25)
```

```
<223> OTHER INFORMATION: 2'-O-methyl G
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 44
gugaggacua uaccgcguaa ugcugccucc ucact                           35

<210> SEQ ID NO 45
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
```

```
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
```

```
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 45
gugaggacua uaccgcguaa ugcugccucc ucact                      35

<210> SEQ ID NO 46
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl A
<220> FEATURE:
<221> NAME/KEY: misc_feature
<222> LOCATION: (18)..(18)
```

```
<223> OTHER INFORMATION: RNA 2'OH
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: misc_feature
<222> LOCATION: (21)..(21)
<223> OTHER INFORMATION: RNA 2'OH
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl U
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 46
gugaggacua uaccgcaauc gugccuccuc act                         33

<210> SEQ ID NO 47
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
```

-continued

```
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'Fluoro C
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'Fluoro C
<220> FEATURE:
<221> NAME/KEY: modified_base
<222> LOCATION: (21)..(21)
<223> OTHER INFORMATION: 2'-O-methyl G
<220> FEATURE:
<221> NAME/KEY: modified_base
<222> LOCATION: (22)..(22)
<223> OTHER INFORMATION: 2'Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
```

```
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl U
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 47
gugaggacua uaccgcaauc gugccuccuc act                                  33

<210> SEQ ID NO 48
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
```

```
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: modified_base
<222> LOCATION: (21)..(21)
<223> OTHER INFORMATION: 2'-O-methyl G
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(25)
<223> OTHER INFORMATION: 2'-Fluoro C
<220> FEATURE:
<221> NAME/KEY: modified_base
<222> LOCATION: (26)..(26)
<223> OTHER INFORMATION: 2'-Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl U
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 48
gugaggacua uaccgcaauc gugccuccuc act                                    33

<210> SEQ ID NO 49
<211> LENGTH: 33
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
```

-continued

```
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: misc_feature
<222> LOCATION: (7)..(7)
<223> OTHER INFORMATION: RNA 2'OH
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'-Fluoro U
<220> FEATURE:
<221> NAME/KEY: modified_base
<222> LOCATION: (20)..(20)
<223> OTHER INFORMATION: 2'-Fluoro C
<220> FEATURE:
<221> NAME/KEY: modified_base
<222> LOCATION: (21)..(21)
<223> OTHER INFORMATION: 2'-O-methyl G
<220> FEATURE:
<221> NAME/KEY: modified_base
<222> LOCATION: (22)..(22)
<223> OTHER INFORMATION: 2'-Fluoro U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(25)
```

```
<223> OTHER INFORMATION: 2'-Fluoro C
<220> FEATURE:
<221> NAME/KEY: modified_base
<222> LOCATION: (26)..(26)
<223> OTHER INFORMATION: 2'-Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl U
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl A
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: inverted 2'H T

<400> SEQUENCE: 49
gugaggacua uaccgcaauc gugccuccuc act                                      33

<210> SEQ ID NO 50
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-Methyl-A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'Fluoro U
<220> FEATURE:
<221> NAME/KEY: misc_feature
<222> LOCATION: (10)..(10)
<223> OTHER INFORMATION: 2'-O-methyl A
<220> FEATURE:
<221> NAME/KEY: modified_base
<222> LOCATION: (11)..(11)
```

-continued

```
<223> OTHER INFORMATION: 2'Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: misc_feature
<222> LOCATION: (17)..(17)
<223> OTHER INFORMATION: RNA 2'OH
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'Fluoro U
<220> FEATURE:
<221> NAME/KEY: misc_feature
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
```

-continued

<223> OTHER INFORMATION: inverted 2'H T

<400> SEQUENCE: 50
gugaggacua uaccgcguaa ugcugccucc ucact                                    35

<210> SEQ ID NO 51
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-O-methyl C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)

```
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-O-methyl U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(26)
<223> OTHER INFORMATION: 2'-O-methyl C
<220> FEATURE:
<221> NAME/KEY: modified_base
<222> LOCATION: (27)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 51
gugaggacua uaccgcguaa ugcugccucc ucact                        35

<210> SEQ ID NO 52
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
```

```
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'Fluoro C
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-O-methyl C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'Fluoro C
<220> FEATURE:
<221> NAME/KEY: modified_base
<222> LOCATION: (24)..(24)
<223> OTHER INFORMATION: 2'Fluoro U
<220> FEATURE:
<221> NAME/KEY: modified_base
<222> LOCATION: (25)..(25)
<223> OTHER INFORMATION: 2'-O-methyl G
<220> FEATURE:
<221> NAME/KEY: modified_base
<222> LOCATION: (26)..(27)
```

```
<223> OTHER INFORMATION: 2'Fluoro C
<220> FEATURE:
<221> NAME/KEY: modified_base
<222> LOCATION: (28)..(28)
<223> OTHER INFORMATION: 2'Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 52
gugaggacua uaccgcguaa ugcugccucc ucact                              35

<210> SEQ ID NO 53
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'-Fluoro C
<220> FEATURE:
<221> NAME/KEY: modified_base
<222> LOCATION: (9)..(9)
<223> OTHER INFORMATION: 2'-Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
```

-continued

```
<223> OTHER INFORMATION: 2'-Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'-Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'-Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'-Fluoro U
<220> FEATURE:
<221> NAME/KEY: modified_base
<222> LOCATION: (19)..(20)
<223> OTHER INFORMATION: 2'-O-methyl A
<220> FEATURE:
<221> NAME/KEY: modified_base
<222> LOCATION: (21)..(21)
<223> OTHER INFORMATION: 2'-Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'-Fluoro C
<220> FEATURE:
<221> NAME/KEY: modified_base
<222> LOCATION: (24)..(24)
<223> OTHER INFORMATION: 2'-Fluoro U
<220> FEATURE:
<221> NAME/KEY: misc_feature
<222> LOCATION: (25)..(25)
<223> OTHER INFORMATION: RNA s'OH
<220> FEATURE:
<221> NAME/KEY: modified_base
<222> LOCATION: (26)..(27)
<223> OTHER INFORMATION: 2'-Fluoro C
<220> FEATURE:
<221> NAME/KEY: modified_base
<222> LOCATION: (28)..(28)
<223> OTHER INFORMATION: 2'-Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
```

<223> OTHER INFORMATION: inverted 2'H T

<400> SEQUENCE: 53
gugaggacua uaccgcguaa ugcugccucc ucact          35

<210> SEQ ID NO 54
<211> LENGTH: 35
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(3)
<223> OTHER INFORMATION: 2'-O-methyl G
<220> FEATURE:
<221> NAME/KEY: modified_base
<222> LOCATION: (4)..(4)
<223> OTHER INFORMATION: 2'-O-methyl A
<220> FEATURE:
<221> NAME/KEY: modified_base
<222> LOCATION: (5)..(6)
<223> OTHER INFORMATION: 2'-O-methyl G
<220> FEATURE:
<221> NAME/KEY: modified_base
<222> LOCATION: (7)..(7)
<223> OTHER INFORMATION: 2'-O-methyl A
<220> FEATURE:
<221> NAME/KEY: modified_base
<222> LOCATION: (8)..(8)
<223> OTHER INFORMATION: 2'Fluoro C
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(11)
<223> OTHER INFORMATION: 2'Fluoro U
<220> FEATURE:
<221> NAME/KEY: modified_base
<222> LOCATION: (12)..(12)
<223> OTHER INFORMATION: 2'-O-methyl A
<220> FEATURE:
<221> NAME/KEY: modified_base
<222> LOCATION: (13)..(14)
<223> OTHER INFORMATION: 2'Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'Fluoro C
<220> FEATURE:
<221> NAME/KEY: modified_base
<222> LOCATION: (17)..(17)
<223> OTHER INFORMATION: 2'-O-methyl G
<220> FEATURE:
<221> NAME/KEY: modified_base
<222> LOCATION: (18)..(18)
<223> OTHER INFORMATION: 2'Fluoro U
<220> FEATURE:
<221> NAME/KEY: modified_base
<222> LOCATION: (19)..(20)

```
<223> OTHER INFORMATION: 2'-O-methyl A
<220> FEATURE:
<221> NAME/KEY: modified_base
<222> LOCATION: (21)..(21)
<223> OTHER INFORMATION: 2'Fluoro U
<220> FEATURE:
<221> NAME/KEY: modified_base
<222> LOCATION: (22)..(22)
<223> OTHER INFORMATION: 2'-O-methyl G
<220> FEATURE:
<221> NAME/KEY: modified_base
<222> LOCATION: (23)..(23)
<223> OTHER INFORMATION: 2'Fluoro C
<220> FEATURE:
<221> NAME/KEY: modified_base
<222> LOCATION: (24)..(24)
<223> OTHER INFORMATION: 2'-O-methyl U
<220> FEATURE:
<221> NAME/KEY: misc_feature
<222> LOCATION: (25)..(25)
<223> OTHER INFORMATION: RNA 2'OH
<220> FEATURE:
<221> NAME/KEY: modified_base
<222> LOCATION: (26)..(26)
<223> OTHER INFORMATION: 2'-O-methyl C
<220> FEATURE:
<221> NAME/KEY: modified_base
<222> LOCATION: (27)..(27)
<223> OTHER INFORMATION: 2'Fluoro C
<220> FEATURE:
<221> NAME/KEY: modified_base
<222> LOCATION: (28)..(28)
<223> OTHER INFORMATION: 2'Fluoro U
<220> FEATURE:
<221> NAME/KEY: modified_base
<222> LOCATION: (29)..(30)
<223> OTHER INFORMATION: 2'-O-methyl C
<220> FEATURE:
<221> NAME/KEY: modified_base
<222> LOCATION: (31)..(31)
<223> OTHER INFORMATION: 2'-O-methyl U
<220> FEATURE:
<221> NAME/KEY: modified_base
<222> LOCATION: (32)..(32)
<223> OTHER INFORMATION: 2'-O-methyl C
<220> FEATURE:
<221> NAME/KEY: modified_base
<222> LOCATION: (33)..(33)
<223> OTHER INFORMATION: 2'-O-methyl A
<220> FEATURE:
<221> NAME/KEY: modified_base
<222> LOCATION: (34)..(34)
<223> OTHER INFORMATION: 2'-O-methyl C
<220> FEATURE:
<221> NAME/KEY: modified_base
<222> LOCATION: (35)..(35)
<223> OTHER INFORMATION: inverted 2'H T

<400> SEQUENCE: 54
gugaggacua uaccgcguaa ugcugccucc ucact                                35

<210> SEQ ID NO 55
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
```

```
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
```

```
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 55
guggacuaua ccgcguaaug cugccuccac t                            31

<210> SEQ ID NO 56
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
```

-continued

```
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'-O-methyl U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(24)
<223> OTHER INFORMATION: 2'-O-methyl C
<220> FEATURE:
<221> NAME/KEY: modified_base
<222> LOCATION: (25)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 56
guggacuaua ccgcguaaug cugccuccac t                              31

<210> SEQ ID NO 57
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
```

```
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: misc_feature
<222> LOCATION: (15)..(15)
<223> OTHER INFORMATION: RNA 2'OH
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'Fluoro U
<220> FEATURE:
<221> NAME/KEY: modified_base
<222> LOCATION: (23)..(23)
<223> OTHER INFORMATION: 2'-O-methyl G
<220> FEATURE:
<221> NAME/KEY: modified_base
<222> LOCATION: (24)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
```

-continued

```
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 57
guggacuaua ccgcguaaug cugccuccac t                            31

<210> SEQ ID NO 58
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
```

```
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'Fluoro U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 58
guggacuaua ccgcguaaug cugccuccac t                              31

<210> SEQ ID NO 59
<211> LENGTH: 31
<212> TYPE: DNA
<213> ORGANISM: Artificial Sequence
<220> FEATURE:
<223> OTHER INFORMATION: Synthetic aptamer
<220> FEATURE:
<221> NAME/KEY: modified_base
<222> LOCATION: (1)..(1)
<223> OTHER INFORMATION: 2'-O-methyl G
<220> FEATURE:
<221> NAME/KEY: modified_base
<222> LOCATION: (2)..(2)
<223> OTHER INFORMATION: 2'-O-methyl U
<220> FEATURE:
<221> NAME/KEY: modified_base
<222> LOCATION: (3)..(4)
<223> OTHER INFORMATION: 2'-O-methyl G
<220> FEATURE:
<221> NAME/KEY: modified_base
<222> LOCATION: (5)..(5)
<223> OTHER INFORMATION: 2'-O-methyl A
<220> FEATURE:
<221> NAME/KEY: modified_base
<222> LOCATION: (6)..(6)
<223> OTHER INFORMATION: 2'Fluoro C
<220> FEATURE:
<221> NAME/KEY: modified_base
<222> LOCATION: (7)..(7)
```

-continued

```
<223> OTHER INFORMATION: 2'Fluoro U
<220> FEATURE:
<221> NAME/KEY: modified_base
<222> LOCATION: (8)..(8)
<223> OTHER INFORMATION: 2'-O-methyl A
<220> FEATURE:
<221> NAME/KEY: modified_base
<222> LOCATION: (9)..(9)
<223> OTHER INFORMATION: 2'Fluoro U
<220> FEATURE:
<221> NAME/KEY: modified_base
<222> LOCATION: (10)..(10)
<223> OTHER INFORMATION: 2'-O-methyl A
<220> FEATURE:
<221> NAME/KEY: modified_base
<222> LOCATION: (11)..(12)
<223> OTHER INFORMATION: 2'Fluoro C
<220> FEATURE:
<221> NAME/KEY: modified_base
<222> LOCATION: (13)..(13)
<223> OTHER INFORMATION: 2'-O-methyl G
<220> FEATURE:
<221> NAME/KEY: modified_base
<222> LOCATION: (14)..(14)
<223> OTHER INFORMATION: 2'Fluoro C
<220> FEATURE:
<221> NAME/KEY: modified_base
<222> LOCATION: (15)..(15)
<223> OTHER INFORMATION: 2'-O-methyl G
<220> FEATURE:
<221> NAME/KEY: modified_base
<222> LOCATION: (16)..(16)
<223> OTHER INFORMATION: 2'Fluoro U
<220> FEATURE:
<221> NAME/KEY: modified_base
<222> LOCATION: (17)..(18)
<223> OTHER INFORMATION: 2'-O-methyl A
<220> FEATURE:
<221> NAME/KEY: modified_base
<222> LOCATION: (19)..(19)
<223> OTHER INFORMATION: 2'Fluoro U
<220> FEATURE:
<221> NAME/KEY: modified_base
<222> LOCATION: (20)..(20)
<223> OTHER INFORMATION: 2'-O-methyl G
<220> FEATURE:
<221> NAME/KEY: modified_base
<222> LOCATION: (21)..(21)
<223> OTHER INFORMATION: 2'Fluoro C
<220> FEATURE:
<221> NAME/KEY: modified_base
<222> LOCATION: (22)..(22)
<223> OTHER INFORMATION: 2'-O-methyl U
<220> FEATURE:
<221> NAME/KEY: misc_feature
<222> LOCATION: (23)..(23)
<223> OTHER INFORMATION: RNA 2'OH
<220> FEATURE:
<221> NAME/KEY: modified_base
<222> LOCATION: (24)..(24)
<223> OTHER INFORMATION: 2'-O-methyl C
<220> FEATURE:
<221> NAME/KEY: modified_base
<222> LOCATION: (25)..(25)
<223> OTHER INFORMATION: 2'Fluoro C
<220> FEATURE:
<221> NAME/KEY: modified_base
<222> LOCATION: (26)..(26)
<223> OTHER INFORMATION: 2'Fluoro U
<220> FEATURE:
<221> NAME/KEY: modified_base
<222> LOCATION: (27)..(28)
<223> OTHER INFORMATION: 2'-O-methyl C
<220> FEATURE:
<221> NAME/KEY: modified_base
<222> LOCATION: (29)..(29)
<223> OTHER INFORMATION: 2'-O-methyl A
<220> FEATURE:
<221> NAME/KEY: modified_base
<222> LOCATION: (30)..(30)
```

```
<223> OTHER INFORMATION: 2'-O-methyl C
<220> FEATURE:
<221> NAME/KEY: modified_base
<222> LOCATION: (31)..(31)
<223> OTHER INFORMATION: inverted 2'H T

<400> SEQUENCE: 59
guggacuaua ccgcguaaug cugccuccac t                                31
```

MODULATORS OF COAGULATION FACTORS

CROSS REFERENCE TO RELATED APPLICATIONS

This application is a continuation of U.S. patent application Ser. No. 11/821,183 filed Jun. 22, 2007 now U.S. Pat. No. 7,723,315, allowed, which is a divisional of U.S. patent application Ser. No. 11/113,378 filed Apr. 22, 2005, now U.S. Pat. No. 7,304,041, which claims the benefit of priority to U.S. Provisional Patent Application No. 60/564,873 filed Apr. 22, 2004, all of which are all incorporated herein by reference in their entirety.

FIELD OF INVENTION

The invention is an improved agent, composition and method to regulate the pharmacological activity of a coagulation factor with nucleic acid ligands (e.g., aptamers).

BACKGROUND OF THE INVENTION

Despite substantial efforts to treat and prevent thrombotic events, arterial thrombosis continues to be the major cause of death in adult populations of developed nations. Although numerous medical strategies exist for treating thrombosis, no available agent meets the therapeutic endpoints of both bioavailability and efficacy, while also having a reasonable safety profile (see Feuerstein et al. (1999) *Arterioscler. Thromb. Vasc. Biol.* 19:2554-2562).

Under normal circumstances, an injury to vascular endothelial cells lining a blood vessel triggers a hemostatic response through a sequence of events commonly referred to as the coagulation "cascade." The cascade culminates in the conversion of soluble fibrinogen to insoluble fibrin which, together with platelets, forms a localized clot or thrombus which prevents extravascular release of blood components. Wound healing can then occur followed by clot dissolution and restoration of blood vessel integrity and flow.

Initiation of blood coagulation arises from two distinct pathways: the intrinsic and extrinsic pathways. The intrinsic pathway can be triggered in vitro by contact of blood borne factors with artificial negatively charged surfaces such as glass. In contrast, the extrinsic pathway can be initiated in vivo or in vitro when tissue factor (TF), normally sequestered from the circulatory system, comes into contact with blood after injury. Blood exposed TF acts as a cofactor for the factor VIIa ("FVIIa") catalyzed activation of factor IX ("FIX") and factor X ("FX"). This leads to rapid formation of FXa and thrombin, which subsequently polymerizes to form the fibrin clot. Both the intrinsic and extrinsic pathways are characterized by the assembly of multiple protein complexes on procoagulant surfaces, which localizes the response to the site of injury (see Mann, K. G. et al. (1990) *Blood* 76:1).

Anticoagulant Therapy

Coumarin drugs, such as warfarin as well as the glycosaminoglycans, heparin and heparan sulfate, are commonly used as anticoagulants. Warfarin, a coumarin derivative, acts by competing with vitamin K dependent post-translational modification of prothrombin and other vitamin K-dependent clotting factors. Its action is somewhat slower and longer lasting effect than heparin. The coumarin drugs inhibit coagulation by inhibiting the vitamin K-dependent carboxylation reactions necessary to the function of thrombin, and factors VII, IX, and X as well as proteins C and S. These drugs act by inhibiting the reduction of the quinone derivatives of vitamin K to their active hydroquinone forms. Because of the mode of action of coumarin drugs, it takes several days for their maximum effect to be realized. Heparin binds to, and activates, antithrombin III which then inhibits the serine proteases of the coagulation cascade. In part due to their potency, heparin and LMW heparin suffer drawbacks. Uncontrolled bleeding is a major complication observed in up to 7% of patients receiving continuous infusion up to 14% of patients given intermittent bolus doses. The therapeutic range to achieve efficacy without placing the patient at risk for bleeding is narrow, approximately 1 to less than 3 ug heparin/ml plasma. At concentrations greater than 4 ug/ml of heparin, clotting activity is not detectable. Thus, great care must be taken to keep the patient's plasma concentrations within the therapeutic range.

Groups have used antibodies to coagulation factors to regulate the coagulation cascade. For example PCT Publication No. WO 03/093422 to Schering Aktiengesellschaft discloses antibodies that bind with greater affinity to the factor VIIa/tissue factor (FVIIa/TF) complex than to tissue factor (TF) alone. These antibodies allegedly do not compete for binding to tissue factor with Factor VII and Factor X, and inhibit FX activation.

U.S. Pat. No. 6,001,820 to Hamilton Civic Hospitals Research Development Inc. provides heparin cofactor II specific catalytic agents which are capable of (1) selectively inactivating thrombin which is bound either to fibrin in a clot or to some other surface, but which has only minimal inhibitory activity against free thrombin; (2) inhibiting the assembly of the intrinsic tenase complex and thereby the activation of Factor X by Factor IXa; and (3) inhibiting the activation of Factor IX by Factor XIa.

Aptamers

Nucleic acids have conventionally been thought of as primarily playing an informational role in biological processes. In the past decade it has become clear that the three dimensional structure of nucleic acids can give them the capacity to interact with and regulate proteins. Such nucleic acid ligands or "aptamers" are short DNA or RNA oligomers which can bind to a given ligand with high affinity and specificity. As a class, the three dimensional structures of aptamers are sufficiently variable to allow aptamers to bind to and act as ligands for virtually any chemical compound, whether monomeric or polymeric. Aptamers have emerged as promising new diagnostic and therapeutic compounds, particularly in cancer therapy and the regulation of blood coagulation.

Nucleic acid ligands can be identified through methods related to a method termed the Systematic Evolution of Ligands by EXponential enrichment (SELEX). SELEX involves selection of protein-binding nucleic acids from a mixture of candidate oligonucleotides and step-wise iterations of binding, partitioning and amplification to achieve the desired criterion of binding affinity and selectivity. The SELEX process was first described by Gold and Tuerk in U.S. Pat. No. 5,475,096, and thereafter in U.S. Pat. No. 5,270,163 (see also WO 91/19813; Tuerk et al. (1990) *Science* 249:505-10).

A number of third parties have applied for and secured patents covering the identification, manufacture and use of aptamers. As stated above, Gold and Tuerk are generally credited with first developing the SELEX method for isolating aptamers, and their method is described in a number of United States patents including U.S. Pat. Nos. 5,670,637, 5,696,249, 5,843,653, 6,110,900, and 5,270,163. Thomas Bruice et al. reported a process for producing aptamers in U.S. Pat. No. 5,686,242, which differs from the original SELEX process reported by Tuerk and Gold because it employs strictly random oligonucleotides during the screening sequence. The oligonucleotides screened in the '242 patent lack the oligonucleotide primers that are present in oligonucleotides screened in the SELEX process.

Several patents to Gold et al. contain claims covering aptamers to thrombin. For example, U.S. Pat. No. 5,670,637 contains claims covering aptamers that bind to proteins. U.S. Pat. No. 5,696,249 claims an aptamer produced by the SELEX process. U.S. Pat. Nos. 5,756,291 and 5,582,981 to O'Toole, disclose and claim a method for detecting thrombin using a labeled aptamer that comprises a defined six nucleotide sequence. U.S. Pat. Nos. 5,476,766 and 6,177,557 disclose compounds and methods to identify nuclei acid ligand solutions to thrombin using SELEX.

Sullenger, Rusconi, Kontos and White in WO 02/26932 describe RNA aptamers that bind to coagulation factors, E2F family transcription factors, Ang1, Ang2, and fragments or peptides thereof, transcription factors, autoimmune antibodies and cell surface receptors useful in the modulation of hemostasis and other biologic events. See also Rusconi et al, Thrombosis and Haemostasis 83:841-848 (2000), White et al, *J. Clin Invest* 106:929-34 (2000), Ishizaki et al, *Nat Med* 2:1386-1389 (1996), and Lee et al, *Nat. Biotechnol.* 15:41-45 (1997)).

Modulation of Aptamers

PCT Publication No. WO 02/096926 to Duke University describes agents and methods to modulate the biological activity of nucleic acid ligands through the administration of a modulator. The publication describes aptamers controlled by modulators that can be nucleic acids. The modulatable aptamers are described as being useful in the treatment of diseases in which it is important to inhibit coagulation, elongation factor 2 activity or angiogenesis. The modulatable aptamers to control coagulation include the aptamers to coagulation factors VII or VIIa, VIII or VIIIa, IX or IXa, V or Va, X or Xa, complexes formed with these factors, as well as platelet receptors. The modulator can change the binding of the nucleic acid ligand for its target, degrade or otherwise cleave, metabolize or break down the nucleic acid ligand while the ligand is exerting its effect. Modulators can be administered in real time as needed based on various factors, including the progress of the patient, as well as the physician's discretion in how to achieve optimal therapy.

Maximizing Utility of Aptamers

In order for aptamers to be useful therapeutic reagents, they should bind tightly to proteins, inhibit a specified function of that protein if an antagonist is desired and have no harmful side-effects. Unmodified RNA is not realistically used as a therapeutic agent since blood is rich in ribonucleases. Some modification of single-stranded RNA and DNA can produce molecules which are stable in blood and certain known aptamers have 2'F or 2'NH$_2$ groups within each pyrimidine nucleotide.

However, there is no way to predict how a particular modification changes aptamers. In particular, when additional limitations are required, as is the case with modulatable aptamers, no techniques exist to predict how one or more modifications can affect the capacity of the aptamer to regulate its ligands and at the same time continue to be regulated by antidote binding.

The successful use of aptamers as therapeutic agents depends not only on their efficacy and specificity, but also on economics. Extrapolating from the most successful animal experiments of currently available aptamers, an aptamer dose of 1-2 mg/kg body wt is usually an effective dose (derived from experiments on aptamers inhibiting VEGF, PDGF, L-selectin, and P-selectin). For a 70-kg adult, this means that each injected dose would be 70-140 mg. For acute indications, such as organ transplant, myocardial infarcts, toxic or septic shock, angioplasty, or pulmonary embolism treatment every 3 days for 15 days would involve $700-$1400 in cost of goods. Clearly, for chronic indications, the cost of the goods is an issue. There is thus a need to reduce the cost of manufacturing of aptamers.

Several methods have been developed that modify the base SELEX process to obtain modified aptamers. For example, patents disclose the use of modified nucleotides in the SELEX process to obtain aptamers that exhibit improved properties. U.S. Pat. No. 5,660,985 provides 2'-modified nucleotides that allegedly display enhanced in vivo stability. U.S. Pat. No. 6,083,696 discloses a "blended" SELEX process in which oligonucleotides covalently linked to non-nucleic acid functional units are screened for their capacity to bind a target molecule. Other patents describe post-SELEX modifications to aptamers to decrease their size, increase their stability, or increase target binding affinity (see, e.g., U.S. Pat. Nos. 5,817,785 and 5,648,214).

In U.S. Pat. No. 5,245,022 Weis et al. disclose an oligonucleotide of about 12-25 bases that is terminally substituted by a polyalkyleneglycol. These modified oligonucleotides are reported to be resistant to exonuclease activity.

U.S. Pat. Nos. 5,670,633 and 6,005,087 to Cook et al. describe thermally stable 2'-fluoro oligonucleotides that are complementary to an RNA or DNA base sequence. U.S. Pat. Nos. 6,222,025 and 5,760,202 to Cook et al. describe the synthesis of 2'-O substituted pyrimidines and oligomers containing the modified pyrimidines. EP 0 593 901 B1 discloses oligonucleotide and ribozyme analogues with terminal 3',3'- and 5',5'-nucleoside bonds. U.S. Pat. No. 6,011,020 to Gold et al. discloses and claims an aptamer modified by polyethylene glycol.

Currently, a strong need remains to provide methods and compositions to treat patients in need of anticoagulant therapy, and in particular, during surgery or other medical intervention.

Therefore, it is an object of the present invention to provide methods and compositions to treat patients in need of anticoagulant therapy, and in particular, during surgery or other medical intervention It is another object of the present invention to provide more control over the therapeutic effect, pharmacokinetics and duration of activity of anticoagulant therapies.

SUMMARY OF INVENTION

Improved nucleic acid ligands for anticoagulant therapy are disclosed as well as improved nucleic acid ligands in combination with an antidote that changes the binding of the nucleic acid ligand for its target or that degrades or otherwise cleaves, metabolizes or breaks down the nucleic acid ligand while the ligand is still exerting its effect. These improved aptamers provide favorable anticoagulant properties for in vivo applications, including during human or veterinary surgery. The anticoagulant function of the improved aptamer is conveniently neutralized on administration of its antidote when desired by the surgeon or other medical care specialist.

In one aspect of the invention, improved nucleic acid ligands or aptamers to a factor in the blood coagulation cascade are provided. In some embodiments, the factors include Factor IX (FIX) or the cleavage product Factor IXa (FIXa). In some embodiments, the aptamers are ligands to the complex formed by FIXa with Factor VIIIa (FVIIIa), also known as the "intrinsic tenase complex." In some embodiments, the aptamers are ligands that inhibit the complex formation between FIXa and FVIIIa. In a subembodiment, the aptamers of the present invention bind to the complex of FIX and FVIIIa and inhibit activation of Factor X (FX). The aptamers can interact with FIX, FIXa or a complex formed with FVIIIa in the presence or absence of additional calcium. The aptamers can also interact with the factors of the complex at a cell membrane. In one embodiment, the aptamers bind to the intrinsic tenase complex at the membrane surface.

In another aspect of the invention, the applicants have discovered improved aptamers to gene products of coagulation Factor IX (FIX), and to its cleavage product, Factor IXa (FIXa). In one embodiment, the nucleic acid ligand includes at least one region that binds to another region in the molecule via Watson-Crick base pairing (stem) and at least one region that does not bind to any other regions of the molecule under physiological conditions (loop). In a further embodiment, the nucleic acid ligand includes two stems (stem 1 and stem 2) and two loops (loop 1 and loop 2). Typically, stem 1 is one to fifteen or one to twenty nucleotide pairs long. Stem 1 can also be ten, nine, eight, seven, six, five, four, three or two nucleotides long. In general, stem 2 is one to ten nucleotides long. Stem 2 can also be nine, eight, seven, six, five, four, three or two nucleotides long. The length of loop 1 and loop 2 can also be varied. Loop 2 can be as long as ten nucleotides, but can also be eight or less nucleotides long, including, seven, six, five, four, three or two nucleotides long. The length of loop 1 can also be varied, and in one embodiment includes ten or nince nucleotides in the 5'-3' direction and one nucleotide in the 3'-5' direction.

The aptamers to a Factor IX gene product of the present invention can be comprised of ribonucleotides or deoxyribonucleotides, or a combination thereof. In general, the improved aptamers are at least 25 nucleotides long, and typically not longer than 35-40 nucleotides long. In one embodiment, aptamers are at least 25, 30, 35, or 40 nucleotides in length. In specific embodiments, the sequence of stem 1 includes 5 nucleotides in the 5'-3' direction. In a sub-embodiment, stem 1 includes three guanine (G) residues in the 5'-3' direction.

The improved aptamers can include a "suicide position." In one embodiment, this position becomes single stranded and labile upon binding of the antidote to the improved aptamer and allows for cleavage of the improved aptamer upon binding of the antidote by enzymes in the circulation, such as blood or liver endonucleases, thereby effectively eliminating the active aptamer from circulation. The suicide position can be at a guanine in stem 2 that is hydroxylated. In one embodiment, this nucleotide is in a double stranded configuration until bound with an antidote and becomes single stranded and available for cleavage upon binding of the antidote.

In an embodiment, the aptamers include the nucleotide sequence gugg and the complimentary sequence ccac. In one embodiment, the aptamer to Factor IX comprises the nucleotide sequence: gugga cuauacc gcg uaaugc ugc c uccac t (SeqID 19).

Another embodiment of the invention includes an antidote oligonucleotide paired with the aptamer of the invention. The antidote oligonucleotide can be complementary to at least a portion of the aptamer. The antidote can, for example, comprise the following sequences:

(5'-3') sequence: cgcgguauaguccccau (Apt/AD; SEQ ID NO:1); (5'-3') sequence: cgcgguauaguccc (Apt6/AD; SEQ ID NO:2); (5'-3') sequence: cgcgguauaguccac (Apt7/AD; SEQ ID NO:3); (5'-3') sequence: cgcgguauaguccauc (Apt8/AD; SEQ ID NO:4); (5'-3') sequence: cgcgguauagucag (Apt9/AD; SEQ ID NO:5); (5'-3') sequence: cgcgguauagucagg (Apt10/AD; SEQ ID NO:6); (5'-3') sequence: cgcgguauagucagag (Apt11/AD; SEQ ID NO:7); (5'-3') sequence: cgcgguauaguccucac (Apt14/AD; SEQ ID NO:8), or any modification or derivative thereof. In certain embodiments, the antidote consists essentially of one of the above sequences, or consists entirely of one of the above sequences.

The antidote sequence does not need to be completely complementary to the improved anticoagulant aptamer as long as the antidote sufficiently binds to or hybridizes to the aptamer to neutralize its activity.

The aptamer pairs of the present invention include the following sequences:

| Aptamer | Antidote |
|---|---|
| augggga cuauacc gcg uaaugc ugc c uccccau t (SEQ ID NO: 9) | cgcgguauaguccccau (SEQ ID NO: 1) |
| augggga cuauaccgcguaaugcugcc uccccau t (SEQ ID NO: 10) | cgcgguauaguccccau (SEQ ID NO: 1) |
| ggga cuauaccgcguaaugcugcc uccc t (SEQ ID NO: 11) | cgcgguauaguccc (SEQ ID NO: 2) |
| gugga cuauaccgcguaaugcugcc uccac t (SEQ ID NO: 12) | cgcgguauaguccac (SEQ ID NO: 3) |
| gaugga cuauaccgcguaaugcugcc uccauc t (SEQ ID NO: 13) | cgcgguauaguccauc (SEQ ID NO: 4) |
| cuga cuauaccgcguaaugcugcc ucag t (SEQ ID NO: 14) | cgcgguauagucag (SEQ ID NO: 5) |
| ccuga cuauaccgcguaaugcugcc ucagg t (SEQ ID NO: 15) | cgcgguauagucagg (SEQ ID NO: 6) |
| cucuga cuauaccgcguaaugcugcc ucagag t (SEQ ID NO: 16) | cgcgguauagucagag (SEQ ID NO: 7) |
| gugagga cuauaccgcguaaugcugcc uccucac t (SEQ ID NO: 17) | cgcgguauaguccucac (SEQ ID NO: 8) |

-continued

| Aptamer | Antidote |
|---|---|
| gugagga cuauacc gcg uaaugc ugc c uccucac t (SEQ ID NO: 18) | cgcgguauaguccucac (SEQ ID NO: 8) |
| gugga cuauacc gcg uaaugc ugc c uccac t (SEQ ID NO: 19) | cgcgguauaguccac (SEQ ID NO: 3) |

Improved aptamer-antidote pairs that are more stable and bioactive are developed by including secondary modifications on either the aptamer or antidote or both. In one embodiment, the improved aptamer to Factor IX includes one or more 2'-O-methyl modified nucleotides. In another embodiment, the improved aptamer contains one or more 2'-O-methyl and one or more 2'-fluoro modifications. In another embodiment, the aptamer and antidote contain no 2'-fluoro modifications. In yet another embodiment, the improved aptamer includes one or more 2'-O-methyl and one or more 2'-fluoro modifications on a stem. In one embodiment, at least one guanine in stem 2 of an improved aptamer includes a hydroxyl sugar (2'-OH). In another embodiment, at least one uridine in stem 1 or in stem 2 of the improved aptamer is modified with either a 2'-fluoro or 2'-O-methyl. In another embodiment, at least one cytidine in stem 2 of the improved aptamer is 2'-fluoro modified.

The improved aptamers and antidotes can also include nucleotides that are modified with water-soluble polymers. Such polymers can include a polyethylene glycol, polyamine, polyether, polyanhydride, polyester, or other biodegradable pharmaceutically acceptable polymer.

The invention includes the use of the improved aptamers to bind to FIX, FIXa, or the intrinsic tenase complex. This binding can be in vitro or in vivo. The result of the binding to FIX, FIXa or the tenase complex can be to inhibit the biological activity of the proteins or complex.

In one embodiment, the improved aptamer inhibits blood coagulation by binding to FIXa, which is derived from the same gene product as FIX. The invention includes administering the improved aptamers of the invention to a mammal in need thereof to inhibit blood coagulation. Another embodiment of the invention provides methods of using the improved aptamers and antidotes during a therapeutic regime.

In one embodiment, antidotes to the improved aptamers of the invention are provided to a mammal in need thereof to reverse the anticoagulant effects of the improved aptamers. Improved aptamers and aptamer-antidote pairs can be administered in real time as needed based on various factors, including the progress of the patient, as well as the physician's discretion in how to achieve optimal therapy. Thus, this invention discloses an improved regulatable therapeutic regime in the course of nucleic acid ligand therapy for blood coagulation. In one example, an antidote is provide that neutralizes the effect of the improved aptamer to turn off anticoagulant activity when desired by the physician or other health care provider. In another embodiment, the improved aptamers and antidotes to blood coagulation factors are administered in sequential steps, in which the aptamers are administered, the antidotes are used to limit the activity of the improved aptamers, and subsequently the aptamers are re-administered to a patient in need thereof. In one embodiment, the antidote achieves this neutralization effect by binding to or hybridizing to the improved aptamer.

The improved aptamers can be administered to patients suffering from or at risk of suffering from a cardiovascular disease or intervention, including surgical intervention, that causes or results in a coagulation-inducing event. Examples include acute myocardial infarction (heart attack), cerebrovascular accidents (stroke), ischemia, angioplasty, CABG (coronary artery bypass grafts), cardiopulmonary bypass, thrombosis in the circuit of cardiac bypass apparatus and in patients undergoing renal dialysis, unstable angina, pulmonary embolism, deep vein thrombosis, arterial thrombosis, and disseminated intravascular coagulation.

The improved aptamers can also be administered to prevent coagulation-induced inflammation. It appears that early inflammation is induced by activation of the coagulation cascade. Therefore, the improved aptamers can be used to treat cardiovascular diseases that include a inflammatory component, for example, atherosclerosis, acute coronary syndrome (ACS), myocardial infarction which may result in reperfusion injury, or to treat adverse events associated with post-angioplasty restenosis.

BRIEF DESCRIPTION OF THE DRAWINGS

FIG. 1a is a schematic of aptamers Apt A and 1-5. 1b is a schematic of aptamers 6-11. 1c is a schematic of aptamers Apt 12-17. 1d is a schematic of aptamers Apt 18-20, 1e of Apt 21. 1f is a schematic of aptamers Apt 22-29, 1g of Apt 30-34 and 1h of Apt 35-39.

DETAILED DESCRIPTION

Definitions

Figure 1:
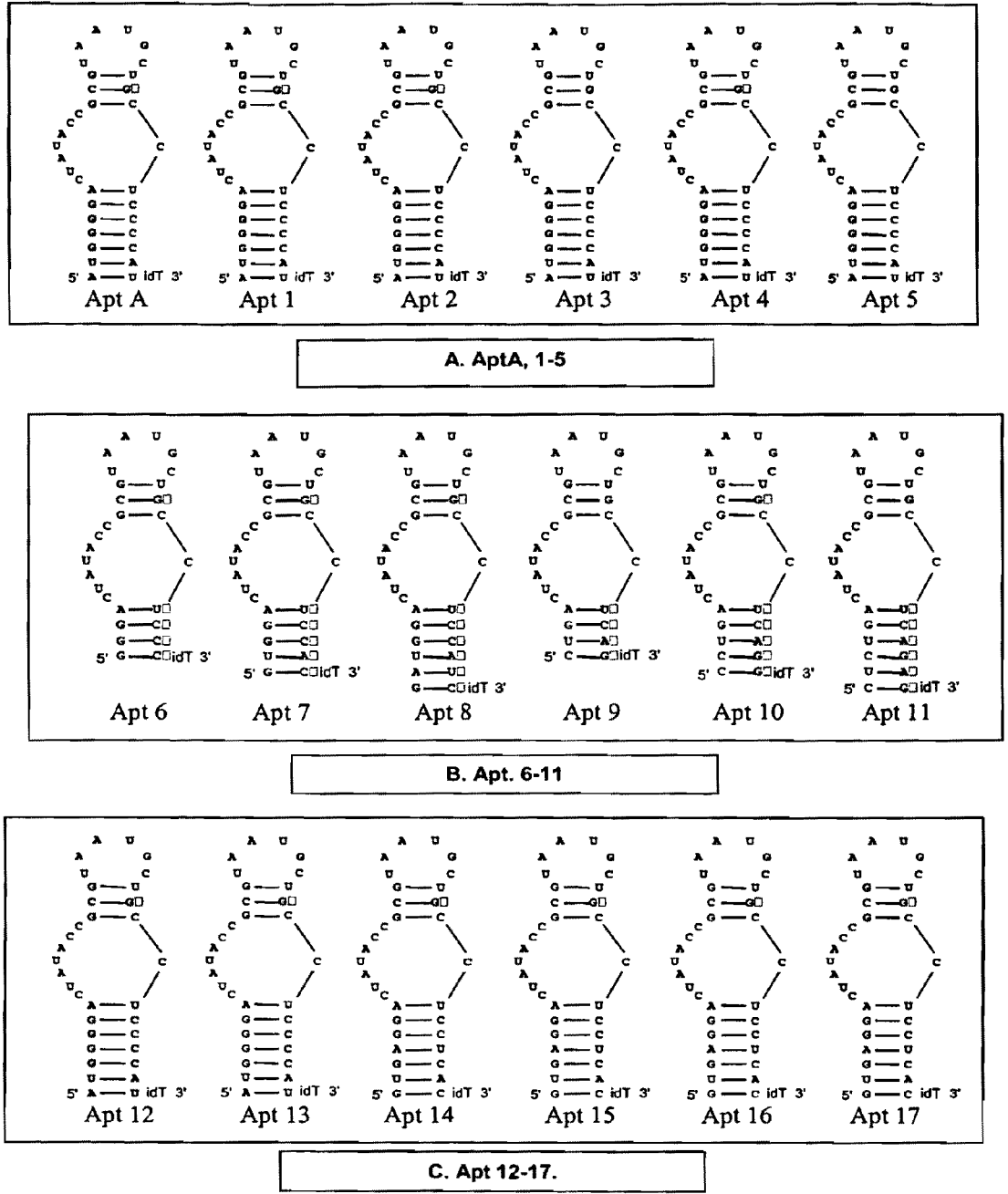
FIG. 1 is a schematic of proposed two dimensional configurations of Apt A, 1-39 described below.
Figure 1:
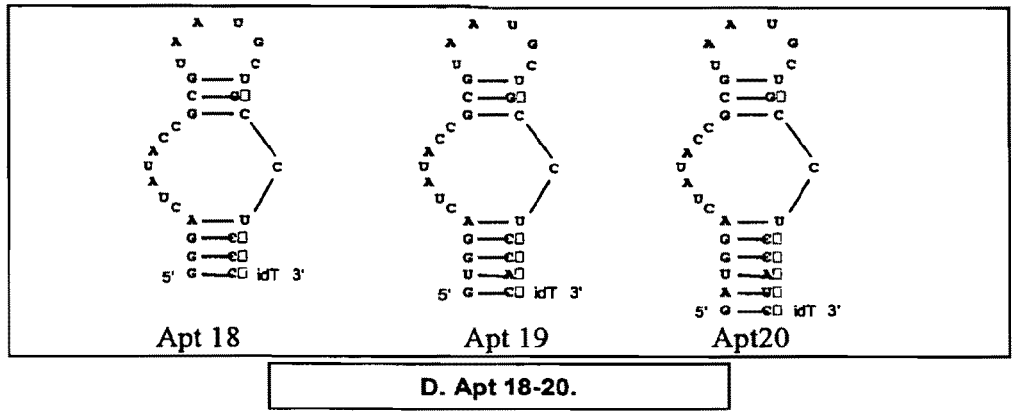
Figure 1:
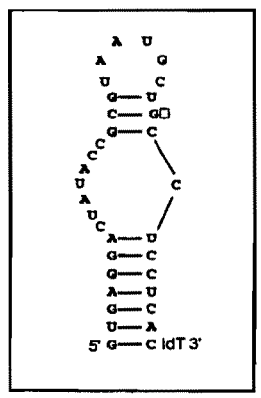
Figure 1:
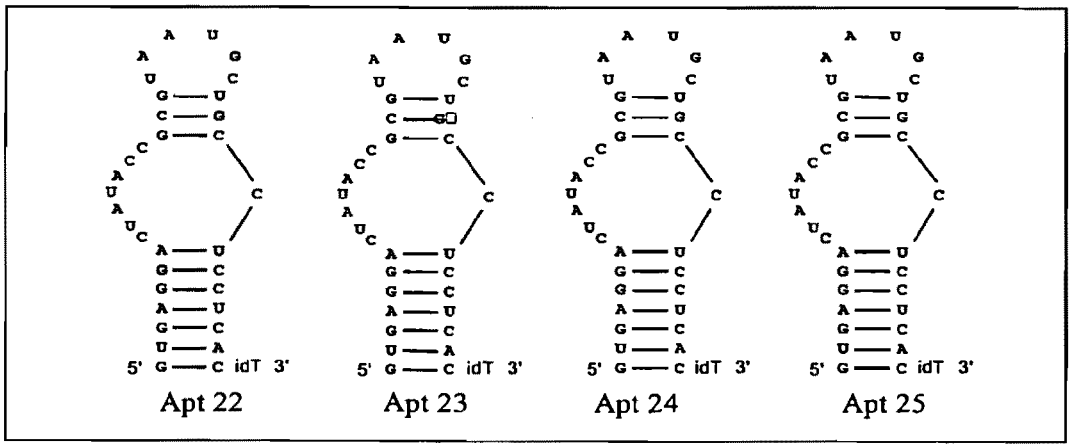
Figure 1:
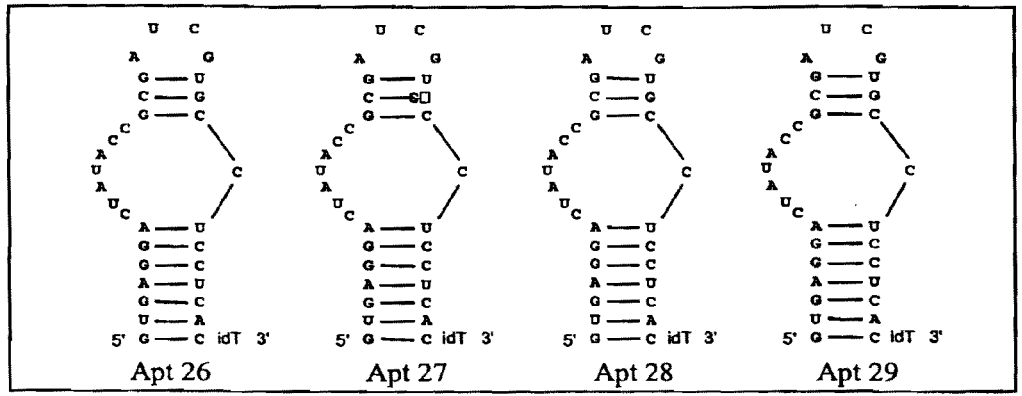
Figure 1:
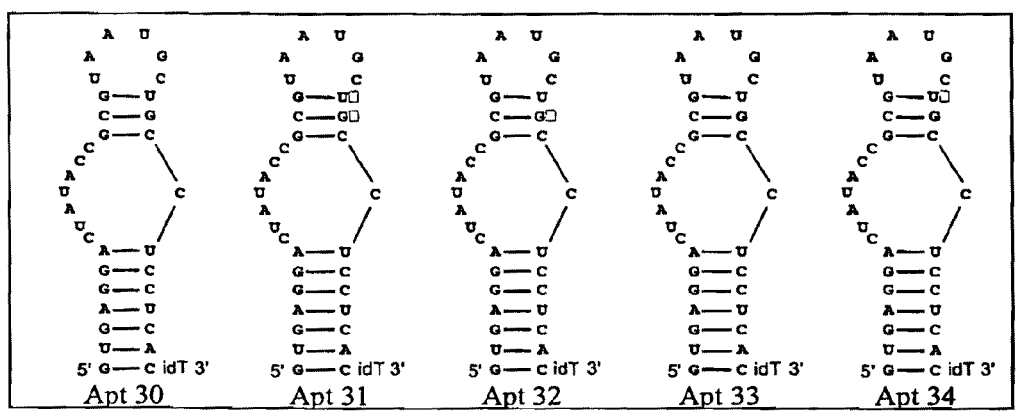
Figure 1:
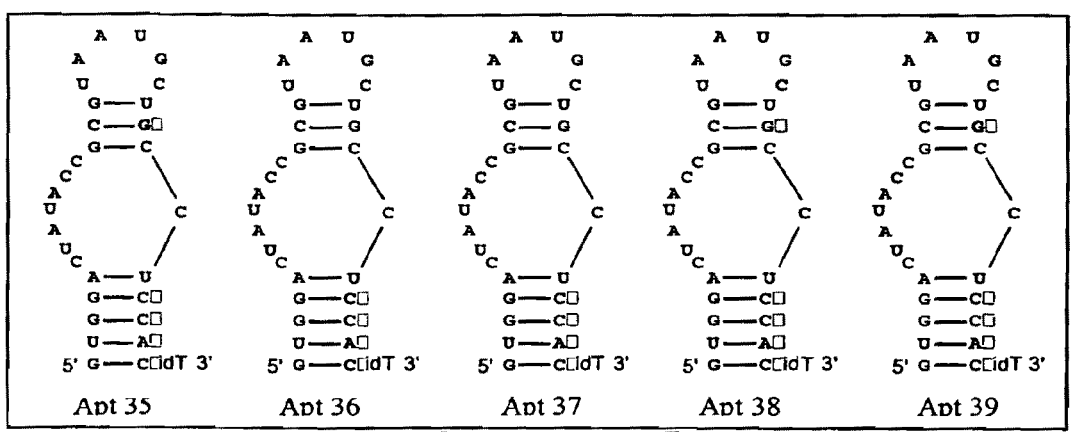

A "nucleic acid ligand" or "aptamer" is a nucleic acid that can form a three dimensional configuration, which allows it to interact as a ligand with a target molecule. The terms refer to oligonucleotides having specific binding regions that are capable of forming complexes with an intended target molecule in an environment wherein other substances in the same environment are not complexed to the oligonucleotide. The specificity of the binding is defined in terms of the comparative dissociation constants ($K_d$) of the aptamer for target as compared to the dissociation constant with respect to the aptamer and other materials in the environment or unrelated molecules in general. Typically, the $K_d$ for the aptamer with respect to the target will be 10-fold, 50-fold, 100-fold, or 200-fold less than the $K_d$ with respect to the unrelated material or accompanying material in the environment.

"Aptamer antidote pair" is meant to include a specified aptamer to a target molecule, and an oligonucleotide that changes the three dimensional configuration of the aptamer so that the aptamer can no longer interact with its target. The antidote can be an oligonucleotide complimentary to a portion of the aptamer. The antidote can change the conformation of the aptamer to reduce the target binding capacity of the aptamer by 10 to 100%, 20 to 100%, 25%, 40%, 50%, 60%, 70%, 80%, 90% or 100%, or any percentage in the range between 10 and 100% under physiological conditions. The antidote can also form a three dimensional structure with binding activity to a target molecule. This target can be the same or different from the target of the aptamer.

"Antidote," "Regulator" or "Modulator" refers to any pharmaceutically acceptable agent that can bind an aptamer and modify the interaction between that aptamer and modify the interaction between that aptamer and its target molecule (e.g., my modifying the structure of the aptamer) in a desired manner.

The terms "binding activity" and "binding affinity" are meant to refer to the tendency of a ligand molecule to bind or not to bind to a target. The energy of said interactions are significant in "binding activity" and "binding affinity" because they define the necessary concentrations of interacting partners, the rates at which these partners are capable of associating, and the relative concentrations of bound and free molecules-in a solution. The specificity of the binding is defined in terms of the comparative dissociation constants ($K_d$) of an antidote of a nucleic acid ligand as compared to the dissociation constant with respect to other materials in the environment or unrelated molecules in general.

As used herein, "consensus sequence" refers to a nucleotide sequence or region (which might or might not be made up of contiguous nucleotides) that is found in one or more regions of at least two nucleic acid sequences. A consensus sequence can be as short as three nucleotides long. It also can be made up of one or more noncontiguous sequences, with nucleotide sequences or polymers of up to hundreds of bases long interspersed between the consensus sequences. Consensus sequences can be identified by sequence comparisons between individual nucleic acid species, which comparisons can be aided by computer programs and other, tools for modeling secondary and tertiary structure from sequence information. Generally, the consensus sequence will contain at least about 3 to 20 nucleotides, more commonly from 6 to 10 nucleotides.

The terms "cardiovascular disease" and "cardiovascular diseases" are meant to refer to any cardiovascular disease as would be understood by one of ordinary skill in the art. Nonlimiting examples of particularly contemplated cardiovascular diseases include, but are not limited to, atherosclerosis, thrombophilia, embolisms, cardiac infarction (e.g., myocardial infarction), thromboses, angina, stroke, septic shock, hypertension, hyper-cholesterolemia, restenosis and diabetes (and associated diabetic retinopathy). Cardiovascular disease can be treated at any stage of progression, such as treatment of early onset cardiovascular disease as well as treatment of advanced cardiovascular disease. A therapeutic method directed toward-inhibiting the aggravation of cardiovascular disease by modulating coagulation is also included in the invention.

Aptamers to Factor IX

The invention provides improved nucleic acid ligands or aptamers that regulate blood coagulation through interaction with specific factors in the blood coagulation cascade. The invention also provides improved aptamer-antidote pairs to regulate coagulation. The improved aptamers target Factor IX gene products (which include Factor IXa) and thus reduce the non-specific side effects associated with other blood coagulation factor targets. Most factors in the coagulation cascade are broad spectrum proteins with a variety of physiological roles (i.e. thrombin).

The events which occur between injury and blood clot formation are a carefully regulated and linked series of reactions. In a cell-based model of coagulation, initiation takes place on tissue factor-bearing cells (monocytes, macrophages, endothelial cells). In the presence of FVIIa (complexed with tissue factor), activation of FIX and FX generates a small amount of thrombin from prothrombin (which subsequently activates FV). In the amplification phase (also referred to as the priming phase), the small amount of thrombin generated activates platelets, causing release of FVa, FXIa and FVIIIa. During the final phase of coagulation, propagation, FIXa complexes with FVIIIa, activating FX. The FXa-FVa complex, in the presence of calcium and phospholipids substrate (prothrombinase complex), leads to a "burst" of thrombin generation.

The cell-based model of anticoagulation has been instrumental in defining coagulation protease targets. Most previous work has focused on blood coagulation through a variety of factors such as thrombin. Thrombin is a broad acting protein with effects throughout the body. Inhibitors of thrombin can therefore have unanticipated side effects in addition to the effects on coagulation. Thrombin not only activates endothelial cells and induces leukocyte infiltration and edema but also activates astrocytes and microglia to propagate the focal inflammation and produce potential neurotoxic effects.

The inventor has determined that Factor IXa in particular represents an attractive target because of its participation in both the initiation and propagation phases of coagulation. Iterative in vitro selection techniques have been used to identify oligonucleotides capable of binding FIXa with high affinity ($K_d$ 0.65±0.2 nM). Experimental studies suggest that FIXa may have a critical role in thrombosis, as well as hemostasis. Infusion of purified FIXa into rabbits induces thrombosis (Gitel et al. (1977) *PNAS* 74:3028-32; Gurewich et al. (1979) *Thromb. Rsch.* 14:931-940). In contrast, active site-blocked FIXa prevented clot formation and reduced intra-arterial coronary thrombosis (Lowe (2001) *Brit. J. Haem.* 115:507-513).

Antibodies to factor IX have also been shown to interfere with the function of the intrinsic tenase complex, the activation of zymogen factor IX by factor XIa and by the tissue factor:factor VIIa complex and potently inhibit activated partial thromboplastin clotting times (APTT) in plasma of guinea pig and rat (Refino, C. J., et al, (1999) *Thromb and Haemost,* 82:1188-1195; Feuerstein G Z, et al. (1999) *Arterioscler Thromb Vasc Biol* 19(10):2554-62; Toomey J R, et al. (2000) *Thromb Res.* 100(1):73-9).

In one embodiment, the invention provides nucleic acid ligands or aptamers to a factor in the blood coagulation cascade. In some embodiments, the factors include Factor IX (FIX) or the cleavage product Factor IXa (FIXa). In some embodiments, the aptamers are ligands to the complex formed by FIXa with Factor VIIIa (FVIIIa), also known as the "intrinsic tenase complex." In some embodiments, the aptamers are ligands that inhibit the complex formation between FIXa and FVIIIa. In a subembodiment, the aptamers of the present invention bind to the complex of FIX and FVIIIa and inhibit activation of Factor X (FX). The aptamers can interact with FIX, FIXa or a complex formed with FVIIIa in the presence or absence of additional calcium. The aptamers can also interact with the factors of the complex at a cell membrane. In one embodiment, the aptamers bind to the intrinsic tenase complex at the membrane surface.

In one embodiment, the applicants have discovered improved aptamers to gene products of coagulation Factor IX (FIX), and to its cleavage product, Factor IXa (FIXa). In one embodiment, the nucleic acid ligand includes at least one region that binds to another region in the molecule via Watson-Crick base pairing (stem) and at least one region that does not bind to any other regions of the molecule under physiological conditions (loop). In a further embodiment, the nucleic acid ligand includes two stems (stem 1 and stem 2) and two loops (loop 1 and loop 2). In one embodiment, stem 1 is one to twenty nucleotides long. In a further embodiment, stem 1 is one to ten nucleotides long. In a further sub-embodiment, stem 1 is seven, six, five, four, three or two nucleotides long. In another embodiment, stem 2 one to twenty nucleotides long. In a further embodiment, stem 2 is one to ten nucleotides long. In a further sub-embodiment, stem 2 is seven, six, five, four, three or two nucleotides long.

The aptamers to a Factor IX gene product of the present invention can be comprised of ribonucleotides or deoxyribonucleotides, or a combination thereof. In general, the improved aptamers are at least 25 nucleotides long, and typically not longer than 35-40 nucleotides long. In one embodiment, aptamers are at least 25, 30, 35, or 40 nucleotides in length. In specific embodiments, the sequence of stem 1 includes 5 nucleotides in the 5'-3' direction. In a sub-embodiment, stem 1 includes three guanine (G) residues in the 5'-3' direction.

In an embodiment, the aptamers include the consensus nucleotide sequences gugg and the complimentary sequence ccac. When a number of individual, distinct aptamer sequences for a single target molecule have been obtained and sequenced, the sequences can be examined for "consensus sequences." As used herein, "consensus sequence" refers to a nucleotide sequence or region (which might or might not be made up of contiguous nucleotides) that is found in one or more regions of at least two aptamers, the presence of which can be correlated with aptamer-to-target-binding or with aptamer structure.

A consensus sequence can be as short as three nucleotides long. It also can be made up of one or more noncontiguous sequences. With nucleotide sequences or polymers of hundreds of bases long interspersed between the consensus sequences. Consensus sequences can be identified by sequence comparisons between individual aptamer species, which comparisons can be aided by computer programs and other, tools for modeling secondary and tertiary structure from sequence information. Generally, the consensus sequence will contain at least about 3 to 20 nucleotides, more commonly from 6 to 10 nucleotides. Not all oligonucleotides in a mixture can have the same nucleotide at such position; for example, the consensus sequence can contain a known ratio of particular nucleotides. For example, a consensus sequence might consist of a series of four positions wherein the first position in all members of the mixture is A, the second position is 25% A, 35% T and 40% C, the third position is T in all oligonucleotides, and the fourth position is G in 50% of the oligonucleotides and C in 50% of the oligonucleotides.

In specific embodiments, the aptamers include the nucleotide sequences of the following Seq ID Nos.:

| SeqID | Code | Size | Sequence |
|---|---|---|---|
| 9 | AptA | 35mer | (5'-3') sequence: augggga cuauacc gcg uaaugc ugc c uccccau t |
| 10 | Apt1 | 35mer | (5'-3') sequence: augggga cuauaccgcguaaugcugcc uccccau t |
| 9 | Apt2 | 35mer | (5'-3') sequence: augggga cuauacc gcg uaaugc ugc c uccccau t |
| 9 | Apt3 | 35mer | (5'-3') sequence: augggga cuauacc gcg uaaugc ugc c uccccau t |
| 9 | Apt4 | 35mer | (5'-3') sequence: augggga cuauacc gcg uaaugc ugc c uccccau t |
| 9 | Apt5 | 35mer | (5'-3') sequence: augggga cuauacc gcg uaaugc ugc c uccccau t |
| 11 | Apt6 | 29mer | (5'-3') sequence: ggga cuauaccgcguaaugcugcc uccc t |
| 12 | Apt7 | 31mer | (5'-3') sequence: gugga cuauaccgcguaaugcugcc uccac t |
| 13 | Apt8 | 33mer | (5'-3') sequence: gaugga cuauaccgcguaaugcugcc uccauc t |
| 14 | Apt9 | 29mer | (5'-3') sequence: cuga cuauaccgcguaaugcugcc ucag t |
| 15 | Apt10 | 31mer | (5'-3') sequence: ccuga cuauaccgcguaaugcugcc ucagg t |
| 16 | Apt11 | 33mer | (5'-3') sequence: cucuga cuauaccgcguaaugcugcc ucagag t |
| 10 | Apt12 | 35mer | (5'-3') sequence: augggga cuauaccgcguaaugcugcc ucccau t |
| 10 | Apt13 | 35mer | (5'-3') sequence: augggga cuauaccgcguaaugcugcc ucccau t |
| 17 | Apt14 | 35mer | (5'-3') sequence: gugagga cuauaccgcguaaugcugcc uccucac t |
| 17 | Apt15 | 35mer | (5'-3') sequence: gugagga cuauaccgcguaaugcugcc uccucac t |
| 17 | Apt16 | 35mer | (5'-3') sequence: gugagga cuauaccgcguaaugcugcc uccucac t |
| 17 | Apt17 | 35mer | (5'-3') sequence: gugagga cuauaccgcguaaugcugcc uccucac t |
| 11 | Apt18 | 29mer | (5'-3') sequence: ggga cuauaccgcguaaugcugcc uccc t |
| 12 | Apt19 | 31mer | (5'-3') sequence: gugga cuauaccgcguaaugcugcc uccac t |
| 13 | Apt20 | 33mer | (5'-3') sequence: gaugga cuauaccgcguaaugcugcc uccauc t |
| 18 | Apt21 | 35mer | (5'-3') sequence: gugagga cuauacc gcg uaaugc ugc c uccucac t |
| 18 | Apt22 | 35mer | (5'-3') sequence: gugagga cuauacc gcg uaaugc ugc c uccucac t |
| 18 | Apt23 | 35mer | (5'-3') sequence: gugagga cuauacc gcg uaaugc ugc c uccucac t |
| 18 | Apt24 | 35mer | (5'-3') sequence: gugagga cuauacc gcg uaaugc ugc c uccucac t |
| 18 | Apt25 | 35mer | (5'-3') sequence: gugagga cuauacc gcg uaaugc ugc c uccucac t |
| 27 | Apt26 | 33mer | (5'-3') sequence: gugagga cuauacc gca aucg ugc c uccucac t |
| 28 | Apt27 | 33mer | (5'-3') sequence: gugagga cuauacc gca aucg ugc c uccucac t |
| 29 | Apt28 | 33mer | (5'-3') sequence: gugagga cuauacc gca aucg ugc c uccucac t |
| 30 | Apt29 | 33mer | (5'-3') sequence: gugagga cuauacc gca aucg ugc c uccucac t |
| 18 | Apt30 | 35mer | (5'-3') sequence: gugagga cuauacc gcg uaaugc ugc c uccucac t |
| 18 | Apt31 | 35mer | (5'-3') sequence: gugagga cuauacc gcg uaaugc ugc c uccucac t |
| 18 | Apt32 | 35mer | (5'-3') sequence: gugagga cuauacc gcg uaaugc ugc c uccucac t |
| 18 | Apt33 | 35mer | (5'-3') sequence: gugagga cuauacc gcg uaaugc ugc c uccucac t |
| 18 | Apt34 | 35mer | (5'-3') sequence: gugagga cuauacc gcg uaaugc ugc c uccucac t |
| 19 | Apt35 | 31mer | (5'-3') sequence: gugga cuauacc gcg uaaugc ugc c uccac t |
| 19 | Apt36 | 31mer | (5'-3') sequence: gugga cuauacc gcg uaaugc ugc c uccac t |
| 19 | Apt37 | 31mer | (5'-3') sequence: gugga cuauacc gcg uaaugc ugc c uccac t |

-continued

| SeqID | Code | Size | Sequence |
|---|---|---|---|
| 19 | Apt38 | 31mer | (5'-3') sequence: gugga cuauacc gcg uaaugc ugc c uccac t |
| 19 | Apt39 | 31mer | (5'-3') sequence: gugga cuauacc gcg uaaugc ugc c uccac t |

In one embodiment, the aptamer to Factor IX comprises, consists, or consists essentially of, the nucleotide sequence: gugga cuauacc gcg uaaugc ugc c uccac t (SeqID 19).

Aptamer Antidotes

It is important to be able to release blood coagulation factors from inhibition. Life threatening diseases can result from over-inhibition of the blood coagulation factors such as Factor IX. For example, hemophilia B results from deficiencies in factor IX. All patients with hemophilia B have prolonged coagulation time and decreased factor IX clotting activity. Like hemophilia A, there are severe, moderate and mild forms of hemophilia B and reflect the factor IX activity in plasma.

Therefore, another embodiment of the invention includes an antidote paired with the aptamer of the invention. Antidotes or modulators can include any pharmaceutically acceptable agent that can bind an aptamer and modify the interaction between that aptamer and its target molecule (e.g., by modifying the structure of the aptamer) in a desired manner. Examples of such antidotes include (A) oligonucleotides complementary to at least a portion of the aptamer sequence (including ribozymes or DNAzymes or peptide nucleic acids (PNAs)), (B) nucleic acid binding peptides, polypeptides or proteins (including nucleic acid binding tripeptides (see, generally, Hwang et al. (1999) Proc. Natl. Acad. Sci. USA 96:12997), and (C) oligosaccharides (e.g. aminoglycosides (see, generally, Davis et al. (1993) Chapter 8, p. 185, RNA World, Cold Spring Harbor Laboratory Press, eds. Gestlaad and Atkins; Werstuck et al. (1998) Science 282:296; U.S. Pat. Nos. 5,935,776 and 5,534,408). (See also the following which disclose types of antidotes that can be used in accordance with the present invention: Chase et al. (1986) Ann. Rev. Biochem. 56:103, Eichorn et al. (1968) J. Am. Chem. Soc. 90:7323, Dale et al. (1975) Biochemistry 14:2447 and Lippard et al. (1978) Acc. Chem. Res. 11:211).

In one embodiment, the antidote oligonucleotide reverses or neutralizes at least 25%, 50%, 75%, 80% or 90% of the anticoagulant activity of the aptamer. The antidote generally has the ability to substantially bind to a nucleic acid ligand in solution at antidote concentrations of less than one 1 µM, or less than 0.1 µM and more preferably less than 0.01 µM. In one embodiment, the antidote reduces the biological activity of the aptamer by 50%.

Complementary Oligonucleotides

In one embodiment, the improved antidote of the invention is an oligonucleotide that comprises a sequence complementary to at least a portion of the targeted aptamer sequence. Absolute complementarity is not required. The sequence in one embodiment has sufficient complementarity to be able to hybridize with the aptamer. The ability to hybridize will depend on both the degree of complementarity and the length of the antisense nucleic acid. Advantageously, the antidote oligonucleotide comprises a sequence complementary to 6-25 consecutive nucleotides of the targeted aptamer, preferably, 8-20 consecutive nucleotides, more preferably, 10-15 consecutive nucleotides. In specific aspects the antidote is at least 10-25 nucleotides, at least 15-25, at least 20-25, at least 14, 17 or at least 25 nucleotides long. The antidotes of the invention can be DNA or RNA or chimeric mixtures or derivatives or modified versions thereof, single-stranded.

Formation of duplexes by binding of complementary pairs of short oligonucleotides is a fairly rapid reaction with second order association rate constants generally between $1 \times 10^6$ and $3 \times 10^5$ $M^1s^1$. Stability of short duplexes can be highly dependent on the length and base-composition of the duplex. The thermodynamic parameters for formation of short nucleic acid duplexes have been rigorously measured, resulting in nearest-neighbor rules for all possible base pairs such that accurate predictions of the free energy, $T_m$ and thus half-life of a given oligoribonucleotide duplex can be calculated (e.g., Xia et al. (1998) Biochem. 37:14719; see also Eguchi et al. (1991) Antigensis RNA, Annu. Rev. Biochem. 60:631).

In a specific embodiment, the present invention provides improved antidotes that specifically and rapidly reverse the anticoagulant and antithrombotic effects of the improved aptamers that target components of the coagulation pathway, in particular the aptamers of FIX and FIXa. The antidotes can be administered to reverse the aptamer activity by a physician or other health care provider. In specific embodiments, the improved antidotes according to the present invention are nucleic acids corresponding to the sequences: (5'-3') sequence: cgcgguauaguccccau (Apt/AD; SEQ ID NO:1); (5'-3') sequence: cgcgguauaguccc (Apt6/AD SEQ ID NO:2); (5'-3') sequence: cgcgguauaguccac (Apt7/AD; SEQ ID NO:3); (5'-3') sequence: cgcgguauaguccauc (Apt8/AD; SEQ ID NO:4); (5'-3') sequence: cgcgguauagucag (Apt9/AD; SEQ ID NO:5); (5'-3') sequence: cgcgguauagucagg (Apt10/AD; SEQ ID NO:6); (5'-3') sequence: cgcgguauagucagag (Apt11/AD; SEQ ID NO:7); (5'-3') sequence: cgcgguauaguccucac (Apt14/AD; SEQ ID NO:8), or any modification or derivative thereof. The antidote sequence can be at least 20%, 50%, 75% or 90% homologous to the sequence of the corresponding aptamer. In one embodiment, the antisense sequence is separately administered.

Antisense techniques are discussed for example, in Okano, et al. (1991) J. Neurochem. 56:560 and "Oligodeoxynucleotides as Antisense Inhibitors of Gene Expression," (1988) CRC Press, Boca Raton, Fla. In one embodiment, oligonucleotide antidotes of the invention are advantageously targeted at single-stranded regions of the aptamer. This can facilitate nucleation and, therefore, the rate of aptamer activity modulation, and also, generally leads to intermolecular duplexes that contain more base pairs than the targeted aptamer. The aptamer to Factor IXa of the present invention may be used to design an antisense oligonucleotide. The antisense oligonucleotide hybridizes to the aptamer in vivo and blocks the binding of the aptamer to factor IXa.

To design an improved antidote to the improved aptamers of the invention, various strategies can be used to determine the optimal binding site. The complimentary oligonucleotides can be "walked" around the aptamer. This "walking" procedure includes, after a minimal consensus ligand sequence has been determined for a given improved aptamer, adding random sequence to the minimal consensus ligand sequence and evolving additional contacts with the target, such as in separate but adjacent domains. A walking experiment can involve two experiments performed sequentially. A new candidate mixture is produced in which each of the members of the candidate mixture has a fixed nucleic acid-region that corresponds to a nucleic acid ligand of interest. Each member of the candidate mixture also contains a randomized region of sequences. According to this method it is possible to identify what are referred to as "extended" nucleic acid ligands, which contain regions that can bind to more than one binding domain of a target.

Changes in the sugar can affect antidote stability, in part because sugar modifications that result in RNA-like oligonucleotides, e.g., 20-fluoro or 20-methoxy, do not appear to serve as substrates for RNase H. Alterations in the orientation of the sugar to the base can also affect RNase H activation. Additionally, backbone modifications influence the ability of oligonucleotides to activate RNase H. Methylphosphonates do not activate it, whereas phosphorothioates are excellent substrates. In addition, chimeric molecules have been studied as oligonucleotides that bind to RNA and activate RNase H. For example, oligonucleotides comprising wings of 20-methoxy phosphonates and a five-base gap of deoxyoligonucleotides bind to their target RNA and activate RNase H.

In one embodiment, 2'-O-methyl modified antidotes (e.g., 2'-O-methyl oligonucleotides) about 15 nucleotides in length can be used, the complementarity of which is staggered by about 5 nucleotides on the aptamer (e.g., oligonucleotides complementary to nucleotides 1-15, 6-20, 11-25, etc.). The impact of tertiary structure of the improved aptamer on the efficiency of hybridization is difficult to predict. Assays described in the Examples that follow can be used to assess the ability of the different oligonucleotides to hybridize to a specific aptamer. The ability of the different oligonucleotide antidotes to increase the rate of dissociation of the aptamer from, or association of the aptamer with, its target molecule can also be determined by conducting kinetic studies using, for example, BIACORE assays. Oligonucleotide antidotes can be selected such that a 5-50 fold molar excess of oligonucleotide, or less, is required to modify the interaction between the aptamer and its target molecule in the desired manner.

The antidotes of the invention may be conjugated to another molecule, e.g., a peptide, hybridization triggered cross-linking agent, transport agent, hybridization-triggered cleavage agent, etc.

The antisense oligonucleotide may optionally comprise at least one modified base moiety, including but not limited to one selected from 5-fluorouracil, 5-fluorocytosine, 5-bromouracil, 5-bromocytosine, 5-chlorouracil, 5-chlorocytosine, 5-iodouracil, 5-iodocytosine, 5-methylcytosine, 5-methyluracil, hypoxanthine, xantine, 4-acetylcytosine, 5-(carboxyhydroxylmethyl) uracil, 5-carboxymethylamin-O-methyl thiouridine, 5-carboxymethylamin-O-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 6-methylcytosine, N6-adenine, 7-methylguanine, 5-methylamin-O-methyluracil, 5-methoxyamin-O-methyl-2-thiouracil, beta-D-mannosylqueosine, 5'-methoxycarboxymethyluracil, 5-methoxyuracil, 5-methoxycytosine, 2-methylthio-N&isopentenyladenine, uracil oxyacetic acid (v), butoxosine, pseudouracil, queosine, 2-thiocytosine, 5-methyl thiouracil, 2-thiouracil, 4-thiouracil, 5-methyluracil, uracil-5-oxyacetic acid methylester, uracil oxyacetic acid (v), 5-methyl thiouracil, 3-(3-amino-3-N carboxypropyl) urdeil, (acp3)w, and 2,6-diaminopurine.

The antidotes may also include at least one modified sugar moiety selected from the group including, but not limited to, arabinose, 2-fluoroarabinose, xylulose, hexose, 2'-fluororibose, 2'-O-methylribose, 2'-O-methoxyethylribose, 2'-O-propylribose, 2'-O-methylthioethylribose, 2'-O-diethylaminooxyethylribose, 2'-O-(3-aminopropyl)ribose, 2'-O-(dimethylaminopropyl)ribose, 2'-O-(methylacetamido) ribose, and 2'-O-(dimethylaminoethyloxyethyl)ribose. In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiainidate, a methylphosphonate, an alkyl phosphotriester, and a formacetal or analog thereof.

Ribozymes and DNAzymes

Improved aptamers or antidotes can also be enzymatic nucleic acids. Such a ribozyme or DNAzyme act by first binding to a target RNA or DNA (see Cech U.S. Pat. No. 5,180,818) and then cleaving the target. An enzymatic nucleic acid can repeatedly bind and cleave new targets thereby allowing for inactivation of RNA aptamers. There are at least five classes of ribozymes that each display a different type of specificity. In the case of antidotes, this enzymatic activity can complement or substitute for the introduction of a "suicide position" in the improved aptamer.

The enzymatic nature of a ribozyme may be advantageous over other technologies because the effective concentration of ribozyme necessary to effect a therapeutic treatment is lower than that of an antisense oligonucleotide. A single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it may be that the specificity of action of a ribozyme is greater than that of antisense oligonucleotide binding the same RNA site.

Another class of catalytic molecules are called "DNAzymes". DNAzymes are single-stranded, and cleave both RNA and DNA. A general model for the DNAzyme has been proposed, and is known as the "10-23" model. DNAzymes following the "10-23" model, also referred to simply as "10-23 DNAzymes", have a catalytic domain of 15 deoxyribonucleotides, flanked by two substrate-recognition domains of seven to nine deoxyribonucleotides each. In vitro analyses show that this type of DNAzyme can effectively cleave its substrate RNA at purine:pyrimidine junctions under physiological conditions. As used herein, "DNAzyme" means a DNA molecule that specifically recognizes and cleaves a distinct target nucleic acid sequence, which may be either DNA or RNA.

Adapted Nucleic Acids

In another aspect of the invention, the antidote to the improved aptamers are Peptide Nucleic Acids (PNAs). PNAs are compounds that are analogous to oligonucleotides, but differ in composition in that the deoxyribose backbone of oligonucleotide is replaced by a peptide backbone. Each subunit of the peptide backbone is attached to a naturally-occurring or non-naturally-occurring nucleobase.

PNAs can be advantageous as fast acting antidotes because they bind more tightly to the corresponding improved aptamers than their non-substituted oligonucleotide counterparts. PNAs bind to both DNA and RNA and the resulting PNA/DNA or PNA/RNA duplexes are bound tighter than corresponding DNA/DNA or DNA/RNA duplexes as evidenced by their higher melting temperatures ($T_m$). Another advantage of PNA/DNA(RNA) duplexes is that $T_m$ is practically independent of salt concentration. Since PNAs are an analogue of DNA in which the backbone is a pseudopeptide rather than a sugar, they mimic the behaviour of DNA and binds complementary nucleic acid strands.

PNAs are synthetic polyamides comprised of repeating units of the amino acid, N-(2-aminoethyl)-glycine, to which the nucleobases adenine, cytosine, guanine, thymine and uracil are attached through a methylene carbonyl group. Natural and unnatural nucleobases, such as pseudo isocytosine, 5-methyl cytosine and 2,6-diaminopurine, inosine, uracil, 5-methylcytosine, thiouracil, 2,6-diaminopurine, bromothymine, azaadenines or azaguanines among many others, also can be incorporated in PNA synthons. PNAs are most commonly synthesized from monomers (PNA synthons) protected according to the t-Boc/benzyl protection strategy, wherein the backbone amino group of the growing polymer is protected with the t-butyloxycarbonyl (t-Boc) group and the exocyclic amino groups of the nucleobases, if present, are protected with the benzyloxycarbonyl (benzyl) group. PNA synthons protected using the t-Boc/benzyl strategy are now commercially available.

Figure 2:
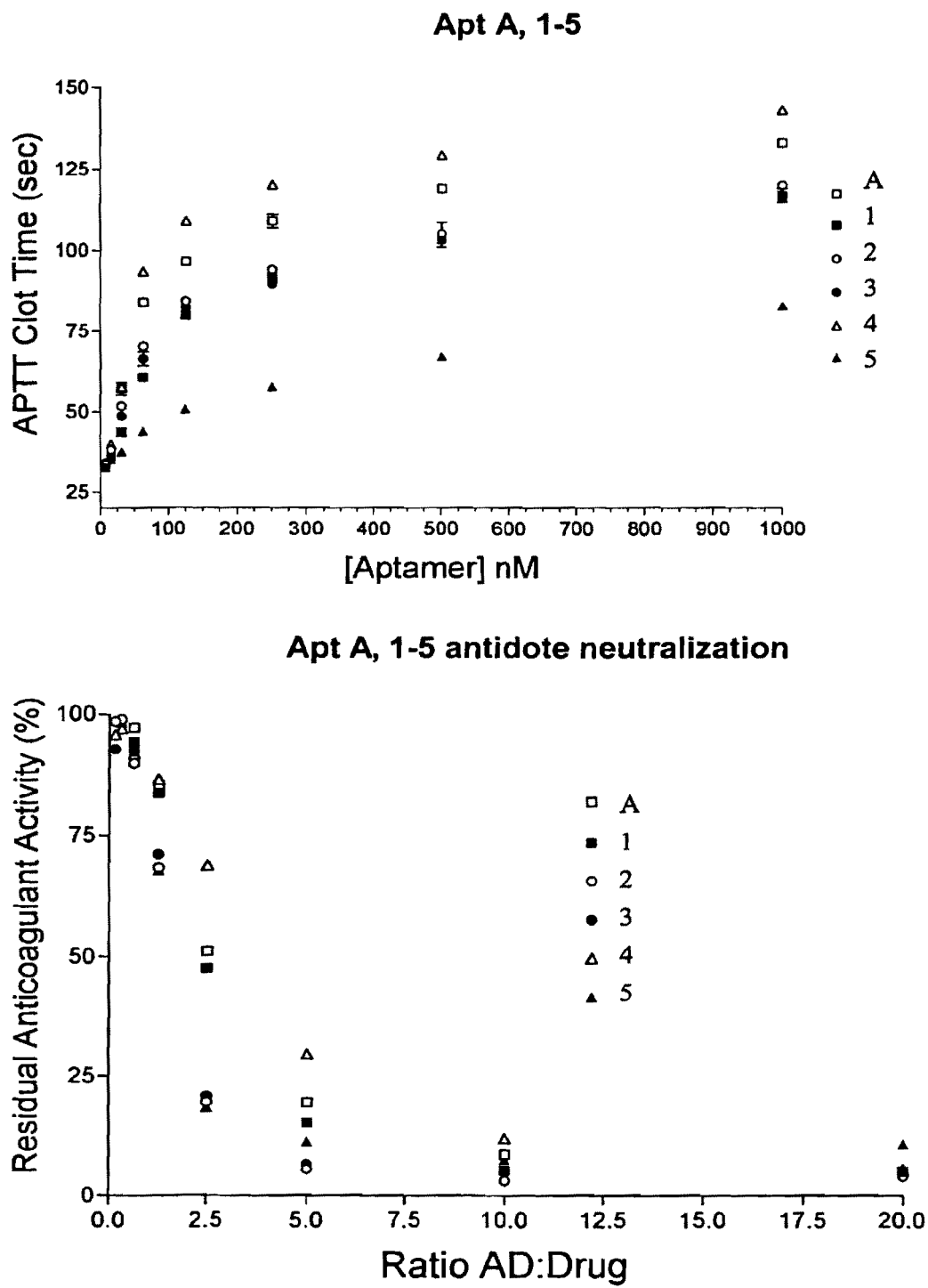
FIG. 2 is a graph of results of activated partial thromboplastin time (APTT) test assays of aptamers Apt A and Apt 1-5 (left panel) and neutralizability by antidote AptA-AD.

Morpholino nucleic acids (MNAs) can also be advantageous in antidote preparation because morpholinos are completely resistant to nucleases and they appear to be free of most or all of the non-antisense effects that plague S-DNAs. MNAs are assembled from morpholino subunits, each of which contains one of the four genetic bases (adenine, cytosine, guanine, and thymine) linked to a 6-membered morpholine ring. Subunits of are joined by non-ionic phosphorodiamidate intersubunit linkages to give a MNA. These MNAs can have substantially better antisense properties than do RNA, DNA, and their analogs having 5-membered ribose or deoxyribose backbone moieties joined by ionic linkages (see wwwgene-tools.com/Morpholinos/body_morpholinos.HTML).

U.S. Pat. No. 6,153,737 to Manoharan et al. is directed to derivatized oligonucleotides wherein the linked nucleosides are functionalized with peptides, proteins, water soluble vitamins or lipid soluble vitamins. This disclosure was directed towards antisense therapeutics by modification of oligonucleotides with a peptide or protein sequence that aids in the selective entry of the complex into the nuclear envelope. Similarly, water-soluble and lipid-soluble vitamins can be used to assist in the transfer of the anti-sense therapeutic or diagnostic agent across cellular membranes.

Locked nucleic acids (LNAs) can also be used to preparet the antidotes of the present invention. LNAs are a novel class of DNA analogues that possess certain features that make them prime candidates for improving nucleic acid properties. The LNA monomers are bicyclic compounds structurally similar to RNA-monomers. LNAs share most of the chemical properties of DNA and RNA, are water-soluble, can be separated by gel electrophoreses, ethanol precipitated, etc. (Tetrahedron, 54, 3607-3630 (1998)). However, introduction of LNA monomers into either DNA or RNA oligos results in high thermal stability of duplexes with complementary DNA or RNA, while, at the same time obeying the Watson-Crick base-pairing rules. This high thermal stability of the duplexes formed with LNA oligomers together with the finding that primers containing 3' located LNA(s) are substrates for enzymatic extensions, e.g. the PCR reaction, makes these compounds suitable for the antidotes of the present invention. For examples of LNAs see U.S. Pat. No. 6,316,198.

In other embodiments, the stabilized nucleic acid can be a PCO (pseudocyclic oligonucleobase), or a 2'-O,4'-C-ethylene bridged nucleic acid (ENA).

Modifications

The improved aptamers and aptamer-antidote combinations of the present invention are modified by substituting particular sugar residues, by changing the composition of the aptamer and the size of particular regions in the aptamer, and by designing aptamers that can be more effectively inhibited by antidotes. The design of aptamers includes an appreciation for the secondary structure of the aptamer (see FIG. 1) and the relationship between the secondary structure and the antidote control. Unlike conventional methods of modifying nucleic acids, the design of the improved aptamers to FIX gene products included in the invention must include a consideration of the antidote control. Controlled aptamers require that the aptamer be stable in circulation but not so stable that it is not antidote controlled. The aptamers can be modified by truncation, but antidotes need to be designed to control each aptamer when truncated. Further, certain modifications, particularly at the interface of the stems and loops cannot be modified from 2'-fluoro or the aptamer can lose activity.

In one embodiment, the design includes decreasing the 2'-hydroxyl content of the aptamer or the antidote, or both. In another embodiment, the design includes decreasing the fluoro content of the aptamer or the antidote, or both. In a further embodiment, the design includes increasing the O-methyl content of the aptamer or the antidote, or both. In a further embodiment, the design includes decreasing the size of the aptamer. In another embodiment, the size of the antidote is changed in relation to the size of the aptamer. In yet another embodiment, guanine strings are reduced to less than four guanine, or less than three guanine, or less than two guanine or no guanines. However, the joint effect of these changes must meet the challenge of creating an anticoagulant that provides adequate activity but is easily neutralized by the antidote.

Yet another embodiment includes a method of designing aptamers with a "suicide position" which allows more effective regulation by paired antidotes. In one embodiment, this position becomes single stranded and labile upon binding of the antidote to the improved aptamer and allows for cleavage of the improved aptamer upon binding of the antidote by enzymes in the circulation, such as blood or liver endonucleases, thereby effectively eliminating the active aptamer from circulation. The suicide position can be, in one embodiment, at a guanine in stem 2 that is hydroxylated. In one embodiment, the aptamer is in a double stranded configuration until bound with an antidote and becomes single stranded and available for cleavage upon binding of the antidote.

The applicants have discovered aptamer-antidote pairs that are stable and bioactive by including secondary modifications on either the aptamer or antidote or both. In specific embodiments, the aptamers to Factor IX include modified nucleotides. In one embodiment, the aptamer contains one or more 2'-O-methyl groups. In another embodiment, the aptamer and antidote contain one or more 2'-O-methyl and one or more 2'-fluoro modifications. In another embodiment, the aptamer and antidote contain no 2'-fluoro modifications. In yet another embodiment, the aptamer includes one or more 2'-O-methyl and one or more 2'-fluoro modifications on its stem. The aptamers can also include nucleotides that are modified with soluble polymers. Such polymers can include polyethylene glycol, polyamines, polyesters, polyanhydrides, polyethers or other water soluble pharmaceutically acceptable polymer.

Purines within given aptamer sequence of FIX inhibitor can tolerate substitution of 2'-O-methyl sugars for current 2' hydroxyl sugars (Example 1, FIG. 1). Applicants found that the aptamers fall into three classes: (1) gain of anticoagulant activity (Apt-4); (2) moderate loss of activity (Apt-1, 2, and 3); and (3) severe loss of activity (Apt 5) (FIG. 2). Data from Apt-5 indicates that the impact of wholly substituting 2'-O-methyl purines for 2' hydroxyl purines is significantly greater than any individual sector substitution alone (FIG. 2). In the case of this aptamer, it is possible that this suggests potential interaction between sectors, or that impairment caused by substitution within one of the sectors is exacerbated by additional modifications (ie. one of the sectors is an Achilles heel). The enhanced antidote control exhibited by Apt-1, 2 and 3 suggests that introduction of 2'O-methyl residues within the antidote binding site improves the ability of the antidote oligonucleotide to bind to the aptamer. This is consistent with the increase in thermodynamic stability observed for duplexes containing 2'-O-methyl RNA residues in each strand, and suggests that duplexes of 2'-O-methyl-2'-O-methyl strands are more thermodynamically stable than duplexes composed of 2'O-methyl-2' fluoro strands. An alternative conclusion is that the reduction in activity of Apt-1, 2 and 3 leads to more "free" aptamer in the plasma at any given time, which is thus more readily bound by the antidote oligonucleotide In another embodiment, aptamers of the present invention can include modified pyrimidine nucleosides. Replacing 2' fluoropyrimidines with 2'-O-methyls within stem 1 improved activity and yielded a compound that tolerates a greater level of substitution. Comparison of the activity of Apt 30 and 33 to Apt 31 and 32 demonstrates that C16 needs to contain a 2' fluoro sugar and G25 a 2' hydroxyl sugar (FIG. 16a). Activity observed between Apt 31 and 32 suggests that remaining positions within stem 2 can contain 2'-O-methyl sugars. In fact, Apt 31 appears to possess slightly greater potency than Apt 32, indicating that a compound with 2' fluoro at C16, 2'hydroxyl at G25, and the remaining residues 2'-O-methyl may exhibit greater potency than Apt 33. Apt 33 is more readily neutralizable than Apt 30, suggesting additional 2'-O-methyl residue within the antidote-binding site of the aptamer improves antidote binding. Apt 34 have C16 as a 2' fluoro rather than 2'-O-methyl nucleoside (FIG. 16b). Substitution increased anticoagulant activity (compare Apt 34 to Apt 33) but did result in a modest loss of "neutralizability", although 34 still requires a lower excess of antidote to achieve 90% neutralization (~5:1 vs 10:1) than the parental AptA compound (FIG. 16b). Both results are consistent with an increase in the stability of stem 2 due to 2'-O-methyl substitution. It is surprising that others have not obviously pursued 2'-O-methyl substitution of 2'-fluoropyrimidines, as such substitution reduces cost of synthesis and appears to enable increased aptamer modification due to increased stem stability.

In one embodiment, at least on guanine in stem 2 of an aptamer includes a hydroxyl sugar (2'-OH). In one embodiment, at least one uridine in stem 1 or stem 2 is a modified base. This can be either a 2'-fluoro (2'-F) or 2'-O-methyl (2'-OCH$_3$) modification. In one embodiment, at least one uridine in stem 1 or stem 2 is 2'-O-methyl modified. In one embodiment, at least one cytidine in stem 2 is modified. In one embodiment, at least on cytidine in stem 2 is 2'-Fluoro modified.

Figure 6:
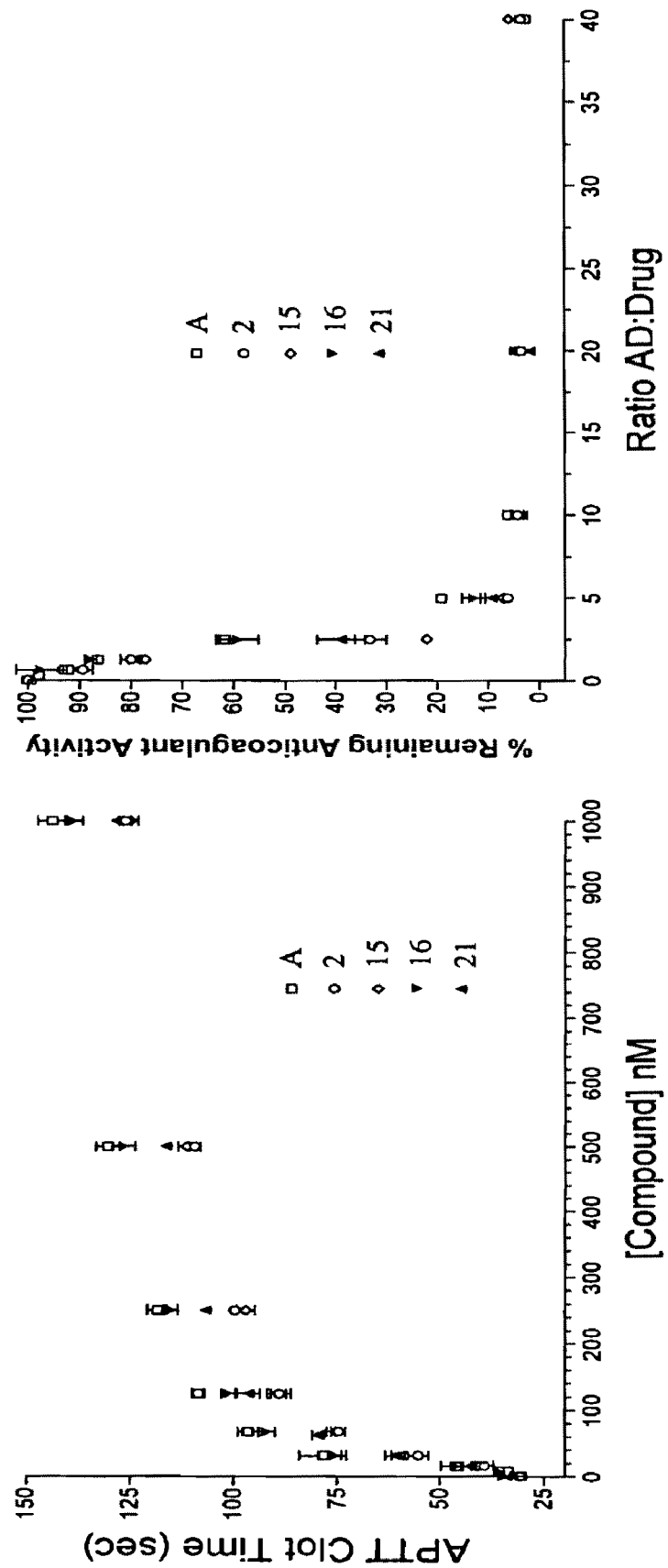
FIG. 6 is a graph of results of activated partial thromboplastin time (APTT) test assays of aptamers Apt 2, 15, 16 and 21 (left panel) and neutralizability by antidote (right panel).
Figure 7:
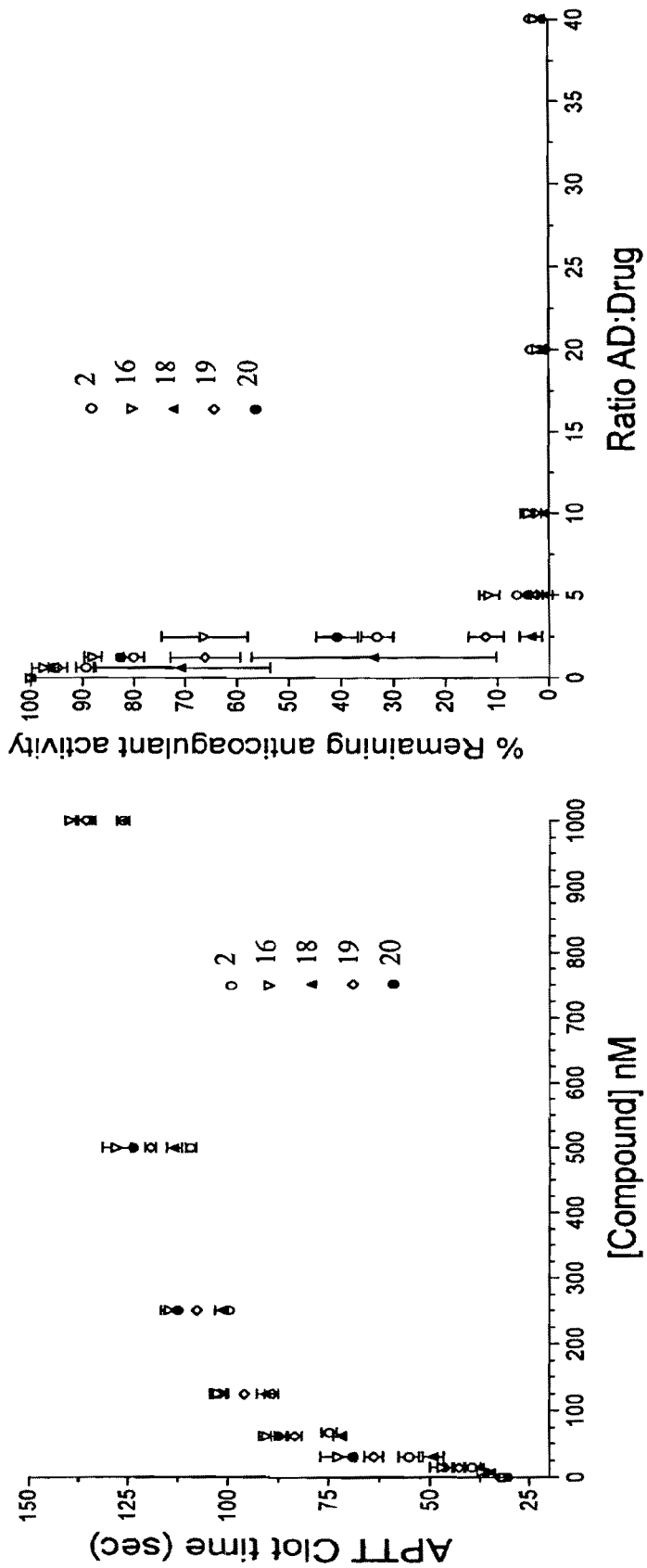
FIG. 7 is a graph of results of activated partial thromboplastin time (APTT) test assays of aptamers Apt 2 and 16-20 (left panel) and neutralizability by antidote (right panel).

However, comparison of the anticoagulant activity of Apt 12 with Apt 13 and 17 (FIG. 6) demonstrates that the loss of activity observed for Apt 6-11 is due to the presence of 2'-O-methyl substitutions at one or more critical residues (FIG. 7). Comparison of the anticoagulant activity of Apt 14 to Apt 12 indicates that the stretch of 4 consecutive guanosines within stem 1 can be altered without a significant impact on anticoagulant activity. Comparison of Apt 15 and 16 with Apt 2, 12 and 17 a) demonstrates that the presence of 2'-O-methyl sugars at each position within stem 1 except for the closing A-U pair at the top of stem 1 enhances activity; and b) demonstrates that the sugar of the U in this base pair must be 2'-fluoro for the aptamer to retain potency; and c) suggests that the sugar of the A in this base pair can be a 2'-O-methyl sugar without a significant impact on anticoagulant activity. In fact, Apt 16 retains essentially full potency.

Data suggests that the antidote can more readily bind the aptamer when stem 1 is a 2'-O-methyl-2' fluoro stem as opposed to when both strands of the duplex contain largely 2'-O-methyl residues. This is again consistent with the notion that duplexes composed of 2'-O-methyl residues in both strands are more stable than those composed of a largely 2'-O-methyl strand and a largely 2' fluoro strand. The enhanced anticoagulant activity of Apt 16 vs. Apt 15 is also consistent with this. Alternatively, the difference in neutralizability between 14, 15 and 16 could be due to the enhanced potency of Apt 16 compared to these two compounds. Regardless, all are neutralized at least as well as AptA. Based upon the observation that the anticoagulant activity of Apt 14 and 15 were similar, the sugar of the A at the stop of stem 1 was 2'-O-methyl substituted (Apt 21, FIG. 8).

Figure 9:
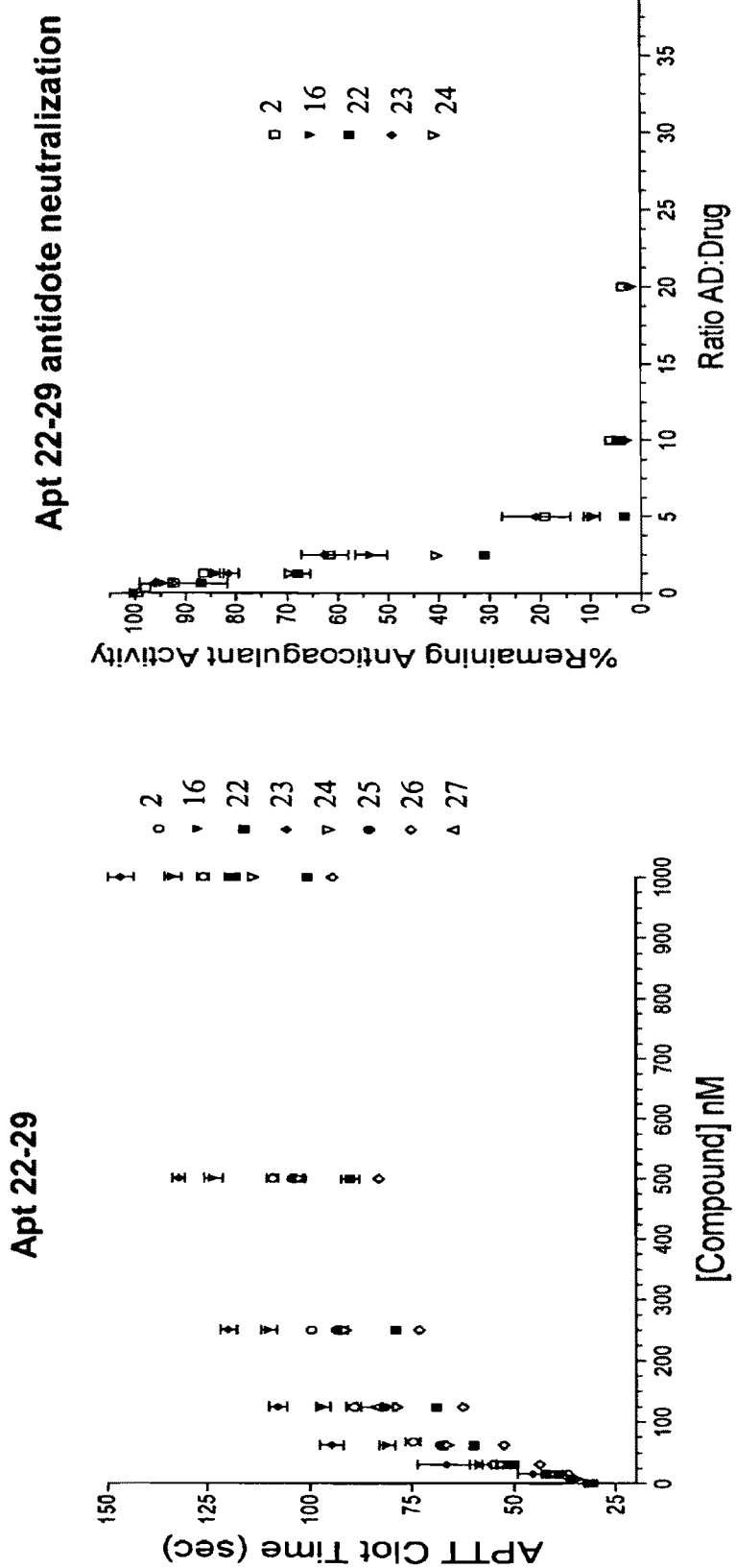
FIG. 9 is a graph of results of activated partial thromboplastin time (APTT) test assays of aptamers Apt 2, 16 and 22-27 (left panel) and neutralizability by antidote (right panel).

Substitution of a 2'-O-methyl sugar at this adenosine residue is well tolerated in the background of a largely 2'-O-methyl stem (FIG. 9). In fact, the potency of Apt 21 is intermediate between Apt 16 and 15. Antidote neutralization of Apt 21 is enhanced as compared to Apt 16 (see especially the 2.5:1 and 5:1 AD:Drug data points in FIG. 9).

Sugar modifications may ensure stability but they do not guarantee adequate pharmacokinetics for aptamers to be therapeutically active. In healthy individuals, aptamers are cleared from plasma within minutes of IV injection, probably through renal excretion. Keeping intact aptamers in the blood from hours to days after injection has been accomplished by conjugating them to larger macromolecules such as polyethyleneglycol (PEG). In another embodiment, aptamer plasma clearance has also been decreased by embedding them in liposomes.

Figure 3:
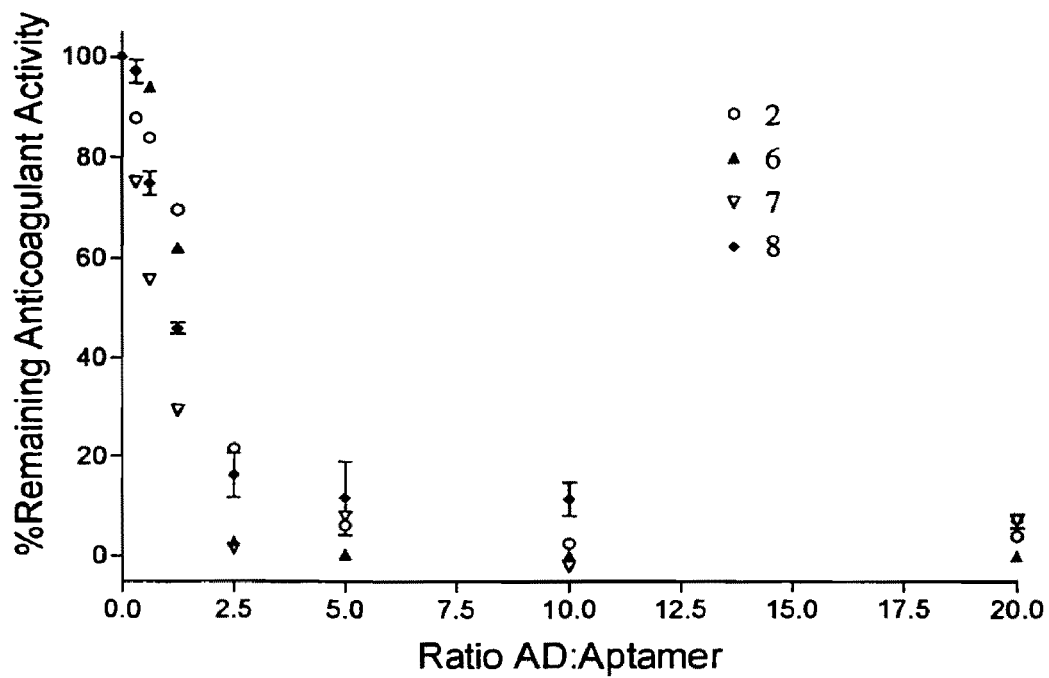
FIG. 3 is a graph of results of activated partial thromboplastin time (APTT) test assays of aptamers Apt 2 and 6-8 (right panel) and neutralizability by antidote (left panel).
Figure 3:
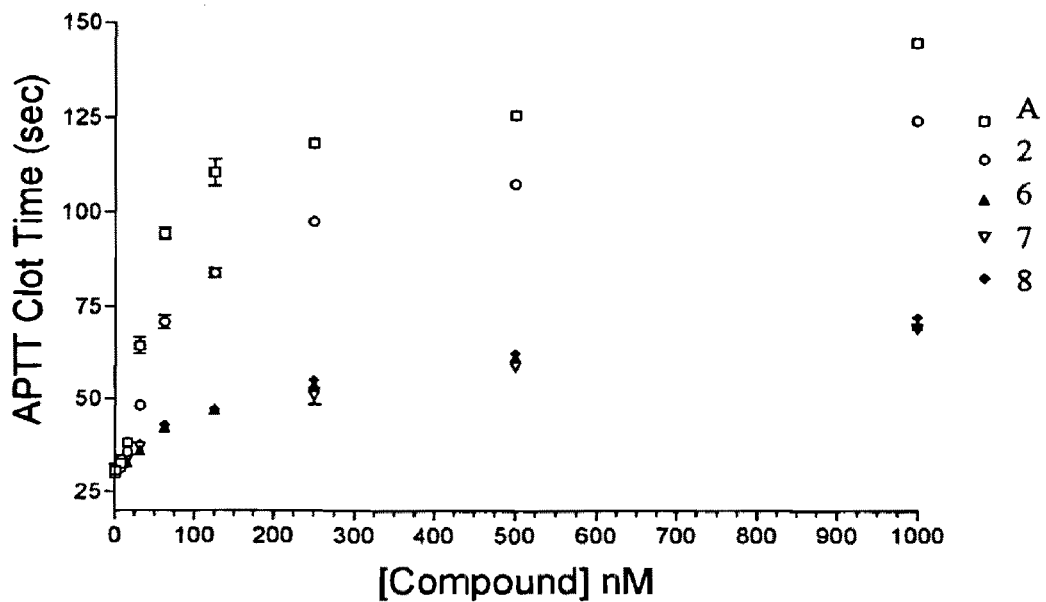
Figure 4:
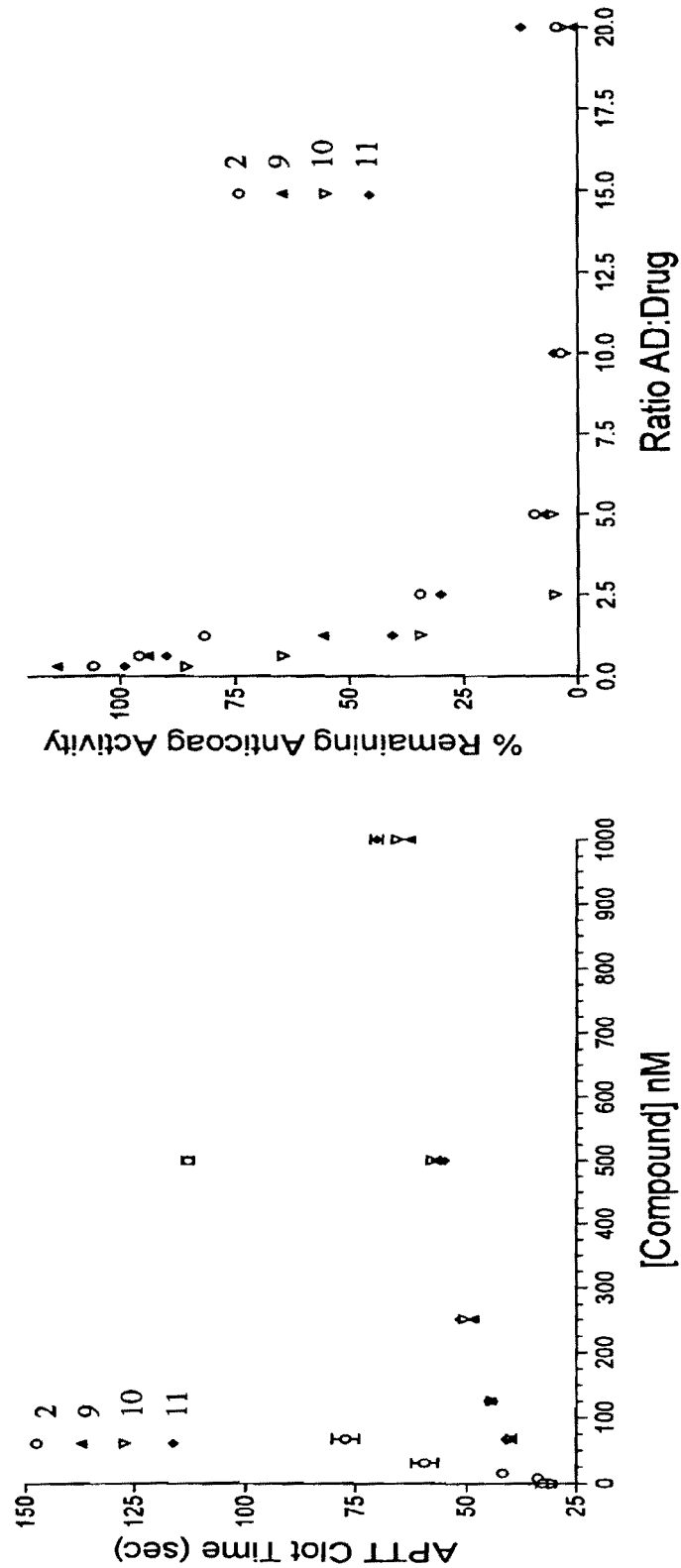
FIG. 4 is a graph of results of activated partial thromboplastin time (APTT) test assays of aptamers Apt 2 and 9-11 (left panel) and neutralizability by antidote (right panel).
Figure 5:
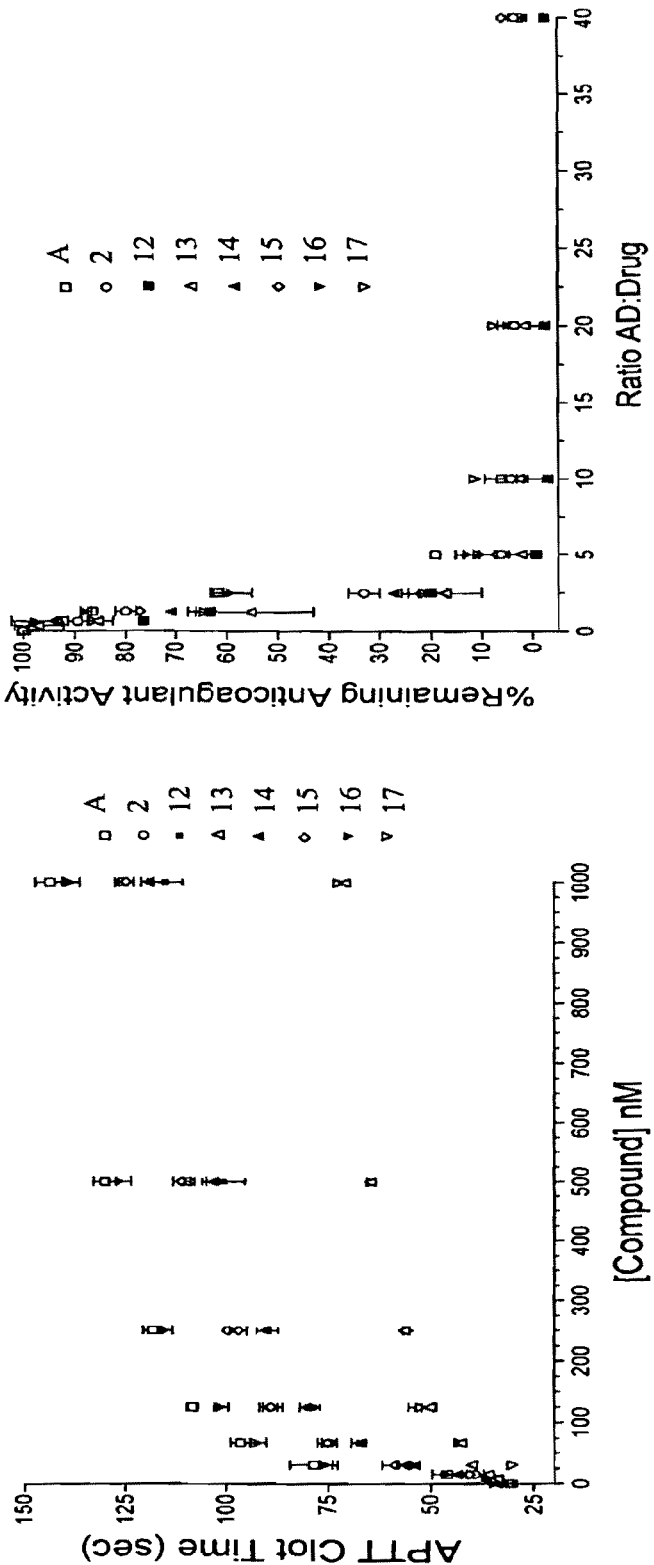
FIG. 5 is a graph of results of activated partial thromboplastin time (APTT) test assays of aptamers Apt A, 2 and 12-17 (left panel) and neutralizability by antidote (right panel).

Nucleic acid aptamers of the present invention can also be modified by varying the stem and loop sizes. Two families of aptamers with four, five, or six 2-O-methyl modified base pair stem 1 regions showed varying levels of anticoagulant activity and antidote control (see Example 2, FIGS. 3-5). Stem 1 mutants (FIG. 3) exhibit a loss of anticoagulant activity as measured in the APTT assay (FIGS. 4 and 5). All stem 1 variants exhibit less activity than the fully 2'-O-methyl purine/2' fluoro pyrimidine compound Apt 5, suggesting that one of the pyrimidines within stem 1 must contain a 2' fluoro sugar for the compound to retain potency. However, all exhibit similar activity levels suggesting stem length may not cause loss of activity. However, 5 base pair stem 1 constructs (Apt 10 and 7) do appear to be more readily antidote controlled than six base pair. Data suggests that a stem 1 of 5 base pairs may be preferable to those composed of 4, 6 or 7 base pairs to enhance antidote neutralization.

For targeting of an antidote, an improved aptamer can also be modified so as to include a single-stranded tail (3' or 5') in order to promote association with an oligonucleotide antidote. Suitable tails can comprise 1 to 20 nucleotides, preferably, 1-10 nucleotides, more preferably, 1-5 nucleotides and, most preferably, 3-5 nucleotides (e.g., modified nucleotides such as 2'-O-methyl sequences). Tailed aptamers can be tested in binding and bioassays (e.g., as described below) to verify that addition of the single-stranded tail does not disrupt the active structure of the aptamer. A series of oligonucleotides (for example, 2'-O-methyl oligonucleotides) that can form, for example, 1, 3 or 5 basepairs with the tail sequence can be designed and tested for their ability to associate with the tailed aptamer alone, as well as their ability to increase the rate of dissociation of the aptamer from, or association of the aptamer with, its target molecule. Scrambled sequence controls can be employed to verify that the effects are due to duplex formation and not non-specific effects.

The oligonucleotide antidotes can be administered directly (e.g., alone or in a liposomal formulation or complexed to a carrier, e.g. PEG)) (see for example, U.S. Pat. No. 6,147,204, U.S. Pat. No. 6,011,020). Surprisingly, the addition of a PEG molecule does not reduce aptamer binding to Factor IX the shorter the length of stem 1, and, in fact, a shorted stem 1 with pegylation do appears to increase neutralizability, providing a potentially more effective therapeutic. FIG. 10 shows the activity and neutralizability of a pegylated aptamer with a 5 base pair stem (Apt 19). Apt 19 possesses anticoagulant activity very similar to pegylated Apt16 with a 7 base pair stem 1, but ~90% of its activity can be neutralized with only a 2.5:1 excess of antidote to drug.

Therefore, in one embodiment, the improved aptamer or antidotes can be attached to a non-immunogenic, high molecular weight compound such as polyethylene glycol (PEG) or other water soluble pharmaceutically acceptable polymer as described herein. In one embodiment, the aptamer or antidote is associated with the PEG molecule through covalent bonds. Where covalent attachment is employed, PEG may be covalently bound to a variety of positions on the improved aptamer or antidote. In another embodiment, an oligonucleotide aptamer or antidote is bonded to the 5'-thiol through a maleimide or vinyl sulfone functionality. In one embodiment, a plurality of improved aptamers or antidotes can be associated with a single PEG molecule. The improved aptamers and antidotes can be the same or different sequences and modifications. In yet a further embodiment, a plurality of PEG molecules can be attached to each other. In this embodiment, one or more aptamers or antidotes to the same target or different targets can be associated with each PEG molecule. In embodiments where multiple aptamers or antidotes specific for the same target are attached to PEG, there is the possibility of bringing the same targets in close proximity to each other in order to generate specific interactions between the same targets. Where multiple aptamers or antidotes for specific for different targets are attached to PEG, there is the possibility of bringing the distinct targets in close proximity to each other in order to generate specific interactions between the targets. In addition, in embodiments where there are aptamers or antidotes to the same target or different targets associated with PEG, a drug can also be associated with PEG. Thus the complex would provide targeted delivery of the drug, with PEG serving as a Linker.

The aptamers or antidotes of the invention can also include other conjugate groups covalently bound to functional groups such as primary or secondary hydroxyl groups. Conjugate groups of the invention include polyamines, polyamides, polyethylene glycols, polyethers, groups that enhance the pharmacodynamic properties of oligomers, and groups that enhance the pharmacokinetic properties of oligomers. Groups that enhance the pharmacodynamic properties, in the context of this invention, include groups that improve oligomer bioavailability, enhance oligomer resistance to degradation, and/or strengthen sequence-specific hybridization with RNA.

In specific embodiments, the aptamers include the nucleotide sequences of any of the following sequences. ("A" is 2'OH A; "a" is 2'-O-methyl A; "G" is 2'-OH G; "g" is 2'-O-methyl G; "C" is 2'-Fluoro C; "c" is 2'-O-methyl C; "U" is 2'Fluoro U; "u" is 2'-O-methyl U; and "T" is inverted 2'H T.)

| SeqID | Code | Sequence |
|---|---|---|
| 20 | AptA | AUGGGGA CUAUACC GCG UAAUGC UGC C UCCCCAU T |
| 21 | Apt1 | aUgggga CUAUACCGCGUAAUGCUGCC UCCCCaU T |
| 22 | Apt2 | AUGGGGA CUaUaCC GCG UAAUGC UGC C UCCCCAU T |
| 23 | Apt3 | AUGGGGA CUAUACC gCg UAAUGC UgC C UCCCCAU T |
| 24 | Apt4 | AUGGGGA CUAUACC GCG UaaUgC UGC C UCCCCAU T |
| 25 | Apt5 | aUgggga CUaUaCC gCg UaaUgC UgC C UCCCCaU T |
| 26 | Apt6 | ggga CUaUaCCGCGUAAUGCUGCC uccc T |
| 27 | Apt7 | gugga CUaUaCCGCGUAAUGCUGCC uccac T |
| 28 | Apt8 | gaugga CUaUaCCGCGUAAUGCUGCC uccauc T |
| 29 | Apt9 | cuga CUaUaCCGCGUAAUGCUGCC ucag T |
| 30 | Apt10 | ccuga CUaUaCCGCGUAAUGCUGCC ucagg T |
| 31 | Apt11 | cucuga CUaUaCCGCGUAAUGCUGCC ucagag T |
| 32 | Apt12 | aUgggga CUaUaCCGCGUAAUGCUGCC UCCCCaU T |
| 33 | Apt13 | augggga CUaUaCCGCGUAAUGCUGCC uccccau T |
| 34 | Apt14 | gUgagga CUaUaCCGCGUAAUGCUGCC UCCUCaC T |
| 35 | Apt15 | gUgaggA CUaUaCCGCGUAAUGCUGCC UCCUCaC T |
| 36 | Apt16 | gugaggA CUaUaCCGCGUAAUGCUGCC Uccucac T |

-continued

| SeqID | Code  | Sequence |
|-------|-------|----------|
| 37    | Apt17 | gugagga CUaUaCCGCGUAAUGCUGCC uccucac T |
| 38    | Apt18 | gggA CUaUaCCGCGUAAUGCUGCC Uccc T |
| 39    | Apt19 | guggA CUaUaCCGCGUAAUGCUGCC Uccac T |
| 40    | Apt20 | gauggA CUaUaCCGCGUAAUGCUGCC Uccauc T |
| 41    | Apt21 | gugagga CUaUaCC GCG UAAUGC UGC C Uccucac T |
| 42    | Apt22 | gugaggA CUaUaCC gCg UAAUGC UgC C Uccucac T |
| 43    | Apt23 | gugaggA CUaUaCC GCG UaaUgC UGC C Uccucac T |
| 44    | Apt24 | gugaggA CUaUaCC gCg UaaUgC UgC C Uccucac T |
| 45    | Apt25 | gugaggA CUaUaCC GCg UaaUgC UgC C Uccucac T |
| 46    | Apt26 | gugaggA CUaUaCC gCa AUCG UgC C Uccucac T |
| 47    | Apt27 | gugaggA CUaUaCC GCA aUCg UGC C Uccucac T |
| 48    | Apt28 | gugaggA CUaUaCC gCa aUCg UgC C Uccucac T |
| 49    | Apt29 | gugaggA CUaUaCC GCa aUCg UgC C Uccucac T |
| 50    | Apt30 | CUaUaCC gCG UaaUgC UGC C Uccucac T |
| 51    | Apt31 | gugagga CUaUaCC gcg UaaUgC ugc C Uccucac T |
| 52    | Apt32 | gugagga CUaUaCC gcg UaaUgC UgC C Uccucac T |
| 53    | Apt33 | gugagga CUaUaCC gCg UaaUgC UGC C Uccucac T |
| 54    | Apt34 | gugagga CUaUaCC gCg UaaUgC uGc C Uccucac T |
| 55    | Apt35 | gugga CUaUaCC gCG UaaUgC UGC C Uccac T |
| 56    | Apt36 | gugga CUaUaCC gCG UaaUgC ugc C Uccac T |
| 57    | Apt37 | gugga CUaUaCC gCG UaaUgC UgC C Uccac T |
| 58    | Apt38 | gugga CUaUaCC gCg UaaUgC UGC C Uccac T |
| 59    | Apt39 | gugga CUaUaCC gCg UaaUgC uGc C Uccac T |

In one specific embodiment, the aptamer to Factor IX comprises, consists, or consists essentially of, the nucleotide sequence: gugga CUaUaCC gCg UaaUgC uGc C Uccac T (Apt39; SEQ ID NO: 59).

The improved aptamers described herein can be manufactured using techniques known in the art. For example, U.S. patents have issued that describe methods of large scale manufacturing that can be used to manufacture aptamers. Caruthers et al., for example, describe in U.S. Pat. Nos. 4,973,679; 4,668,777; and 4,415,732 a class of phosphoramidite compounds that are useful in the manufacture of oligonucleotides. In another series of patents, Caruthers et al. disclose a method of synthesizing oligonucleotides using an inorganic polymer support. See, e.g., U.S. Pat. Nos. 4,500,707, 4,458,066 and 5,153,319. In still another series of patents, Caruthers et al. discloses a class of nucleoside phosphorodithioates that can be used to manufacture oligonucleotides. See, e.g., U.S. Pat. Nos. 5,278,302, 5,453,496 and 5,602,244.

Methods of Use
Regulating Coagulation with an Improved Aptamer

The invention includes the use of improved aptamers to bind to FIX, FIXa, or the intrinsic tenase complex. The binding can be in vitro or in vivo. The result of the binding to FIX, FIXa or the tenase complex can be to inhibit the biological activity of the proteins or complex. The improved aptamers can be used to treat diseases such as deep venous thrombosis, arterial thrombosis, post surgical thrombosis, coronary artery bypass graft (CABG), percutaneous transdermal coronary angioplasty (PTCA), stroke, tumour metastasis, inflammation, septic chock, hypotension, ARDS, pulmonary embolism, disseminated intravascular coagulation (DIC), vascular restenosis, platelet deposition, myocardial infarction, angiogenesis, or the prophylactic treatment of mammals with atherosclerotic vessels at risk for thrombosis.

In one embodiment, the improved aptamer inhibits blood coagulation by binding to FIXa. The invention includes administering the aptamer of the invention to a mammal, for example, a human, in need thereof to inhibit blood coagulation. Another embodiment of the invention provides methods of using aptamers that are well suited for administration during a therapeutic regime.

A method of improved regulating coagulation in a mammal in need thereof is provided. In one embodiment, the method comprises: (a) administering to a warm-blooded vertebrate or mammal in need thereof, an effective amount of an improved aptamer that selectively binds coagulation pathway FIX, FIXa, or the intrinsic tenase complex, or inhibits a subunit of the intrinsic tenase complex (i.e. FIX, FIXa, FVIII binding to or activation of FX); (b) modulating the biological activity of the coagulation pathway factor in the warm-blooded vertebrate through the administering of the aptamer in step (a); and (c) providing an improved antidote to reverse the effects of the aptamer. In certain embodiments, the warm-blooded vertebrate or mammal is a human.

As used herein, the term "mammal" is meant to include any human or non-human mammal, including but not limited to porcine, ovine, bovine, rodents, ungulates, pigs, sheep, lambs, goats, cattle, deer, mules, horses, monkeys, dogs, cats, rats, and mice.

An important area for consideration is plasma half-life. Modifications can alter the half-life in vivo of the improved aptamers from a few minutes to 12 or more hours. The improved aptamers of the present invention can be used to treat percutaneous coronary interventions where vascular injury occurs at a specific time and place, yielding a sudden but relative brief prothrombotic stimulus. This may also be the case following carotid angioplasty. In another embodiment, the improved aptamers can be used in extracorporeal circulation utilized in coronary bypass grafting and hemodialysis. The latter condition is somewhat complex because of the inherent thrombogenicity of arteriovenous (AV) shunts. The aptamers of the invention also can be used to treat a venous thromboembolic disease, mechanical heart valve replacement, atrial fibrillation, and conceivably in either primary or secondary prevention of cardiovascular events among patients with prior events, an unfavorable risk profile, documented multibed vascular disease, vascular inflammation (early stages of atherosclerotic vasculopathy).

A method of treating cardiovascular disease in a warm-blooded vertebrate is also provided. The method comprises administering an effective amount of an improved aptamer to a vertebrate subject suffering from cardiovascular disease that selectively binds a coagulation pathway factor IX, IXa, or the intrinsic tenase complex, or inhibits a subunit of the intrinsic tenase complex (i.e. FIX, FIXa, FVIII binding to or activation of FX). Administration of the aptamer treats the cardiovascular disease in the vertebrate subject. The method can further comprise providing an antidote to reverse the effects of the improved aptamer by administration of an antidote.

The improved aptamers can be administered to mammals who require blood coagulation therapy. The invention provides methods of treating mammals with an aptamer to inhibit blood coagulation. The paired antidote can be administered to reverse the effects of the aptamer. A benefit of this discovery is that blood coagulation can be controlled in real time and does not rely on the mammal's own metabolism.

The compositions and methods of the present invention are particularly useful for preventing thrombosis in the circuit of cardiac bypass apparatus and in patients undergoing renal dialysis, and for treating patients suffering from or at risk of suffering from thrombus-related cardiovascular conditions, such as unstable angina, acute myocardial infarction (heart attack), cerebrovascular accidents (stroke), pulmonary embolism, deep vein thrombosis, arterial thrombosis, CABG surgery and disseminated intravascular coagulation.

In addition, the improved aptamers and antidotes of the present invention can inhibit other cardiovascular disease associated with FIX or FIX-regulated cascades. Coagulation plays an important part in ischaemic cardiovascular disease. Results of studies have shown that extremes in hypocoagulability protect against ischaemic cardiovascular disease. A mild decrease in coagulability found in hemophiliac patients can have a protective effect against fatal ischaemic heart disease (Sramek A, et al. (2003) *Lancet* 362(9381):351-4; Bilora F, et al. (1999) *Clin Appl Thromb Hemost.* 5(4):232-5.

The aptamers can be administered to prevent coagulation-induced inflammation. Inflammation is induced by thrombolytic therapy in patients with acute myocardial infarction (AMI), which might contribute to microvascular obstruction and reperfusion injury. Improved aptamers of the present invention can inhibit this early inflammatory response. In one embodiment, methods are provided to reduce the early inflammatory response in mammals that are in need thereof by administering the improved aptamers of the present invention.

The improved aptamers and antidotes of the present invention can be used to inhibit atherosclerosis. Some adverse events in atherosclerosis are associated with ruptured plaques, which are a major cause of morbidity and mortality associated with atherosclerosis. In addition to conventional coronary heart disease risk factors, coagulation factor IX activation peptide and fibrinogen can be positively associated with risk of coronary heart disease (R. Rosenberg et al. (2001) *Thromb Haemost* 86: 41-50; J A Cooper et al. (2000) *Circulation* 102: 2816-2822). The intrinsic pathway may significantly enhance thrombogenicity of atherosclerotic lesions after removal of the endothelial layer and exposure of SMCs and macrophages to blood flow (Ananyeva N M et al. (2002) *Blood* 99: 4475-4485). In addition, the improved aptamers can also be provided to prevent morbidity in mammals suffering from acute coronary syndrome (ACS) associated with inflammation.

In certain clinical scenarios, the contact pathway becomes the major pathway for blood clotting. These include surgical procedures where the blood products are removed from the body, such as contact of the blood with the cardiopulmonary bypass (CPB) circuit and oxygenator induces an inflammatory state during and post CPB. Genetic epidemiology and prospective clinical studies have linked the magnitude of the inflammatory response during coronary revascularization procedures with multiple adverse effects of CPB, including renal damage, atrial fibrillation, stroke, gut damage and neuronal damage. The inflammatory response induced by activation of the coagulation pathway is mediated by coagulation factors Xa and thrombin, which in addition to their role in blood clot formation, are themselves pro-inflammatory and mitogenic signaling proteins. The improved aptamers can also be administered to prevent adverse effects associated with post-angioplasty restenosis.

Regulating Coagulation with Improved Aptamer-Antidote Pairs

Among the many challenges of treating patients with thrombotic disorders or during a coagulation-inducing event is the potential risk of hemorrhage associated with anticoagulant drug therapy. The mechanisms which underlie bleeding risk are complex, but are unquestionably a function of drug variability (excess anticoagulant effect for the degree of thrombogenicity or extent of thrombus burden), relatively poor correlation between drug concentration and anticoagulant effect, wide-spread compromise of hemostatic barriers (platelet performance, vascular integrity, multiple phases of coagulation) and limited control of the anticoagulant's behavior.

At least three clinical scenarios exist in which the ability to rapidly reverse the activity of an antithrombotic or anticoagulant nucleic acid ligand is desirable. The first case is when anticoagulant or antithrombotic treatment leads to hemorrhage, including intracranial or gastrointestinal hemorrhage. While identifying safer target proteins may reduce this risk, the potential for morbidity or mortality from this type of bleeding event is such that the risk can not be overlooked. The second case is when emergency surgery is required for patients who have received antithrombotic treatment. This clinical situation arises in a percentage of patients who require emergency coronary artery bypass grafts (CABG) while undergoing percutaneous coronary intervention under the coverage of GPIIb/IIIa inhibitors. Current practice in this situation is to allow for clearance of the compound (for small molecule antagonists such as eptifibatide), which may take 2-4 hours, or platelet infusion (for Abciximab treatment). The third case is when an anticoagulant nucleic acid ligand is used during a cardiopulmonary bypass procedure. Bypass patients are predisposed to post operative bleeding. In each case, acute reversal of the anticoagulant effects of a compound via an antidote (e.g., an oligonucleotide antidote of the invention targeted to an anticoagulant or antithrombotic nucleic acid ligand) allows for improved, and likely safer, medical control of the anticoagulant or antithrombotic compound.

The applicants have discovered improved aptamer-antidote pairs that precisely regulate proteins in the blood coagulation cascade. In one embodiment, the antidotes of the invention are provided to a mammal in need thereof after the aptamers of the invention to reverse the effects of the aptamers. Aptamers and aptamer-antidote pairs can be administered in real time as needed based on various factors, including the progress of the patient, as well as the physician's discretion in how to achieve optimal therapy. Thus, this invention discloses an improved regulatable therapeutic regime in the course of nucleic acid ligand therapy for blood coagulation.

Individuals who are undergoing surgery also require the targeted modulation of coagulation that occurs through the use of the improved aptamers and antidotes of the present invention. In certain embodiments, the aptamers are administered to patients undergoing general surgery. In certain other embodiments, the aptamers are administered to patients with cardiovascular disease, which can include coronary heart disease. The patients can be undergoing treatment including bypass surgery or percutaneous coronary interventions. The mammals who can be treated with the aptamers of the present invention can also include patients who have had physical trauma that requires coagulation therapy.

Preoperative assessment of the patient can identify drug-induced, acquired, or inherited coagulation defects. The main attention in anticoagulant therapy is directed to the perioperative period. A further, often overlooked, management strategy in treating major coagulopathies is the consideration of the cost and half-lives of the coagulation factors in individual blood components. Prevention of bleeding has become possible by manipulation of the control of coagulation and inflammatory processes. Additionally, because diagnosis of patients is often difficult, the modulatable improved aptamers and antidote pairs of the present invention are particularly useful in ensuring that, in case of incorrect diagnosis and treatment, treatment can immediately be disabled. For example, the symptoms of coronary infarction can closely mimic those of an acute coronary dissection. See Scarabeo et al. (2002) *Italian Heart Journal* 3: 490-494. A diagnosis of coronary infarction immediately calls for an anticoagulant, which is counterindicated in acute coronary dissection. With the improved aptamer-antidote pairs described herein, a mistake by a health care provider can readily be reversed.

Agents that restore vascular patency in stroke also increase the risk of intracerebral hemorrhage (ICH). As Factor IXa is a key intermediary in the intrinsic pathway of coagulation, targeted inhibition of Factor IXa-dependent coagulation can inhibit microvascular thrombosis in stroke without impairing extrinsic hemostatic mechanisms that limit ICH. The improved aptamers and antidotes of the present invention can be used to inhibit stroke associated with cardiovascular disease and surgery.

Administration

The present method for treating cardiovascular disease in a tissue contemplates contacting a tissue in which cardiovascular disease is occurring, or is at risk for occurring, with a composition comprising a therapeutically effective amount of an improved aptamer capable of binding a coagulation factor as well as providing an improved antidote to reverse the effects of the aptamer by administration of an antidote. Thus, the method comprises administering to a patient a therapeutically effective amount of a physiologically tolerable composition containing the RNA aptamer as well as a method to provide an antidote to reverse the effects of the aptamer by administration of an antidote.

The dosage ranges for the administration of the antidote depend upon the form of the antidote, and can be assessed by a physician or other health care provider. Generally, the dosage will vary with the age, condition, sex and extent of the disease in the patient and can be determined by one of skill in the art. The individual physician in the event of any complication can also adjust the dosage.

Generally, a therapeutically effective amount is an amount of a antidote sufficient to produce a measurable modulation of the effects of the nucleic acid ligand, including but not limited to a coagulation-modulating amount or an inflammation-modulating amount.

Preferred modes of administration of the improved aptamers of the present invention are parenteral, intravenous, intradermal, intra-articular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump or via catheter. In one embodiment, the agent and carrier are administered in a slow release formulation such as an implant, bolus, microparticle, microsphere, nanoparticle or nanosphere.

The antidotes of the present invention can be preferably administered parenterally by injection or by gradual infusion over time. Although the tissue to be treated can typically be accessed in the body by systemic administration and therefore most often treated by intravenous administration of therapeutic compositions, other tissues and delivery techniques are provided where there is a likelihood that the tissue targeted contains the target molecule. Thus, antidotes of the present invention are typically administered orally, topically to a vascular tissue, intravenously, intraperitoneally, intramuscularly, subcutaneously, intra-cavity, transdermally, and can be delivered by peristaltic techniques. As noted above, the pharmaceutical compositions can be provided to the individual by a variety of routes such orally, topically to a vascular tissue, intravenously, intraperitoneally, intramuscularly, subcutaneously, intra-cavity, transdermally, and can be delivered by peristaltic techniques. Representative, non-liming approaches for topical administration to a vascular tissue include (1) coating or impregnating a blood vessel tissue with a gel comprising a nucleic acid ligand, for delivery in vivo, e.g. by implanting the coated or impregnated vessel in place of a damaged or diseased vessel tissue segment that was removed or by-passed; (2) delivery via a catheter to a vessel in which delivery is desired; (3) pumping a nucleic acid ligand composition into a vessel that is to be implanted into a patient. Alternatively, the nucleic acid ligand can be introduced into cells by microinjection, or by liposome encapsulation. Advantageously, nucleic acid ligands of the present invention can be administered in a single daily dose, or the total daily dosage can be administered in several divided doses. Thereafter, the antidote is provided by any suitable means to alter the effect of the nucleic acid ligand by administration of the antidote.

Compositions

The aptamers and antidotes of the invention can be formulated into pharmaceutical compositions that can include, in addition to an improved aptamer, a antidote or modulator, and a pharmaceutically acceptable carrier, diluent or excipient. The precise nature of the composition will depend, at least in part, on the nature of the improved aptamer and antidote and the route of administration. Optimum dosing regimens can be readily established by one skilled in the art and can vary with the improved aptamer, the antidote combination, the patient and the effect sought.

For standard information on pharmaceutical formulations, see Ansel, et al., Pharmaceutical Dosage Forms and Drug Delivery Systems, Sixth Edition, Williams & Wilkins, 1995. The therapeutic compositions comprising aptamers and antidotes of the present invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e. carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Pharmaceutically useful compositions comprising an aptamer or antidote of the present invention can be formulated according to known methods such as by the admixture of a pharmaceutically acceptable carrier. Examples of such carriers and methods of formulation can be found in Remington's Pharmaceutical Sciences. To form a pharmaceutically acceptable composition suitable for effective administration, such compositions will contain an effective amount of the aptamer. Such compositions can contain admixtures of more than one aptamers or antidotes.

The effective amount of an improved aptamer of the invention can vary according to a variety of factors such as the individual's condition, weight, sex and age. Other factors include the mode of administration. Generally, the compositions will be administered in dosages adjusted for body weight, e.g., dosages ranging from about 0.1 mg/kg body weight to about 100 mg/kg body weight. In specific embodiments, the dosages are about 0.5 mg/kg body weight to 50 mg/kg body weight. In specific embodiments, the dosage is between 0.1, 0.2, 0.3, 0.4, 0.5, 0.6, 0.7, 0.8, 0.9, and 1 mg/kg body weight, and any dosage in between. Specific dosage units can range from 1 ng to 1 g, but are more conventionally about 0.01 µg, 0.1 µg, 1 µg, 10 µg, 100 µg, 500 µg, or 1 g or any amount in between.

The effective amount of antibody being delivered to a patient will vary according to a variety of factors such as the individual's condition, weight, sex, age and amount of nucleic acid ligand administered. In one embodiment, the antidote ranges from 0.5-50 mg/kg. In another embodiment, the amount of antidote being delivered ranges from 0.5-10, 0.5-5, 1-10 or 1-5 mg/kg. In general, the amount of antidote being delivered is not less than the amount of aptamer being delivered. Typically, the amount of antidote is from about 1 to about 20 times the amount of aptamer. In certain embodiments, the antidote is about 1, 2, 3, 4, 5, 6, 7, 8, 9, or 10 times the amount of aptamer delivered to a patient.

Improved combinations of aptamers and antidotes in pharmaceutical compositions are administered in therapeutically effective amounts, that is, in amounts sufficient to generate a coagulation-modulating response, or in a prophylactically effective amounts, that is in amounts sufficient to prevent a coagulation factor from acting in a coagulation cascade. The therapeutically effective amount and prophylactically effective amount can vary according to the modulator. The pharmaceutical composition can be administered in single or multiple doses.

Because the activity of the improved antidotes is lasting, once the desired level of modulation of the nucleic acid ligand by the antidote is achieved, infusion of the antidote can be terminated, allowing residual antidote to clear the human or animal. This allows for subsequent re-treatment with the nucleic acid ligand as needed. Alternatively, and in view of the specificity of the antidotes of the invention, subsequent treatment can involve the use of a second, different improved aptamer/antidote pair.

Antidotes synthesized or identified according to the methods disclosed herein can be used alone at appropriate dosages defined by routine testing in order to obtain optimal modulation of nucleic acid ligand activity in coagulation, while minimizing any potential toxicity. In addition, co-administration or sequential administration of other agents can be desirable. For combination treatment with more than one active agent, where the active agents are in separate dosage formulations, the active agents can be administered concurrently, or they each can be administered at separately staggered times.

The dosage regimen utilizing the improved aptamers and antidotes of the present invention is selected in accordance with a variety of factors including type, species, age, weight, sex and medical condition of the patient; the severity of the condition to be treated; the route of administration; the renal and hepatic function of the patient; and the particular combination employed. A physician of ordinary skill can readily determine and prescribe the effective amount of the aptamer required to prevent, counter or arrest the progress of the condition. Optimal precision in achieving concentrations of the combination within the range that yields efficacy without toxicity requires a regimen based on the kinetics of the aptamer and antidote's availability to target sites. This involves a consideration of the distribution, equilibrium, and elimination of the modulator.

In the methods of the present invention, the combinations described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that can be employed include glycerin and the like. For parenteral administration, sterile suspensions and solutions are desired. Isotonic preparations that generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 mydstyl propionate, and the like, to form, e.g. alcoholic solutions, topical cleansers, cleansing creams, skin gels, skin lotions, and shampoos in cream or gel formulations.

The aptamers and antidotes of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The aptamers and antidotes of the present invention can also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the aptamers and antidotes of the present invention can be coupled (preferably via a covalent linkage) to a class of biodegradable polymers useful in achieving controlled release of a drug, for example, polyethylene glycol (PEG), polylactic acid, polyepsilon caprolactone, polyhydroxy butyric acid, polyorthoesters, polyacetals, polydihydro-pyrans, polycyanoacrylates and cross-linked or amphipathic block copolymers of hydrogels. Cholesterol and similar molecules can be linked to the aptamers to increase and prolong bioavailability.

In certain embodiments of this invention, the complex comprises a liposome with a targeting nucleic acid ligand (s) associated with the surface of the liposome and an encapsulated therapeutic or diagnostic agent. Preformed liposomes can be modified to associate with the nucleic acid ligands. For example, a cationic liposome associates through electrostatic interactions with the nucleic acid. Alternatively, a nucleic acid attached to a lipophilic compound, such as cholesterol, can be added to preformed liposomes whereby the cholesterol becomes associated with the liposomal membrane. Alternatively, the nucleic acid can be associated with the liposome during the formulation of the liposome. Preferably, the nucleic acid is associated with the liposome by loading into preformed liposomes.

EXAMPLES

Tests of Aptamers for Coagulation

The following tests are used to assess the capacity of modified aptamers and antidotes to inhibit coagulation factors.

The Activated Clotting Time Test (ACT) is a screening test that resembles the activated partial thromboplastin time (APTT) test, but is performed using fresh whole blood samples. ACT can be to monitor a patient's coagulation status in connection with clinical procedures, such as those that involve the administration of high doses of heparin (e.g., CPB and PTCA).

The Activated Partial Thromboplastin Time Test (APTT) is a common central laboratory test, typically performed using an automated coagulometer, for example Diagnostica Stago's STA coagulometer (MDA/96/23), or another coagulometer produced by this company or otherwise known in the art. The test is performed using a plasma sample, in which the intrinsic pathway is activated by the addition of phospholipid, an activator (ellagic acid, kaolin, or micronized silica), and $Ca^{2+}$.

The bleeding time test can be used for the diagnosis of hemostatic dysfunction, von Willebrand's disease, and vascular disorders. It also can be used to screen for platelet abnormalities prior to surgery. The test is performed by making a small incision on the forearm and wicking away the blood from the wound site. The time it takes for bleeding to stop is recorded and in control subjects is approximately 3.5 minutes. Prolongation of the bleeding time is indicative of qualitative or quantitative platelet defects.

The Prothrombin Time Test (PT), which was first described by Quick in 1935, measures the tissue factor-induced coagulation time of blood or plasma. It is used as a screening test to evaluate the integrity of the extrinsic coagulation pathway, and is sensitive to coagulation factors I, II, V, VII, and X. The test can be performed by adding thromboplastin and $Ca^{2+}$ to a patient sample and measuring the time for clot formation. A prolonged clotting time suggests the presence of an inhibitor to, or a deficiency in, one or more of the coagulation factors of the extrinsic pathway. But PT clotting time can also be prolonged for patients on warfarin therapy, or for those with vitamin K deficiency or liver dysfunction. The PT test can provide an assessment of the extrinsic coagulation pathway, and is widely used to monitor oral anticoagulation therapy.

The Thrombin Clotting Time Test (TCT) measures the rate of a patient's clot formation compared to that of a normal plasma control. The test can be performed by adding a standard amount of thrombin to a patient's plasma that has been depleted of platelets, and measuring the time required for a clot to form. This test has been used as an aid in the diagnosis of disseminated intravascular coagulation (DIC) and liver disease.

There are also a number of tests that may be used in the diagnosis of a patient's coagulative status. These fall into two categories: complex tests, some of which are based on the screening tests outlined above, and immunoassays. Complex Tests include specific factor assays based on laboratory tests, such as the APTT, PT, and TCT tests. One assay measures the level of the activation Factor IXa or the Factor IXa-antithrombin III complex. These measurements are used to determine the levels of factor IXa or factor VII-tissue mediated complex. Assays for activated protein C resistance, antithrombin, protein C deficiency, and protein S deficiency are also part of this group. Asymptomatic individuals who have heterogeneous deficiencies of proteins C and S, and resistance to activated protein C, have significantly elevated levels of the prothrombin fragment F1.2 compared to controls.

Example 1

Substitution of 2'-O-methyl for 2'-O-methyl for 2'-hydroxyl Sugars in Sectors 2'-Hydroxyl purines were substituted with 2'-O-methyl purines in the 4 secondary structure units of in which purine residues are present: Stem 1 (Apt 1); Loop 1 (Apt 2); Stem 2 (Apt 3); Loop 2 (Apt 4) (see FIG. 1A).

Procedure: The anticoagulant activity of AptA derivatives Apt 1-5 was evaluated in standard APTT coagulation assays over compound concentrations ranging from 1 uM to low nanomolar (FIG. 2). The "neutralizability" of Apt1-5 was evaluated in standard APTT antidote assays over AptA antidote concentrations (AptA AD; see sequence listings) ranging from 5 uM and down (FIG. 2). For these assays, the concentration of AptA and derivatives was fixed at 125 nM.

Apt 4 showed gain of anticoagulant activity (FIG. 2); Apt 1-3 showed moderate loss of activity; and Apt 5 showed severe loss of activity. Apt 1-3 exhibit enhanced neutralization, suggesting that introduction of 2'-O-methyl residues within the antidote binding site improves the ability of the antidote oligonucleotide to bind to the aptamer.

Sequence Listings:

```
1) AptA     Length: 35  (5'-3') sequence:
                        AUGGGGA CUAUACC GCG UAAUGC UGC C UCCCCAU T
                        (SEQ ID NO: 20)

1) Apt 1    Length: 35  (5'-3') sequence:
                        aUgggga CUAUACCGCGUAAUGCUGCC UCCCCaU T
                        (SEQ ID NO: 21)

3) Apt 2    Length: 35  (5'-3') sequence:
                        AUGGGGA CUaUaCC GCG UAAUGC UGC C UCCCCAU T
                        (SEQ ID NO: 22)

4) Apt 3    Length: 35  (5'-3') sequence:
                        AUGGGGA CUAUACC gCg UAAUGC UgC C UCCCCAU T
                        (SEQ ID NO: 23)

5) Apt 4    Length: 35  (5'-3') sequence:
                        AUGGGGA CUAUACC GCG UaaUgC UGC C UCCCCAU T
                        (SEQ ID NO: 24)

6) Apt 5    Length: 35  (5'-3') sequence:
                        aUgggga CUaUaCC gCg UaaUgC UgC C UCCCCaU T
                        (SEQ ID NO: 25)

7) AptA AD  Length: 17  (5'-3') sequence:
                        cgcgguauaguccccau
                        (SEQ ID NO: 1)
```

"A": 2'OH Adenine; "a": 2'-O-methyl Adenine; "G": 2'OH Guanine; "g": 2'-O-methyl Guanine; "C": 2'Fluro-Cytidine; "c": 2'-O-methyl Cytidine; "U": 2'Fluoro-Uridine; "u": 2'-O-methyl Uridine; "T": inverted 2'H Thymidine.

Example 2

Stem 1 Modifications

Two "families" of stem 1 variants were designed (Apt 6-8 and 9-11; FIG. 1B) consisting of 4, 5, and 6 basepair stems. All constructs were designed in the Apt-2 background. Stem 1 sequences were evaluated for the ability to design complementary antidote oligonucleotides to them such that the antidotes contain minimal secondary structure, and for the ability of the aptamer to assume the proper secondary structure.

Stems were wholly 2'-O-methyl modified. Antidote oligonucleotides were designed specific for Apt 6-11 that bind to their respective target aptamer in the same register as AptA AD (see sequence listings below).

Experiments: The anticoagulant activity of Apt 6-11 was evaluated in standard APTT coagulation assays over compound concentrations ranging from 1 uM to low nanomolar. The antidote control of Apt 6-11 was evaluated in standard APTT antidote assays over antidote concentrations ranging from 5 uM and down. For these assays, the concentration of Apt 2, and Apt 6-11 was set at 250 nM (as opposed to 125 nM for standard AptA and Apt 2 experiments).

Apt 6-8 exhibit loss of anticoagulant activity (FIG. 3), however, all exhibit similar activity levels. Thus stem length is not be the main cause for loss of activity. The 5 base pair stem 1 constructs (Apt 10 and Apt 7) do appear to be more neutralizable than Apt 2 (FIGS. 3 and 4). Data suggests that a stem 1 of 5 base pairs may be preferable to those composed of 4, 6 or 7 base pairs to enhance antidote neutralization.

Sequence Listings:

```
1) Apt 6    Length: 29   (5'-3'): ggga CUaUaCCGCGUAAUGCUGCC uccc T
                         (SEQ ID NO: 26)

2) Apt 7    Length: 31   (5'-3'): gugga CUaUaCCGCGUAAUGCUGCC uccac T
                         (SEQ ID NO: 27)

3) Apt 8    Length: 33   (5'-3'): gaugga CUaUaCCGCGUAAUGCUGCC uccauc T
                         (SEQ ID NO: 28)

4) Apt 9    Length: 29   (5'-3'): cuga CUaUaCCGCGUAAUGCUGCC ucag T
                         (SEQ ID NO: 29)

5) Apt 10   Length: 31   (5'-3'): ccuga CUaUaCCGCGUAAUGCUGCC ucagg T
                         (SEQ ID NO: 30)

6) Apt 11   Length: 33   (5'-3'): cucuga CUaUaCCGCGUAAUGCUGCC ucagag T
                         (SEQ ID NO: 31)

7) Apt 6 AD  Length: 14  (5'-3'): cgcgguauaguccc
                         (SEQ ID NO: 2)

8) Apt 7 AD  Length: 15  (5'-3'): cgcgguauaguccac
                         (SEQ ID NO: 3)

9) Apt 8 AD  Length: 16  (5'-3'): cgcgguauaguccauc
                         (SEQ ID NO: 4)

10) Apt 9 AD  Length: 14 (5'-3'): cgcgguauagucag
                         (SEQ ID NO: 5)

11) Apt 10 AD Length: 15 (5'-3'): cgcgguauagucagg
                         (SEQ ID NO: 6)

12) Apt 11 AD Length: 16 (5'-3'): cgcgguauagucagag
                         (SEQ ID NO: 7)
```

"A": 2'OH Adenine; "a": 2'-O-methyl Adenine; "G": 2'OH Guanine; "g": 2'-O-methyl Guanine; "C": 2'Fluro-Cytidine; "c": 2'-O-methyl Cytidine; "U": 2'Fluoro-Uridine; "u": 2'-O-methyl Uridine; "T": inverted 2'H Thymidine.

Example 3

Stem 1 Sugar Chemistry

The anticoagulant activity of Apt 12-17 was evaluated in standard APTT coagulation assays over compound concentrations ranging from 1 uM to low nanomolar. The "neutralizability" of Apt 12-17 was evaluated in standard APTT antidote assays over antidote concentrations ranging from 5 uM and down. For Apt 12, 14, 15, and 16, the aptamer concentration was fixed at 125 nM in these assays, and for Apt 13 and 17, the aptamer concentration was fixed at 250 nM.

Comparison of the anticoagulant activity of Apt 12 with Apt 13 and Apt17 (FIG. 5) demonstrates that the loss of activity observed for Apt6-11 is due to the presence of 2'-O-methyl substitutions at one or more critical residues. Comparison of the anticoagulant activity of Apt14 to Apt12 indicates that the stretch of 4 consecutive guanosines within stem 1 can be altered without a significant impact on anticoagulant activity. Comparison of Apt15 and 16 with Apt 2, 12 and 17 a) demonstrates that the presence of 2'-O-methyl sugars at each position within stem 1 except for the closing A-U pair at the top of stem 1 enhances activity; b) demonstrates that the sugar of the U in this base pair must be 2' fluoro for the aptamer to retain potency; and c) suggests that the sugar of the A in this base pair can be a 2'-O-methyl sugar without a significant impact on anticoagulant activity. In fact, Apt 16 retains essentially full potency.

Comparison of the neutralization of Apt14-16 with Apt14/AD suggests that the antidote can more readily bind the aptamer when stem 1 is a 2'-O-methyl-2' fluoro stem as opposed to when both strands of the duplex contain largely 2'-O-methyl residues. Apt21 was designed in which the sugar of the A at the stop of stem 1 is 2'-O-methyl substituted (FIG. 1). Substitution of a 2'-O-methyl sugar at this adenosine residue is well tolerated in the background of a largely 2'-O-methyl stem (FIG. 6). Antidote neutralization of Apt 21 is enhanced as compared to Apt16 (see especially the 2.5:1 and 5:1 AD:Drug data points in FIG. 4).

Sequence Listings:

```
1) Apt2    Length: 35   (5'-3') sequence:
                        aUgggga CUaUaCCGCGUAAUGCUGCC UCCCCaU T
                        (SEQ ID NO: 32)

2) Apt13   Length: 35   (5'-3') sequence:
                        augggga CUaUaCCGCGUAAUGCUGCC ucccccau T
                        (SEQ ID NO: 33)

3) Apt14   Length: 35   (5'-3') sequence:
                        gUgagga CUaUaCCGCGUAAUGCUGCC UCCUCaC T
                        (SEQ ID NO: 34)
```

-continued

```
4) Apt15      Length: 35  (5'-3') sequence:
                          gUgaggA CUaUaCCGCGUAAUGCUGCC UCCUCaC T
                          (SEQ ID NO: 35)

5) Apt16      Length: 35  (5'-3') sequence:
                          gugaggA CUaUaCCGCGUAAUGCUGCC Uccucac T
                          (SEQ ID NO: 36)

6) Apt17      Length: 35  (5'-3') sequence:
                          gugagga CUaUaCCGCGUAAUGCUGCC uccucac T
                          (SEQ ID NO: 37)

7) Apt14AD    Length: 17  (5'-3') sequence: cgcgguauaguccucac
                          (SEQ ID NO: 8)

8) Apt21      Length: 35  (5'-3') sequence:
                          gugagga CUaUaCC GCG UAAUGC UGC C Uccucac T
                          (SEQ ID NO: 41)
```

"A": 2'OH Adenine; "a": 2'-O-methyl Adenine; "G": 2'OH Guanine; "g": 2'-O-methyl Guanine; "C": 2'Fluro-Cytidine; "c": 2'-O-methyl Cytidine; "U": 2'Fluoro-Uridine; "u": 2'-O-methyl Uridine; "T": inverted 2'H Thymidine.

Example 4

Reducing Length of Stem 1

The anticoagulant activity of Apt 18-20 was evaluated in standard APTT coagulation assays over compound concentrations ranging from 1 uM to low nanomolar. The "neutralizability" of Apt 18-20 was evaluated in standard APTT antidote assays over antidote concentrations (Antidote 6, 7 and 8 for 18-20 respectively) ranging from 5 uM and down. The aptamer concentration was fixed at 125 nM in these assays.

Figure 8:
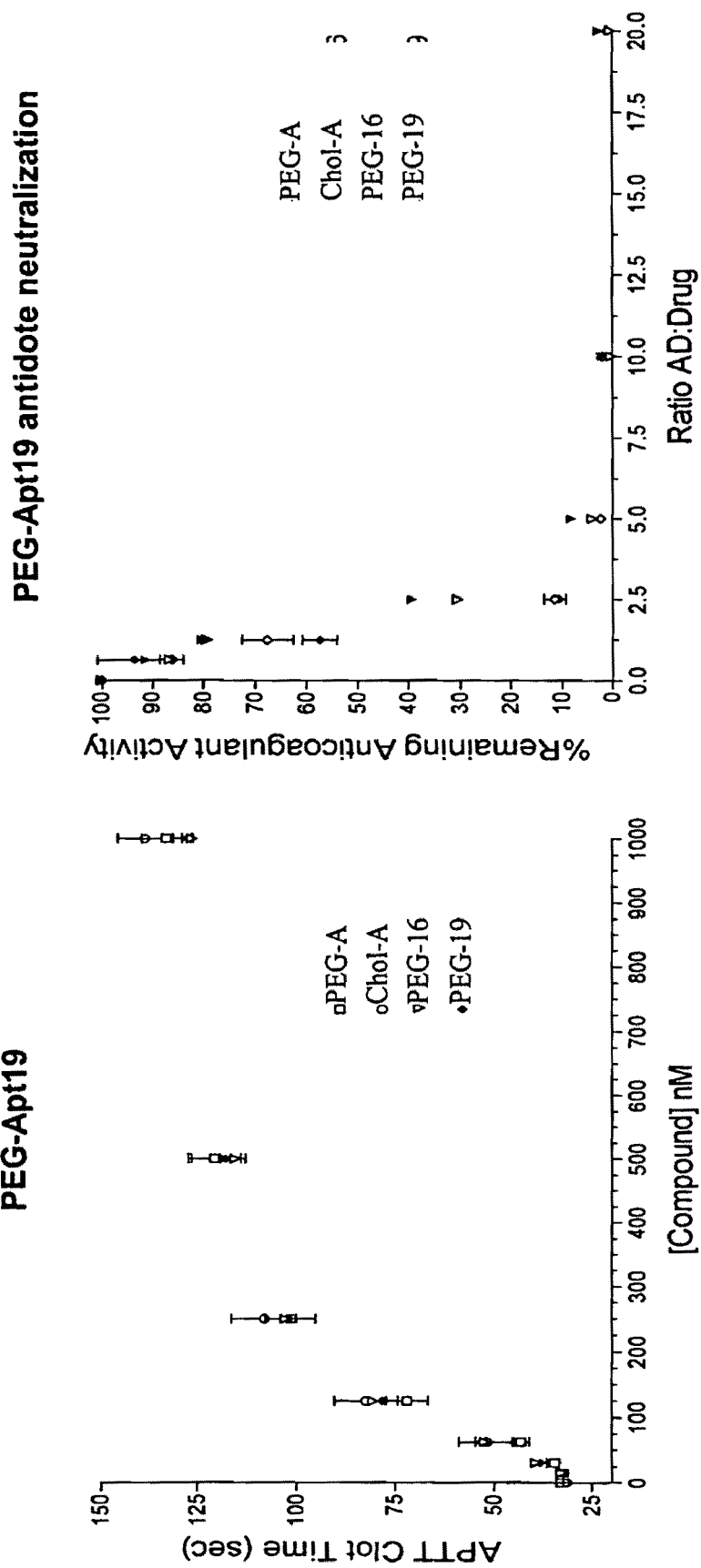
FIG. 8 is a graph of results of activated partial thromboplastin time (APTT) test assays of pegylated AptA compared to pegylated Apt 16 and 19 and cholesterol-modified Apt A (chol-A). Left panel is aptamer control of coagulation factor IX and right panel is neutralizability by antidote.

Each of the aptamers (Apt 18-20) is a potent anticoagulant, as or more potent than Apt 2 (FIG. 7). Furthermore, all three are readily neutralized by their respective antidote oligonucleotides. Apt 19 was evaluated for anticoagulant activity of a pegylated version. PEG Apt 19 and, for comparison, PEG-Apt 16 are used (PEG is a 40 KDa polyethylene glycol mPEG2-NHS ester (MW 40 kDa; Nektar/Shearwater 2Z3XOT01), appended to the 5' end via conjugation to a C6 amino linker added to the aptamer during solid phase synthesis). FIG. 8 indicates that the length of stem 1 does not affect how 40 KDa PEG addition impacts the activity of AptA and AptA derivatives. The anticoagulant activity of PEG Apt 19 and 16 is essentially identical to the anticoagulant activity of both pegylated (PEG AptA) and cholesterol-modified (CH-AptA) versions of the parental AptA sequence. In addition, like Apt 19, PEG Apt 19 is more readily neutralized by its matched antidote (7 AD) than AptA, Apt 16 or any of the PEG or cholesterol-modified versions of these compounds. FIG. 8 shows approximately 90% reversal of PEG Apt 19 at 2.5:1 AD:Aptamer. Looked at as an absolute change in APTT rather than on a % reversal basis, the APTT of plasma treated with PEG Apt 19+2.5:1 7AD:Aptamer is only 4-5 seconds above baseline.

Sequence Listings:

```
1) Apt18        Length: 29  (5'-3') sequence:
                            gggA CUaUaCCGCGUAAUGCUGCC Uccc T
                            (SEQ ID NO: 38)

2) Apt19        Length: 31  (5'-3') sequence:
                            guggA CUaUaCCGCGUAAUGCUGCC Uccac T
                            (SEQ ID NO: 39)

3) Apt20        Length: 33  (5'-3') sequence:
                            gauggA CUaUaCCGCGUAAUGCUGCC Uccauc T
                            (SEQ ID NO: 40)

4) PEG Apt 16   Length: 35  (5'-3') sequence: P-L-gugaggA
                            CUaUaCCGCGUAAUGCUGCC Uccucac T 5) PEG Apt 19   Length: 31  (5'-3') sequence: P-L-guggA
                            CUaUaCCGCGUAAUGCUGCC Uccac T
```

"A": 2'OH Adenine; "a": 2'-O-methyl Adenine; "G": 2'OH Guanine; "g": 2'-O-methyl Guanine; "C": 2'Fluro-Cytidine; "c": 2'-O-methyl Cytidine; "U": 2'Fluoro-Uridine; "u": 2'-O-methyl Uridine; "T": inverted 2'H Thymidine; "P": mPEG2-NHS ester MW 40 kDa (Nektar/Shearwater 2Z3XOT01); "L": C6 amino linker

Example 5

Stem 2 and Loop 2 Substitutions

Two series of variants evaluating the optimal sugar composition for the residues in stem 2 and loop 2. The first series in the Apt 16 background. The second series in the Apt 16 background, but substituting the tetraloop found in FIXa aptamer 9.20 (see Rusconi et al Nature 419, p. 90-94, 2002 and FIG. 1) for the hexanucleotide loop found in AptA. Studies on Apt 4 indicated that 2'-O-methyl purine substitution within loop 2 led to an enhancement in AptA potency, whereas 2'-O-methyl purine substitution within stem 2 led to a modest loss of potency, and that simultaneous 2'-O-methyl purine substitution within stem 2 and loop 2 in the context of a 2'-O-methyl purine stem 1 led to a significant loss of AptA potency (Apt 5). Therefore, independently substitute 2'-O-methyl purines in stem 2 (Apt 22, 26) and loop 2 (Apt 23, 27) (FIG. 9). Re-evaluated complete 2'-O-methyl substitution of purines within stem 2 and loop 2 (Apt 24, Apt 28) but leave the G at the base of stem 2 as a 2' hydroxyl (Apt 25, 29) in the event that a 2' hydroxyl is required at this position.

The anticoagulant activity of Apt 22-29 was evaluated in standard APTT coagulation assays over compound concentrations ranging from 1 uM to low nanomolar. The "neutralizability" of Apt 22-29 was evaluated in standard APTT antidote assays over antidote concentrations ranging from 5 uM and down. The aptamer concentration was fixed at 125 nM in these assays, except for Apt 24 in which the aptamer concentration was fixed at 250 nM.

As previously observed with Apt 3, substitution of 2'-O-methyl purines within loop 2 leads to enhanced potency (Apt 23, compare Apt 23 to 16) (FIG. 9). Likewise, substitution of 2'-O-methyl purines into stem 2 leads to a moderate loss of activity (Apt 22, 24) (FIG. 14). Apt 24 is significantly more potent than Apt 5. Maintenance of a 2' hydroxyl on the G residue at the base of stem 2 (Apt 25) does not lead to enhanced activity as compared to Apt 24, indicating that a) substitution of a 2'-O-methyl sugar at this residue is not the problem within Apt 22 and 24 and b) the sugar on this residue can be 2'-O-methyl. Substitution of the 9.20 tetraloop for the hexanucleotide loop present in AptA led to a loss of activity (Apt 26-29). Antidote neutralization of Apt 23 is reduced as compared to Apt 16, but still equivalent to AptA.

Sequence Listings:

```
1) Apt22 Length: 35  (5'-3') sequence:
                     gugaggA CUaUaCC gCg UAAUGC UgC C Uccucac T
                     (SEQ ID NO: 42)

2) Apt23 Length: 35  (5'-3') sequence:
                     gugaggA CUaUaCC GCG UaaUgC UGC C Uccucac T
                     (SEQ ID NO: 43)

3) Apt24 Length: 35  (5'-3') sequence:
                     gugaggA CUaUaCC gCg UaaUgC UgC C Uccucac T
                     (SEQ ID NO: 44)

4) Apt25 Length: 35  (5'-3') sequence:
                     gugaggA CUaUaCC GCg UaaUgC UgC C Uccucac T
                     (SEQ ID NO: 45)

5) Apt26 Length: 33  (5'-3') sequence:
                     gugaggA CUaUaCC gCa AUCG UgC C Uccucac T
                     (SEQ ID NO: 46)

6) Apt27 Length: 33  (5'-3') sequence:
                     gugaggA CUaUaCC GCA aUCg UGC C Uccucac T
                     (SEQ ID NO: 47)

7) Apt28 Length: 33  (5'-3') sequence:
                     gugaggA CUaUaCC gCa aUCg UgC C Uccucac T
                     (SEQ ID NO: 48)

8) Apt29 Length: 33  (5'-3') sequence:
                     gugaggA CUaUaCC GCa aUCg UgC C Uccucac T
                     (SEQ ID NO: 49)
```

Example 6

Stem 2 Sugar Chemistry

The anticoagulant activity of Apt 30-33 was evaluated in standard APTT coagulation assays over compound concentrations ranging from 1 uM to low nanomolar. The "neutralizability" of Apt 30 and 33 was evaluated in standard APTT antidote assays over antidote concentrations (Apt 14 AD) ranging from 5 uM and down. The aptamer concentration was fixed at 125 nM in these assays (see FIG. 10).

Figure 10A:
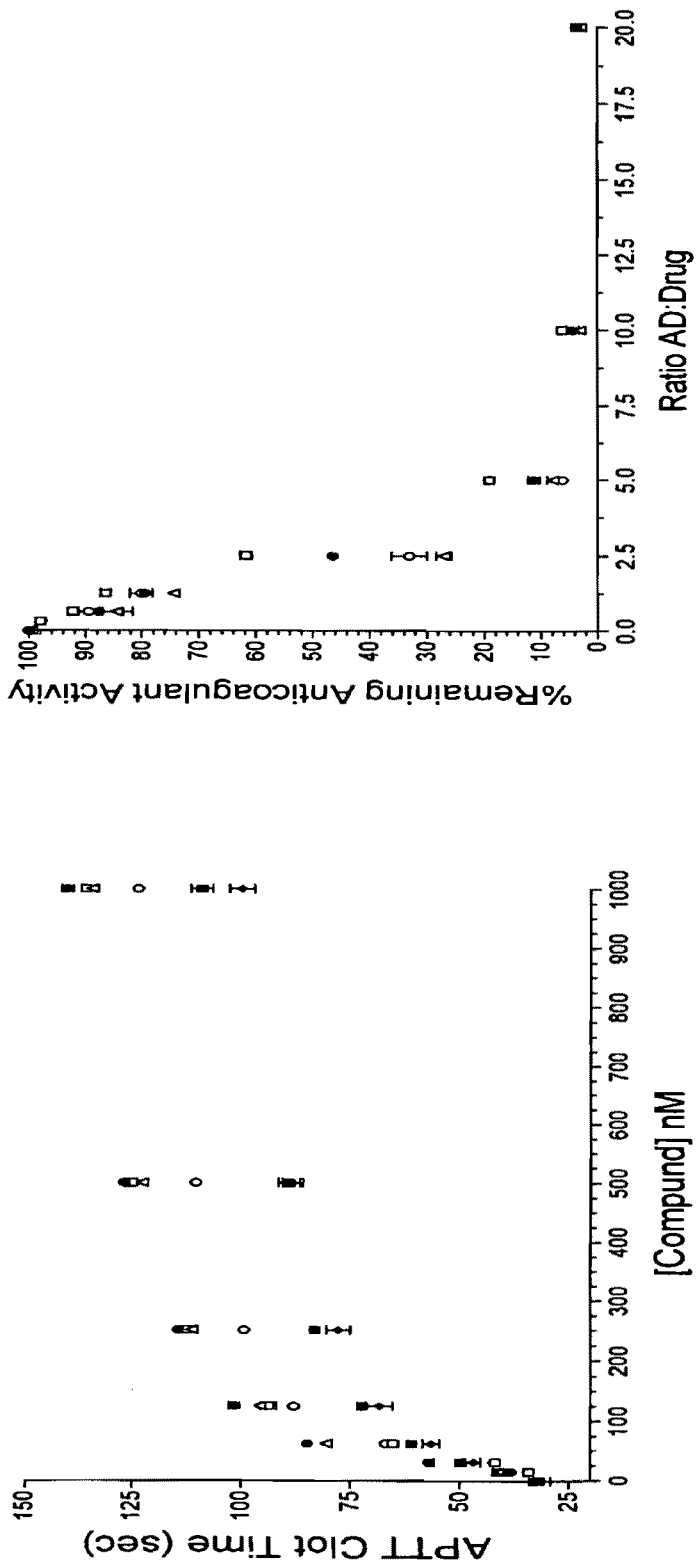
FIG. 10 is a graph of results of activated partial thromboplastin time (APTT) test assays of aptamers Apt 2 and 30-33 (A, left panel), neutralizability by antidote of Apt 2, 30 and 33 (A, right panel), APTT test assays of aptamers Apt 2, 30, 33 and 34 (B, left panel) and neutralizability by antidote (B, right panel).
Figure 10B:
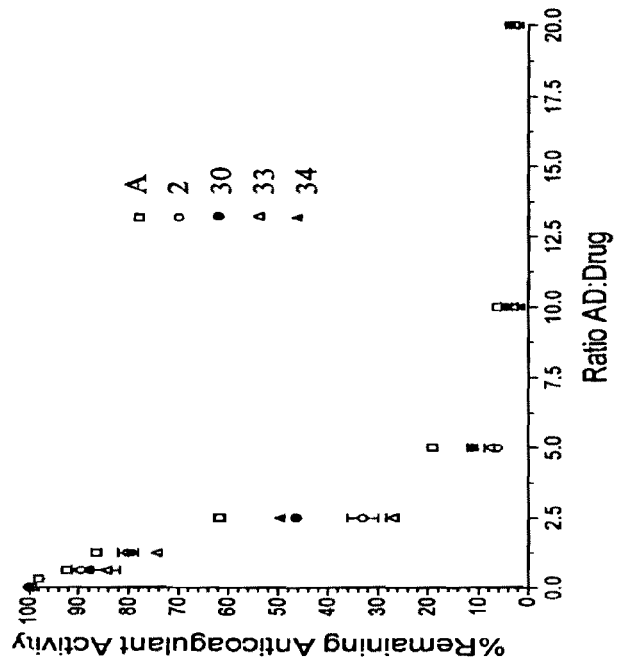
Figure 10B:
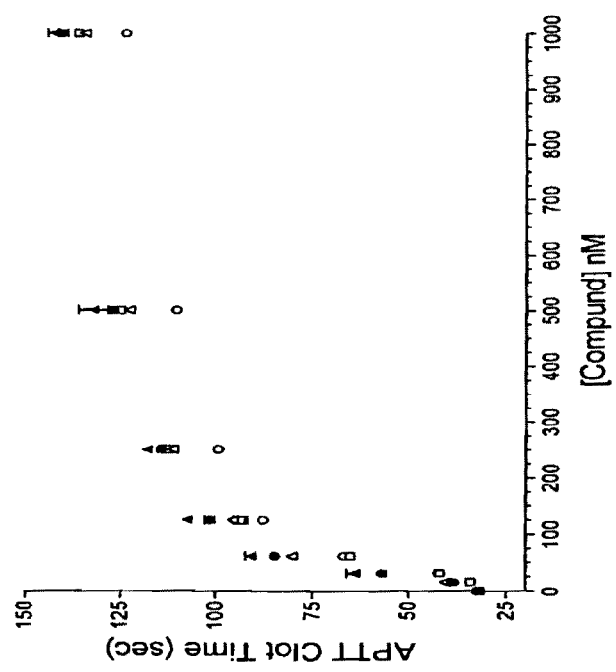

Comparison of the activity of Apt 30 and 33 to Apt 31 and 32 demonstrates that C16 needs to contain a 2' fluoro sugar and G25 a 2' hydroxyl sugar (FIG. 10a). Activity observed between Apt 31 and 32 suggests that remaining positions within stem 2 can contain 2'-O-methyl sugars. In fact, Apt 31 appears to possess slightly greater potency than Apt 32, indicating that a compound with 2' fluoro at C16, 2' hydroxyl at G25, and the remaining residues 2'-O-methyl may exhibit greater potency than Apt 33. Regardless, Apt 33 exhibits greater activity than Apt 2 and is fairly equivalent to original AptA. Apt 33 is more readily neutralizable than Apt 30, suggesting additional 2'-O-methyl residue within the antidote-binding site of the aptamer improves antidote binding.

Apt 34 had C16 a 2' fluoro rather than 2'-O-methyl (FIG. 10*b*). Increase in anticoagulant activity (compare Apt 34 to Apt 33). However, substitution did result in a modest loss of "neutralizability", although 34 still requires a lower excess of antidote to achieve 90% neutralization (~5:1 vs 10:1) than the parental AptA compound. Both results are consistent with an increase in the stability of stem 2 due to 2'-O-methyl substitution.

Sequence Listings:

```
1) Apt30 Length: 35  (5'-3') sequence:
                     gugagga CUaUaCC gCG UaaUgC UGC C Uccucac T
                     (SEQ ID NO: 50)

2) Apt31 Length: 35  (5'-3') sequence:
                     gugagga CUaUaCC gcg UaaUgC ugc C Uccucac T
                     (SEQ ID NO: 51)

3) Apt32 Length: 35  (5'-3') sequence:
                     gugagga CUaUaCC gcg UaaUgC UgC C Uccucac T
                     (SEQ ID NO: 52)

4) Apt33 Length: 35  (5'-3') sequence:
                     gugagga CUaUaCC gCg UaaUgC UGC C Uccucac T
                     (SEQ ID NO: 53)

5) Apt34 Length: 35  (5'-3') sequence:
                     gugagga CUaUaCC gCg UaaUgC uGc C Uccucac T
                     (SEQ ID NO: 54)
```

Example 7

Individual Base Modifications

Apt35-39 compared with original AptA (numbering based upon AptA stem 1):

Sequence Listings:

```
1) Apt35  Length: 31  (5'-3') sequence:
                      gugga CUaUaCC gCG UaaUgC UGC C Uccac T
                      (SEQ ID NO: 55)

2) Apt36  Length: 31  (5'-3') sequence:
                      gugga CUaUaCC gCG UaaUgC ugc C Uccac T
                      (SEQ ID NO: 56)

3) Apt37  Length: 31  (5'-3') sequence:
                      gugga CUaUaCC gCG UaaUgC UgC C Uccac T
                      (SEQ ID NO: 57)

4) Apt38  Length: 31  (5'-3') sequence:
                      gugga CUaUaCC gCg UaaUgC UGC C Uccac T
                      (SEQ ID NO: 58)

5) Apt39  Length: 31  (5'-3') sequence:
                      gugga CUaUaCC gCg UaaUgC uGc C Uccac T
                      (SEQ ID NO: 59)
```

1) Apt 30 to 31: differences are C16, G17, U24, G25, C26.

2) Apt 30 to 32: differences are C16, G17, G25.

3) Apt 31 to 32: differences are U24, C26.

Figure 11:
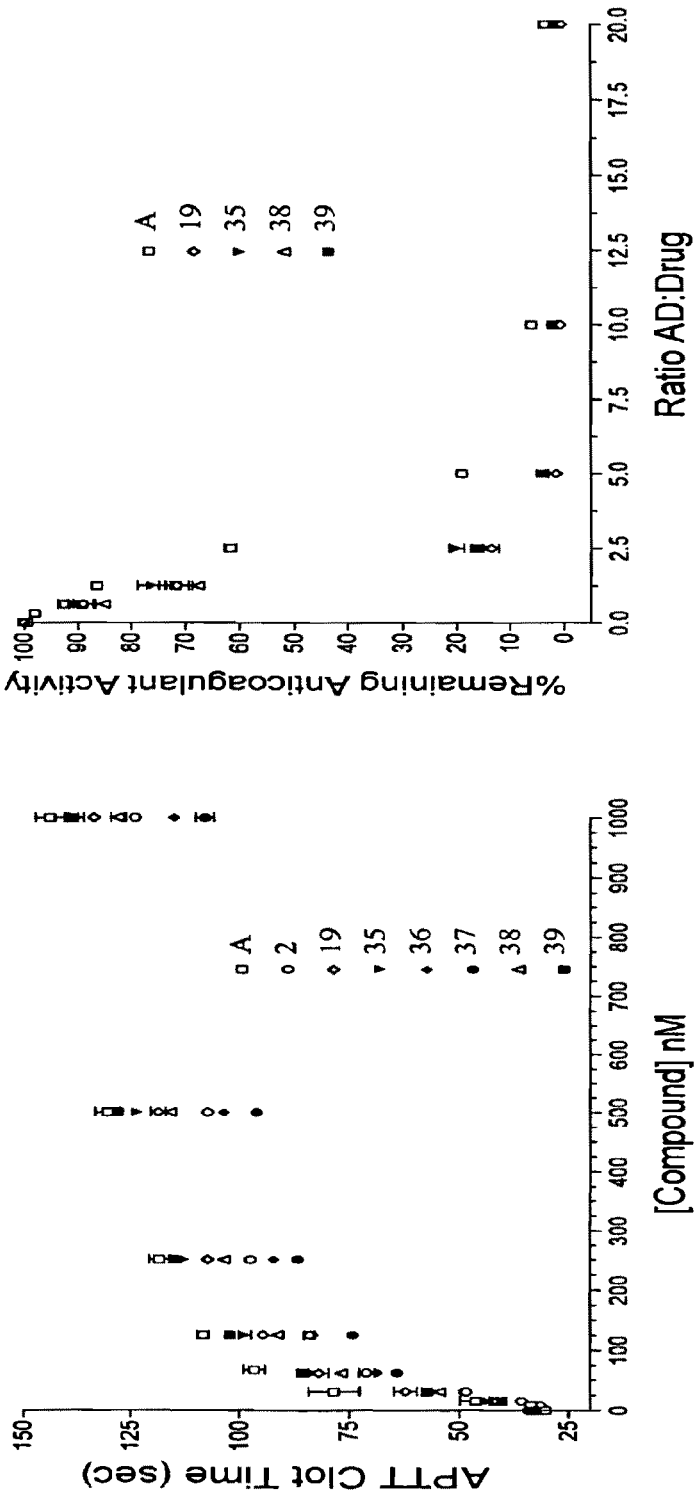
FIG. 11 is a graph of results of activated partial thromboplastin time (APTT) test assays of aptamers Apt A, 2, 19 and 35-39 (left panel) and neutralizability by antidote of Apt A, 19, 35, 38 and 39 (right panel).

The anticoagulant activity of Apt 35-39 was evaluated in standard APTT coagulation assays over compound concentrations ranging from 1 uM to low nanomolar. The "neutralizability" of Apt 35, 38 and 39 was evaluated in standard APTT antidote assays over antidote concentrations (Apt 7 AD) ranging from 5 uM and down. The aptamer concentration was fixed at 125 nM in these assays (FIG. 11).

Figure 12:
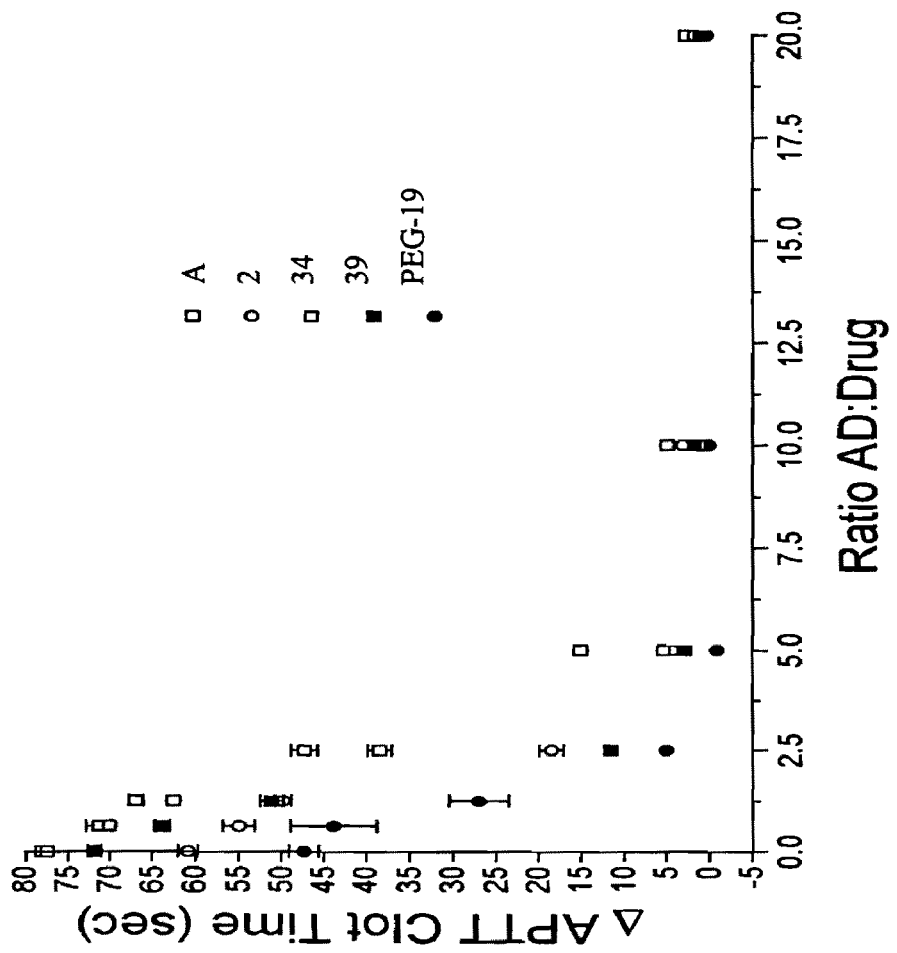
FIG. 12 is a graph of results of neutralizability by antidote assays of aptamers Apt 2, 34, 39 and Peg-19.

Apt 35-39: Anticoagulant activity of Apt 39 is superior to Apt 19 and all other stem 2-optimization constructs in the Apt 19 background (FIG. 11). Results were consistent with those obtained with Apt 34. In addition, potency of Apt 39 is comparable to parental AptA and greater than Apt 2. The neutralization of Apt 39 by Apt7AD is excellent, and similar to neutralization of Apt 19 (FIG. 12). Again, sugar optimization and truncation of Apt 39 has resulted in a compound neutralized at lower excesses of antidote:drug as compared to parental AptA and Apt 2 (FIG. 11).

Example 8

Conjugation of Aptamer to Delivery Vehicle

The anticoagulant tested is Apt39 with a 40 KDa polyethylene glycol (PEG) conjugated to the 5' end of the aptamer sequence via a 6-carbon $NH_2$ linker (PEG-Apt39). The antidote is Apt7AD.

The anticoagulant activity of PEG-Apt39 was evaluated in standard APTT coagulation assays over compound concentrations ranging from 1 uM to low nanomolar. The anticoagulant activity of Apt39 was compared to two formulations of the parental AptA, CH-Apt S (5' cholesterol-modified) and PEG-AptA (5' 40 KDa PEG-modified). For these studies, the molecular weight of the "aptamer" portion only was used to calculate the concentration of each compound. The "neutralizability" of PEG-Apt39 was evaluated in standard APTT antidote assays over antidote concentrations (Apt7AD) ranging from 5 uM and down. The aptamer concentration was fixed at 125 nM in these assays.

Figure 13:
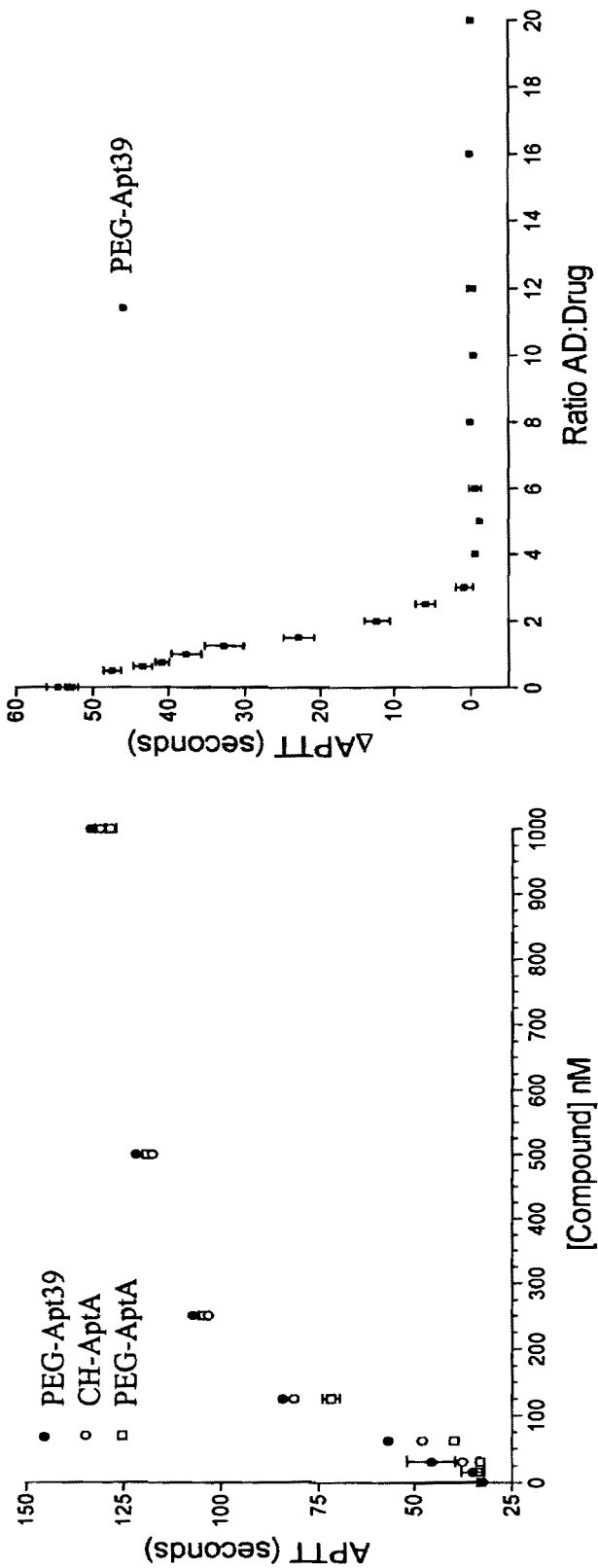
FIG. 13 is a graph of the in vitro anticoagulant activity of PEG-Apt39 compared to CH-AptA and PEG-AptA.

The in vitro anticoagulant activity of PEG-Apt39 is essentially equivalent to CH-AptA and PEG-AptA (FIG. 13).

In Vivo Studies

This study compares the in vivo anticoagulant and antidote neutralization activity of PEG-Apt39 in swine to previous data obtained with CH-AptA with respect to: a) Potency and durability of anticoagulant activity and the b) Neutralization of anticoagulant activity. The three experimental groups (n=2 animals for each) are a) Systemic anticoagulation; b) Systemic anticoagulation and drug neutralization; and c) Systemic anticoagulation, drug neutralization and re-anticoagulation.

Experiment: Six neonatal piglets (1 week old, 2.5-3.5 kg) were randomly assigned to three groups. Femoral arterial and venous lines were placed in the piglet. The arterial line was used to monitor blood pressure and arterial blood sampling. The venous line was used to administer drugs and test compounds as specified. Temperature of the piglet was monitored with a nasopharyngeal temperature probe.

Figure 14A:
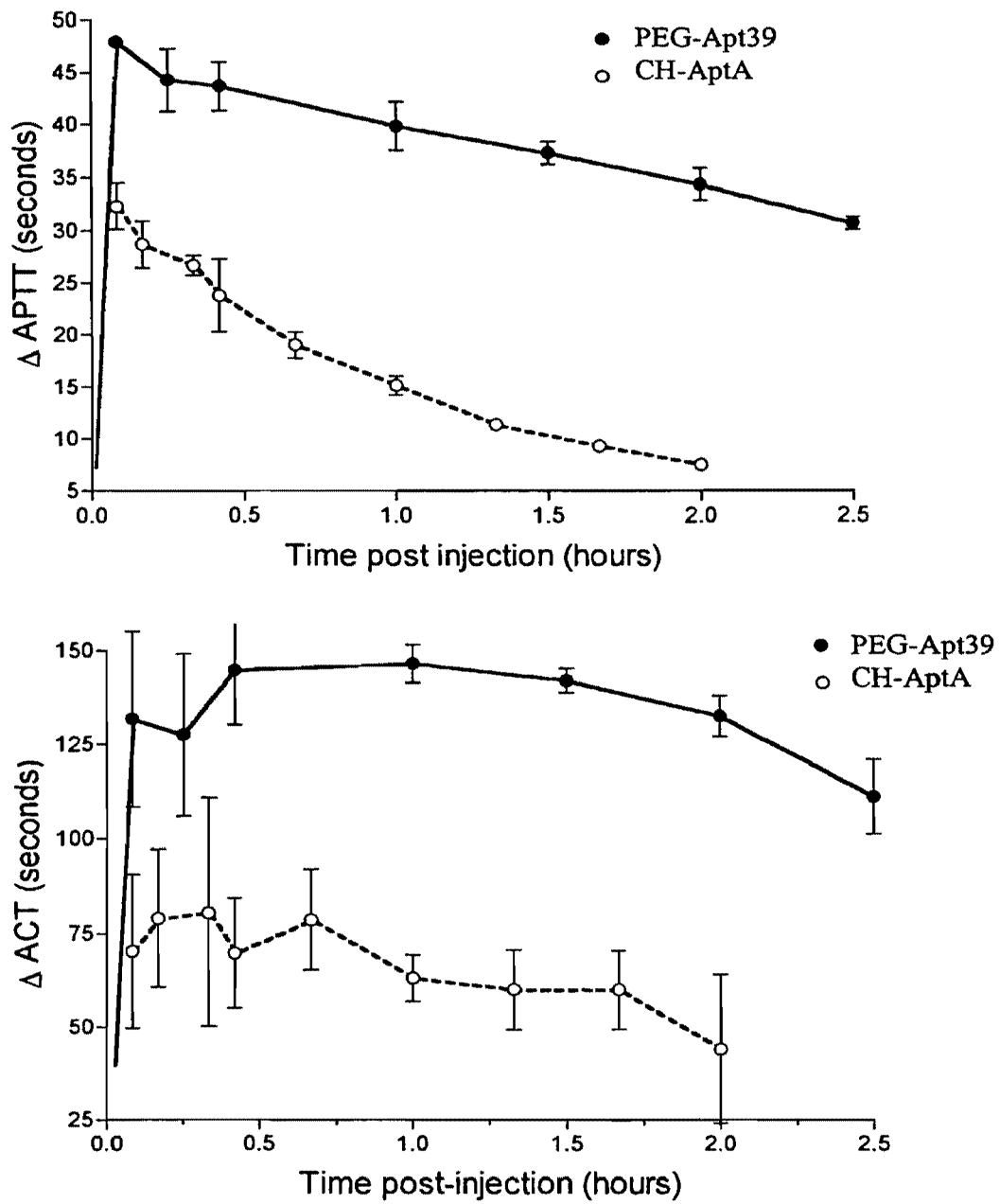
FIG. 14 are graphs of systemic anticoagulant activity (14a) and neutralizability (14b) of PEG-Apt39 in swine. The change in the value of the respective clotting assays is the difference between the clotting time at the time point and the pre-injection baseline for that animal. n=2 for PEG-Apt39 treated animals and n=3 for CH-AptA treated animals. Whole blood ACT values are shown in the bottom panel, and plasma APTT values in the panel at the top.

The dose of PEG-Apt39 was 0.5 mg/kg (dose of aptamer based upon molecular weight of nucleic acid component only; 10,103.2 Da) for each animal. In the prior experiments with CH-AptA, the aptamer dose was also 0.5 mg/kg (dose of aptamer based upon molecular weight of nucleic acid component only). In experiments in which Apt7 AD was used as an antidote, the dose of the antidote was 3 mg/kg. By comparison, in experiments with CH-AptA in which AptA AD was used, the antidote dose was 5 mg/kg.

a) Systemic anticoagulation. A pre-injection blood sample was taken prior to injection of PEG-Apt39, the drug was then injected (time of injection is t=0), and blood samples removed at 5, 15, 25, 60, 90, 120 and 150 minutes post injection. Activated clotting times (ACT's) were performed on-site immediately after blood draw on the whole blood in duplicate using the Hemochron 801 junior and glass-activated flip-top tubes per the manufacturers directions. Blood samples were then transferred to citrated vacutainer tubes and stored on ice. Platelet poor plasma was prepared, and APTT and PT assays performed per the standard protocol. (FIG. 14A)

The in vivo anticoagulant potency of PEG-Apt39 is superior to CH-AptA. In addition, the loss of anticoagulant activity over time is reduced for PEG-Apt39 vs. CH-AptA. These results are in contrast with the in vitro anticoagulant activity studies, which demonstrate that the anticoagulant activity of PEG-Apt39 and CH-AptA are equivalent in vitro in pooled human plasma.

b) Systemic anticoagulation and drug neutralization. A pre-injection blood sample was taken prior to injection of PEG-Apt39, the drug was then injected (0.5 mg/kg; time of injection is t=0), and blood samples removed at 5 and 15 minutes post drug injection. At t=15 minutes post drug injection, REG1 S7 AD was administered (3 mg/kg), and additional blood samples removed at 25, 60, 90, 120 and 150 minutes post drug injection. Activated clotting times (ACT's) were performed on-site immediately after blood draw on the whole blood in duplicate using the Hemochron 801 junior and glass-activated flip-top tubes per the manufacturers directions. Blood samples were then transferred to citrated vacutainer tubes and stored on ice. Platelet poor plasma was prepared, and APTT and PT assays performed per the standard protocol.

Figure 14B:
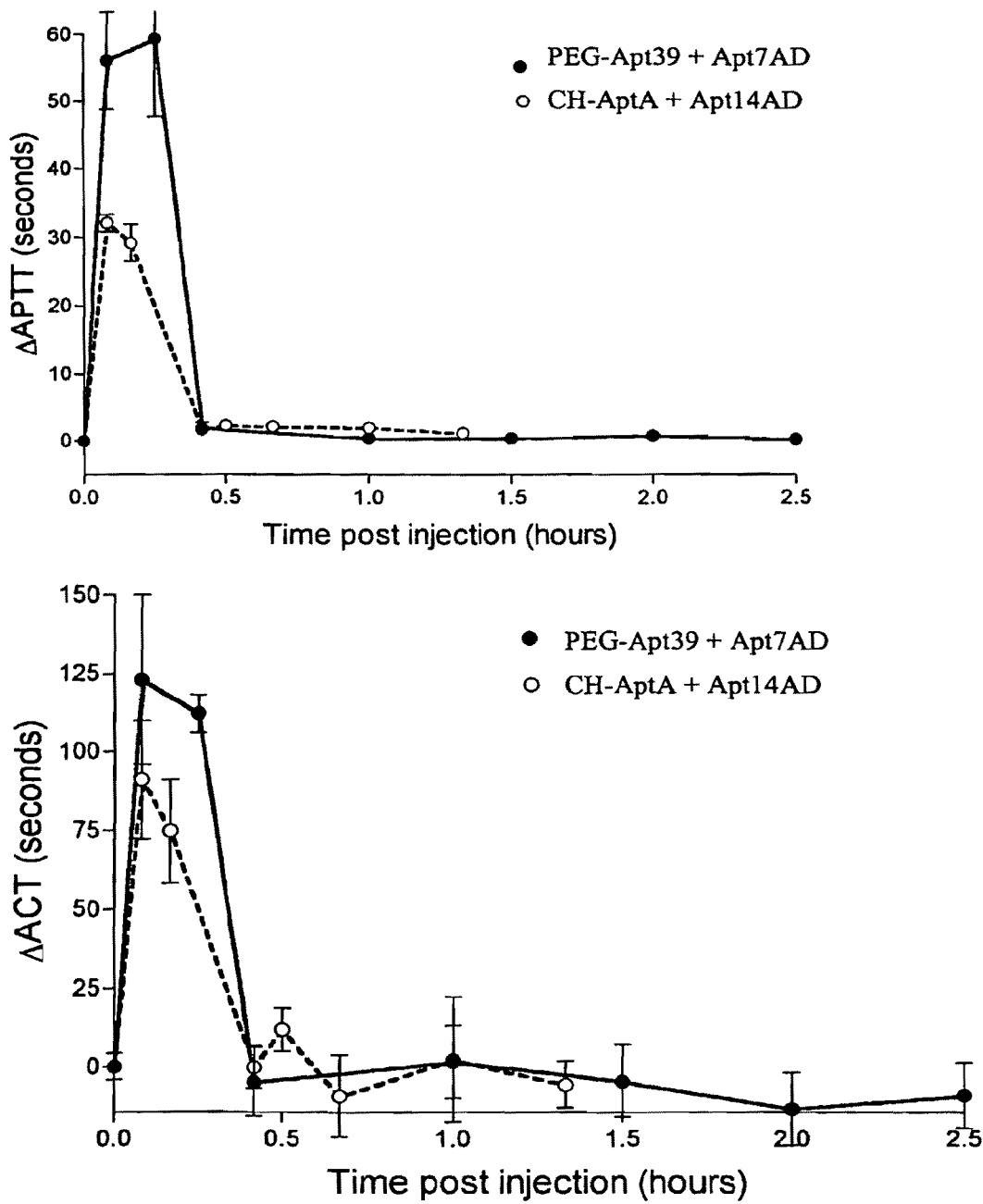
Figure 15:
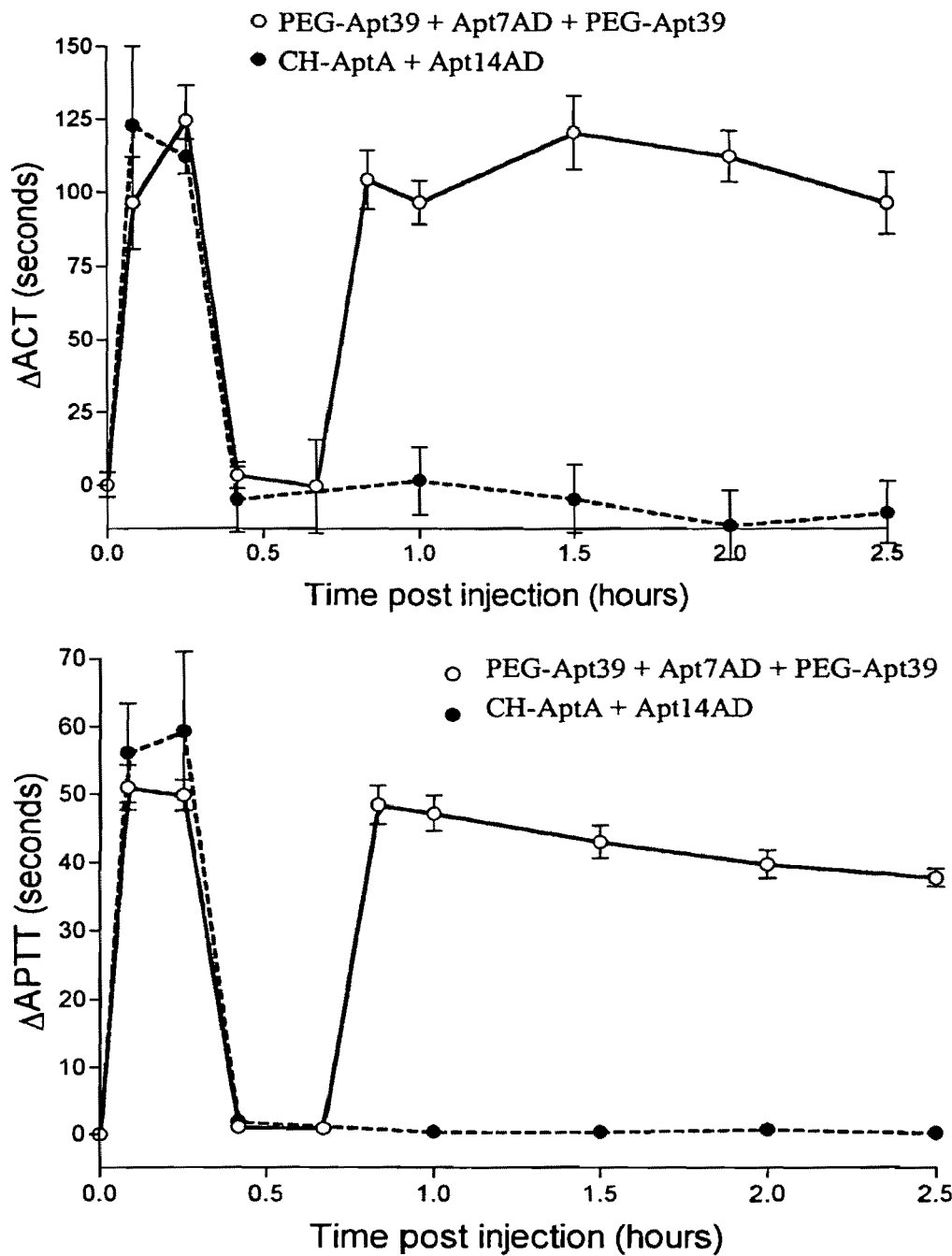
FIG. 15 is graphs of systemic anticoagulant activity (14a) and neutralizability (14b) of PEG-Apt39 in swine. The change in the value of the respective clotting assays is the difference between the clotting time at the time point and the pre-injection baseline for that animal. n=2 for PEG-Apt39 treated animals. Data from this experiment is compared to the anticoagulation and neutralization data for PEG-Apt39 presented in FIG. 3. Whole blood ACT values are shown in the left panel, and plasma APTT values in the panel at right.

Essentially complete neutralization of the anticoagulant activity of PEG-Apt39 was achieved within 10 minutes of administration of 3 mg/kg Apt7 AD. The anticoagulant activity remained neutralized throughout the remainder of the experiment (2 hr and 5 min after initial demonstration of drug neutralization). Thus, the neutralization of PEG-Apt39 appears to be superior to that of CH-AptA, as similar levels of neutralization of PEG-Apt39 can be achieved with a 40% lower dose of antidote (3 mg/kg of Apt7 AD vs. 5 mg/kg REG1 AD). This in vivo data is consistent with in vitro experiments in pooled human plasma in which PEG-Apt39 is more readily neutralized by its matched antidote than any prior formulation of AptA. (FIG. 14B)

c) Systemic anticoagulation, drug neutralization and re-anticoagulation. A pre-injection blood sample was taken prior to injection of PEG-Apt39, the drug was then injected (0.5 mg/kg; time of injection is t=0), and blood samples removed at 5 and 15 minutes post drug injection. At t=15 minutes post drug injection, Apt7 AD was administered (3 mg/kg), and additional blood samples removed at 25, and 40 minutes post drug injection. At t=45 minutes post drug injection (30 minutes following antidote administration), PEG-Apt39 was re-administered (0.5 mg/kg) and additional blood samples removed at 50, 60, 90, 120, and 150 minutes post drug injection. Activated clotting times (ACT's) were performed on-site immediately after blood draw on the whole blood in duplicate using the Hemochron 801 junior and glass-activated flip-top tubes per the manufacturers directions. Blood samples were then transferred to citrated vacutainer tubes and stored on ice. Platelet poor plasma was prepared, and APTT and PT assays performed per the standard protocol. (FIG. 15)

Re-administration of PEG-Apt39 following neutralization of the initial drug dose is feasible within 30 minutes of administration of the neutralizing antidote. The levels of anticoagulation achieved following administration of the first and second dose appear to be equivalent to each other, suggesting that there is little remaining "free" antidote in the circulation at the time of administration of the second dose of drug.

Example 9

Quantification of Aptamer Complex Formation in Plasma

Aptamer levels in plasma are determined using a sandwich-type hybridization assay with an enzyme-linked immunoassay (ELISA) for detection. Quantitation of aptamer employs two oligonucleotide probes, a DNA capture probe, and a 2'Omethyl RNA detection probe. The DNA capture probe is 15 nucleotides in length, is complementary to the 3' terminal 15 nucleotides of the aptamer, and contains a biotin moiety on its 5' terminus, allowing for capture of oligonucleotide complexes containing this probe to an avidin coated surface. The 2'Omethyl RNA detection probe is also 15 nucleotides in length, is complementary to the portion of aptamer to which antidote binds, and contains a digoxigenin moiety to enable detection of complexes containing this probe using standard enzyme-linked fluorescence generating enzyme/substrate reagents.

Quantitation of aptamer is achieved by hybridization of the capture and detection probes to aptamer in plasma and subsequent immobilization of the complex onto the surface of a Neutravidin-coated microtitre plate by way of the 5'-biotin group. Measurement of the digoxigenin-labeled 2'-O-methyl RNA probe is performed subsequent to the plate immobilization reaction using an anti-digoxigenin antibody conjugated to alkaline phosphatase, which catalyzes the fluorescence of a substrate. Fluorescence intensity is then measured, the signal of which is directly proportional to the amount of aptamer present in the calibration standards and validation samples.

The in vitro anticoagulant activity of aptamer Apt39 (SEQ ID NO:88) in plasma from cynomolgus monkeys is reflected by concentration-dependent prolongation of time-to-clot in the APTT assay. Plasma FIX assays were performed to aid in interpretation of the Apt39 APTT dose-response curve in monkey plasma. As shown in Table A, the APTT in monkey plasma is sensitive to the FIX level. However, the magnitude of the response to reduction in the FIX level is modest. A 75% reduction in the FIX level results in a 1.4-fold increase in the APTT, a >95% reduction in the FIX level results in a doubling of the APTT, and a 99.9% reduction in the plasma FIX level yields a 2.5-fold increase in the APTT.

TABLE A

FIX Activity Assay Standard Curve in Cynomolgus Monkey Plasma

| % FIX Level | APTT Clot Time | Fold Increase in Clot Time |
| --- | --- | --- |
| 100* | 35.1 | 1.0 |
| 50 | 41.9 | 1.2 |
| 25 | 49.4 | 1.4 |
| 12.5 | 55.9 | 1.6 |
| 6.25 | 62.2 | 1.8 |
| 3.13 | 68.0 | 1.9 |
| 1.56 | 74.7 | 2.1 |
| 0.78 | 77.7 | 2.2 |
| 0.39 | 83.8 | 2.4 |
| 0.098 | 88.1 | 2.5 |

*100% FIX level represents a 1:5 dilution of normal pooled cynomolgus plasma in buffer. Human FIX-deficient plasma (George King Biomedical) was used as the source of FIX-deficient plasma.

The date in table A indicate that ~6 µg/mL Apt39 is required to inhibit approximately 90% of plasma FIX activity in monkeys (i.e., this concentration yields a 1.6-fold increase in the APTT), and that >95% inhibition of plasma FIX activity occurs at Apt39 concentrations of 10-12 µg/mL.

In Vivo Activity of Apt39 and Apt7AD in Cynomolgus Monkeys

The relationship between the anticoagulant properties of Apt39 and the Apt39/Apt7AD complex and the plasma levels of these compounds was evaluated in monkey. Briefly, 12 monkeys were assigned to three treatment groups. Group 1 received the anti-FIXa aptamer Apt39, Group 2 received the antidote Apt7AD and Group 3 was treated with Apt39 and three hours later with Apt7AD. Doses were escalated through two quantities of test articles, with the first dose occurring on Day 4 of the study and the second dose occurring on Day 13. To better understand the dose-response to aptamer, the four monkeys assigned to Group 1 were subdivided into two groups at Day 13, with two animals receiving a low dose (Group 1a, 5 mg/kg) and two animals receiving a high dose (Group 1b, 30 mg/kg).

Figure 16:
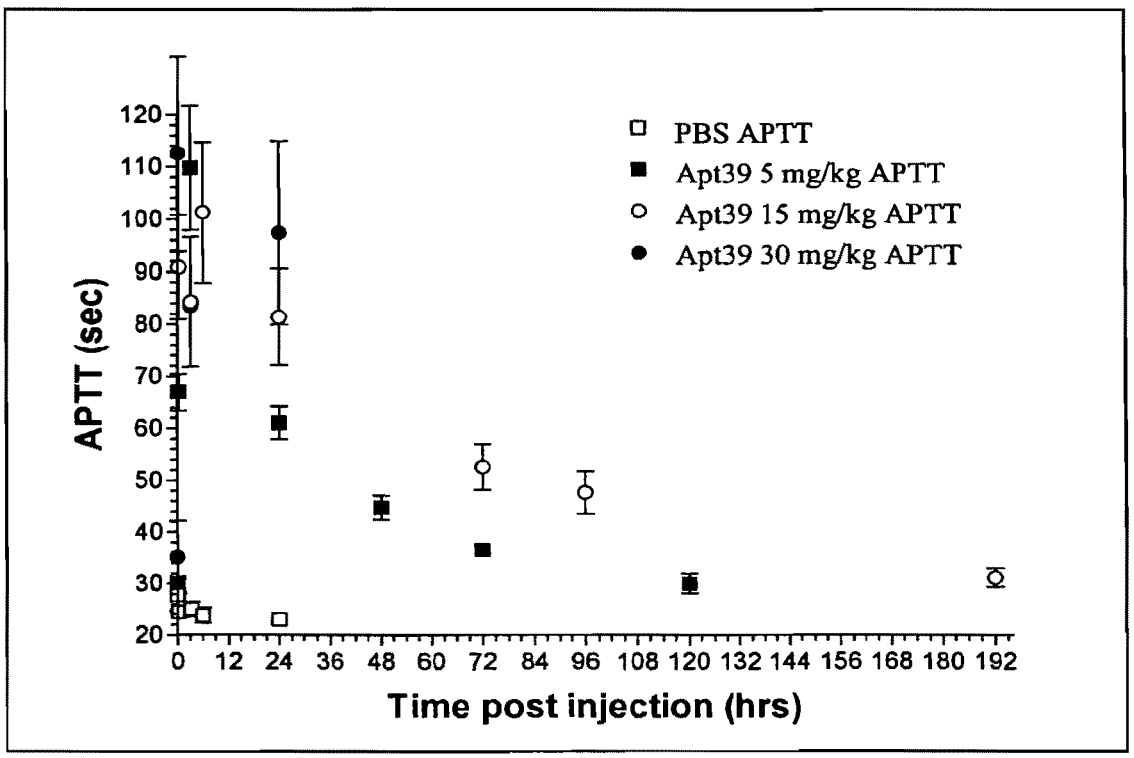
FIG. 16 is a graph of systemic anticoagulation of monkeys by Apt39 administration as described in Example 9. The level of anticoagulation in the monkeys was monitored with the APTT. For animals treated with 15 mg/kg, Apt39 data are presented as the mean±SEM. For animals at the 5 and 30-mg/kg dose levels, data are presented as the mean±range, as there were only 2 animals at each of these dose levels.

As shown in FIG. 16, administration of Apt39 at doses ranging from 5 to 30 mg/kg resulted in a profound level of anticoagulation in the monkeys. The mean APTT at each dose level exceeded 60 seconds from 0.25 to 24 hours following aptamer administration, which is equivalent to <0.1% normal plasma FIX levels in the monkey. There is a dose-dependent increase in APTT in response to Apt39 administration. However, the dose-response is not immediately evident due to the fact that, up to the 6-hour time point following Apt39 administration, the aptamer plasma level exceeded the concentration at which the in vitro APTT dose-response curve approaches a plateau (~40-50 µg/mL; see Table B). At times beyond 6 hours after administration, as the aptamer concentration decreases below this level, the dose-response is more apparent. APTT was followed until it returned to baseline in monkeys receiving 5 and 15 mg/kg doses. Mean APTT returned to baseline by 120 hours at the 5-mg/kg dose level and 192 hours at the 15-mg/kg dose level, consistent with both the in vitro APTT dose-response curve (data not shown) and the observed half-life of approximately 12 hours in monkeys (see Table B). The whole-blood activated clotting time (ACT) data mirrored the APTT data (data not shown).

There is an excellent correspondence between the mean Apt39 concentration 24 hours post administration in the Group 1a animals and the mean APTT of these animals. The mean aptamer concentration of the animals treated with 5 mg/kg at 24 hours was 15.9 µg/mL and the mean APTT was 61.1 seconds.

TABLE B

Group 1 Apt39 Plasma Levels (µg/mL)

| Time Post Injection (hours) | Group 1 Dose Levels (animals/dose level) | | |
| --- | --- | --- | --- |
| | 5 mg/kg (n = 2)* | 15 mg/kg (n = 4) | 30 mg/kg (n = 2)* |
| Pre-dose | 0.2 | <0.04 | 0.2 |
| 0.25 | 59.8 | 179.8 ± 28.9 | 465.5 |
| 3 | 66.6 | 145.6 ± 32.5 | 328.9 |
| 6 | 42.1 | 101.5 ± 13.4 | 275.3 |
| 24 | 15.9 | 51.1 ± 11.2 | 164.6 |

*For Day 13 dosing, animals were split into Group 1a (5 mg/kg) and 1b (30 mg/kg). For these dose levels, the average plasma level for the two animals per dose level is reported. The Apt39 present in Group 1a and 1b animals at the pre-dose time point is residual Apt39 from the 15-mg/kg dose at Day 4. The LLOQ of the assay is <0.04 µg/mL.

In the Group 2 animals treated with the antidote only, mean APTT and ACT were not affected by antidote administration at either dose level tested (30 and 60 mg/kg). Toxicokinetic data were collected at several time points over the first 24 hours after administration. As shown in Table C, low, but measurable levels of the antidote were present in plasma from animals receiving antidote at 0.25 hours after injection of 30 mg/kg on Day 4 or 60 mg/kg on Day 13. The post-dosing level of the antidote was very low by comparison to the concentration of the aptamer (in Group 1) following IV injection.

TABLE C

Group 2 Apt7AD Plasma Levels (µg/mL)

| Time Post Apt39 Injection (hours) | Group 2 Dose Levels (4 animals/dose) | |
| --- | --- | --- |
| | 30 mg/kg | 60 mg/kg |
| Pre-dose | <0.01 | <0.01 |
| 3.25 | 0.4 ± 0.1 | 0.6 ± 0.5 |
| 6 | 0.02 ± 0.01* | <0.02*** |
| 24 | 0.01 ± 0.01** | <0.01*** |

Figure 17:
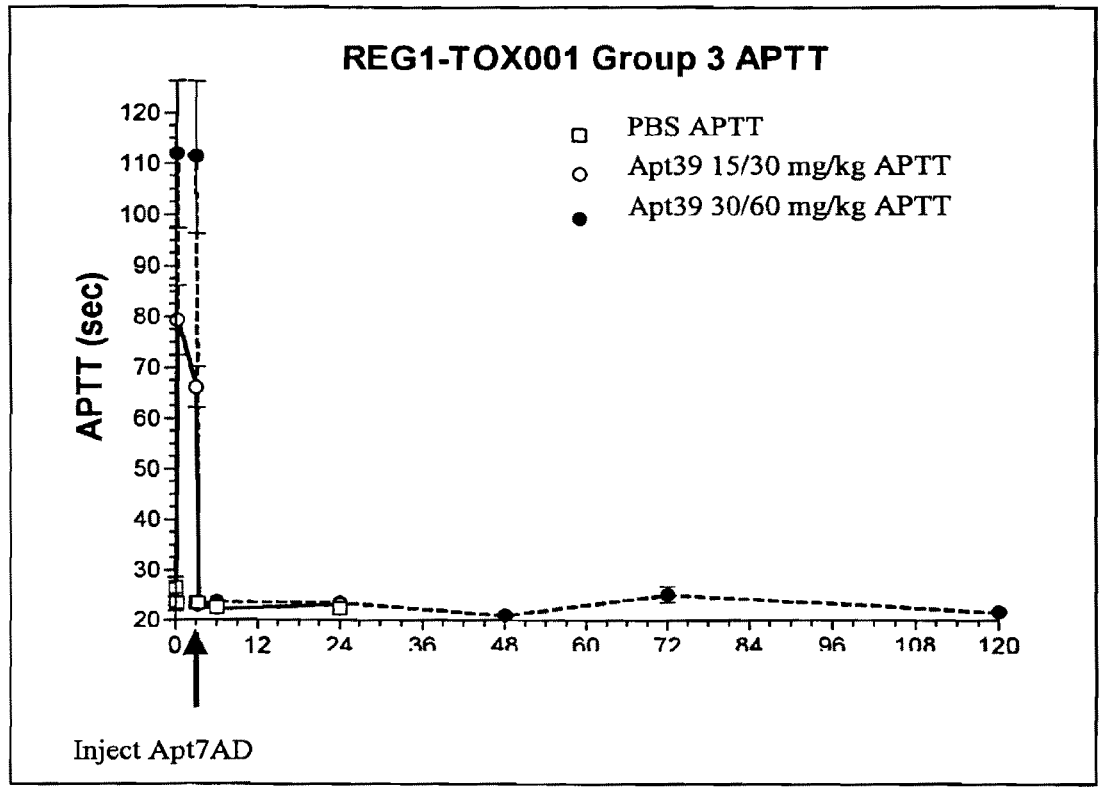
FIG. 17 is a graph of the systemic anticoagulation of monkeys with Apt39 and reversal with antidote Apt7AD, as described in Example 9. The level of anticoagulation in the monkeys was monitored with the APTT. Apt7AD was administered at t=3 hours following Apt39 administration. Data are presented as the mean±SEM.

*1 animal at <LLOQ of 0.01 included in calculations
**3 animals at <LLOQ of 0.01 included in calculations
***Average of LLOQs The APTT data from animals treated with aptamer followed by antidote 3 hours later (Group 3) are shown in FIG. 17. In agreement with the data from animals treated with aptamer only, administration of aptamer at these dose levels resulted in a profound level of anticoagulation, with the mean APTTs at 0.25 and 3 hours post administration consistent with essentially complete FIX inhibition at both dose levels. Subsequent administration of Apt7AD rapidly and completely neutralized the anticoagulant effects of Apt39 in the monkey, with the mean APTT returning to baseline within 15 minutes following Apt7AD administration. In the Group 3 animals treated with 30/60 mg/kg Apt39/Apt7AD, the APTT was followed for 5 days post aptamer administration. APTT data collected over this time frame indicate the anticoagulant effects of aptamer were durably neutralized, with no evidence of rebound anticoagulation over 120 hours, or approximately 10 half-lives of aptamer in the monkey (FIG. 17).

Toxicokinetic data were collected for 24 hours following Apt39 administration in the Group 3 animals (Table D). For Group 3 animals, both free aptamer and complexed aptamer plasma concentrations were measured. Within 15 minutes of antidote administration, the mean concentration of free aptamer decreased 5,000-10,000 fold, to levels below the Lower Limit of Quantitation (LLOQ) of the assay employed. Concomitant with the decrease in free aptamer levels, the mean plasma concentration of complexed aptamer increased from below the LLOQ of the assay to ~125 to 220 µg/mL at the 15/30 and 30/60 mg/kg dose levels respectively, indicating the rapid decrease in free Apt39 concentrations was due to binding of Apt7AD. The concentration of free aptamer remained below the LLOQ of the assay as long as 3 hours after antidote administration, consistent with the APTT results. At 21 hours after antidote administration, very low levels of Apt39 were detectable in several animals (mean of only 0.17 µg/mL or lower).

TABLE D

| | Group 3 Free and Complexed Apt389 Plasma Levels (µg/mL) | | | |
|---|---|---|---|---|
| Time Post | Group 3 Dose Levels | | | |
| Apt39 | 15/30 mg/kg Apt39 + Apt7AD | | 30/60 mg/kg Apt39 + Apt7AD | |
| Injection (hours) | Free Apt39 | Complexed Apt39 | Free Apt39 | Complexed Apt39 |
| Pre-dose | <0.04 | ND | 0.05 ± 0.01 | ND |
| 0.25 | 280.2 ± 64.3 | ND | 467.6 ± 67 | ND |
| 3.0 | 214.6 ± 31.8 | <0.04 | 488.4 ± 68.6 | <0.04 |
| 3.25 | <0.04 | 125.1 ± 7.9 | <0.04 | 218.2 ± 27.2 |
| 6 | <0.04 | 98.7 ± 20.5 | <0.04 | 184.8 ± 28.9 |
| 24 | 0.14 ± 0.08* | 8.3 ± 4.5 | <0.04 ± 0.01** | 22.3 ± 12 |

*1 animal at <LLOQ of 0.04 µg/mL included in calculations
**3 animals at <LLOQ of 0.04 µg/mL included in calculations
Apt7AD administered at t = 3 hrs immediately after 3 hr blood draw. (ND) Not determined.

The invention has been described with reference to various specific and preferred embodiments and techniques. It should be understood that many variations and modifications may be made while remaining within the spirit and scope of the invention.

The invention claimed is:

1. A first isolated nucleic acid comprising a nucleic acid sequence comprising SEQ ID NO:17.

2. The first nucleic acid of claim 1, comprising a three dimensional structure comprising a first and a second stem wherein the first stem comprises five nucleotides.

3. The first isolated nucleic acid of claim 1, wherein the first isolated nucleic acid further comprises a suicide position that becomes single stranded upon binding of an antidote oligonucleotide, wherein the antidote oligonucleotide is complementary to the first isolated nucleic acid and wherein the antidote oligonucleotide hybridizes to the first isolated nucleic acid.

4. An isolated nucleic acid wherein the isolated nucleic acid comprises SEQ ID NO:8.

5. The first isolated nucleic acid of claim 1, wherein one or more nucleotides are modified, wherein the modification is a 2'-O-methyl modification or a 2'-O-fluoro modification.

6. The first isolated nucleic acid of claim 2, wherein at least one guanine in the second stem comprises a hydroxyl sugar (2'-OH).

7. The first isolated nucleic acid of claim 2, wherein at least one cytidine in the second stem comprises a 2'-fluoro modification.

8. The first isolated nucleic acid of claim 1, wherein the first isolated nucleic acid comprises modifications as presented in the sequence selected from the group consisting of SEQ ID NOs: 34-37, SEQ ID NO:41-49, and SEQ ID NO:50-54.

9. The first isolated nucleic acid of claim 1, wherein the first isolated nucleic acid is attached to a water soluble polymer.

10. The first isolated nucleic acid of claim 9, wherein the water soluble polymer is polyethylene glycol.

11. A pharmaceutical composition comprising the isolated nucleic acid of claim 1 in combination with a pharmaceutically acceptable carrier.

12. A method for inhibiting coagulation in a host in need thereof, comprising administering to the host a therapeutically effective amount of a nucleic acid ligand comprising a SEQ ID NO:17.

13. The method according to claim 12, wherein the nucleic acid ligand comprises a modified nucleotide modified by a 2'-O-methyl modification or a 2'-O-fluoro modification.

14. The method according to claim 12, wherein the nucleic acid ligand is selected from the group consisting of SEQ ID NO:34-37, SEQ ID NO:41-49, and SEQ ID NO:50-54.

15. The method according to claim 12, wherein the host is suffering from or at risk of suffering from a disorder selected from the group consisting of acute myocardial infarction (heart attack), cerebrovascular accidents (stroke), ischemia, angioplasty, CABG (coronary artery bypass grafts), cardiopulmonary bypass, thrombosis in the circuit of cardiac bypass apparatus and in patients undergoing renal dialysis, unstable angina, pulmonary embolism, deep vein thrombosis, arterial thrombosis, and disseminated intravascular coagulation.

16. The method according to claim 12, wherein the administering is intravenous, subcutaneous, transdermal or parenteral administration.

17. A method of modulating coagulation in a host in need thereof comprising administering to the host a first isolated nucleic acid sequence comprising SEQ ID NO:17, wherein the first isolated nucleic acid sequence optionally includes one or more nucleotide modifications selected from a 2'-O-methyl modification or a 2'-O-fluoro modification, and administering an effective amount of a second isolated nucleic acid sequence comprising SEQ ID NO:8, wherein the administering of the second nucleic acid sequence is done after the administering the first nucleic acid sequence, and wherein the second nucleic acid sequence reverses the effects of the first nucleic acid sequence.

* * * * *